US012629100B2

(12) United States Patent
Zhou et al.

(10) Patent No.: US 12,629,100 B2
(45) Date of Patent: May 19, 2026

(54) CLASSIFYING BIOMEDICAL ACOUSTICS BASED ON IMAGE REPRESENTATION

(71) Applicant: Cornell University, Ithaca, NY (US)

(72) Inventors: George Zhou, Saratoga, CA (US);
Candace Chien, Kinnelon, NJ (US);
Yunchan Chen, Del Mar, CA (US)

(73) Assignee: Cornell University, Ithaca, NY (US)

( * ) Notice: Subject to any disclaimer, the term of this patent is extended or adjusted under 35 U.S.C. 154(b) by 295 days.

(21) Appl. No.: 18/212,470

(22) Filed: Jun. 21, 2023

(65) Prior Publication Data

US 2023/0329646 A1      Oct. 19, 2023

Related U.S. Application Data

(63) Continuation-in-part of application No. PCT/US2021/064926, filed on Dec. 22, 2021.
(Continued)

(51) Int. Cl.
*G16H 50/30*          (2018.01)
*A61B 5/00*          (2006.01)
(Continued)

(52) U.S. Cl.
CPC ........... *A61B 5/7267* (2013.01); *A61B 7/003* (2013.01); *G16H 50/20* (2018.01); *G16H 50/30* (2018.01); *G16H 70/60* (2018.01)

(58) Field of Classification Search
CPC ...... G16H 50/20; G16H 50/30; A61B 5/7267; A61B 7/003
See application file for complete search history.

(56) References Cited

U.S. PATENT DOCUMENTS 4,905,706 A    3/1990  Duff et al.
5,025,809 A    6/1991  Johnson et al.
(Continued)

FOREIGN PATENT DOCUMENTS

AU       2018201007 A1    8/2018
CA          3025748 A1   12/2017
(Continued)

OTHER PUBLICATIONS

"Encoding Time Series as Images for Visual Inspection and Classification Using Tiled Convolutional Neural Networks", Wang et al., 2015.*
(Continued)

*Primary Examiner* — Richemond Dorvil
*Assistant Examiner* — Adam Michael Weaver
(74) *Attorney, Agent, or Firm* — Ryan, Mason & Lewis, LLP

(57)          ABSTRACT

A method in an illustrative embodiment comprises obtaining an acoustic signal for a given individual, generating an image representation of at least a portion of the acoustic signal, processing the image representation in at least one neural network of an acoustics classifier to generate a classification for the acoustic signal, and executing at least one automated action based at least in part on the generated classification. The acoustic signal illustratively comprises, for example, at least one of a heart sound signal, a blood flow sound signal, a lung sound signal, a bowel sound signal, a cough sound signal, or other physiological sound signal of the given individual. Generating the image representation illustratively comprises generating at least one spectrogram. Additionally or alternatively, generating the image representation may comprise generating one or more recurrence plots, Markov transition field image representations and/or Gramian angular field image representations.

34 Claims, 20 Drawing Sheets

Related U.S. Application Data

(60) Provisional application No. 63/129,179, filed on Dec. 22, 2020.

(51) Int. Cl.
_A61B 7/00_ (2006.01)
_G16H 50/20_ (2018.01)
_G16H 70/60_ (2018.01)

(56) References Cited

U.S. PATENT DOCUMENTS

| | | | |
|---|---|---|---|
| 6,440,082 | B1 | 8/2002 | Joo et al. |
| 6,572,560 | B1 | 6/2003 | Watrous et al. |
| 7,458,939 | B2 | 12/2008 | Munk |
| 8,649,854 | B2 | 2/2014 | Sepehri et al. |
| 8,992,435 | B2 | 3/2015 | Pretorius et al. |
| 9,687,208 | B2 | 6/2017 | Tsai et al. |
| 9,974,488 | B2 | 5/2018 | Najarian et al. |
| 10,609,284 | B2 * | 3/2020 | Kang ........................ G06T 7/20 |
| 10,702,239 | B1 | 7/2020 | McLane |
| 10,709,353 | B1 | 7/2020 | McLane |
| 10,709,414 | B1 | 7/2020 | McLane |
| 10,959,629 | B2 | 3/2021 | Kaiser et al. |
| 11,373,757 | B2 | 6/2022 | Das et al. |
| 2005/0222515 | A1 | 10/2005 | Polyshchuk et al. |
| 2006/0142667 | A1 | 6/2006 | Munk |
| 2013/0226019 | A1 | 8/2013 | Pretorius et al. |
| 2014/0180036 | A1 * | 6/2014 | Bukkapatnam ...... A61B 5/0816 |
| | | | 128/845 |
| 2015/0106020 | A1 * | 4/2015 | Chung ................... G16H 40/67 |
| | | | 702/19 |
| 2015/0157218 | A1 | 6/2015 | Ahmad et al. |
| 2016/0120416 | A1 | 5/2016 | Kim et al. |
| 2017/0032221 | A1 | 2/2017 | Wu et al. |
| 2017/0156607 | A1 | 6/2017 | Oz et al. |
| 2018/0028144 | A1 | 2/2018 | Chen et al. |
| 2018/0168473 | A1 | 6/2018 | Du et al. |
| 2019/0008475 | A1 | 1/2019 | Datta et al. |
| 2019/0013102 | A1 | 1/2019 | Das et al. |
| 2019/0059747 | A1 | 2/2019 | Kaiser et al. |
| 2019/0059748 | A1 | 2/2019 | Kaiser et al. |
| 2019/0083042 | A1 | 3/2019 | Shute et al. |
| 2019/0192110 | A1 | 6/2019 | Parvaneh et al. |
| 2019/0290145 | A1 | 9/2019 | Zalevsky et al. |
| 2019/0328243 | A1 | 10/2019 | Nemati et al. |
| 2019/0378617 | A1 | 12/2019 | Charles et al. |
| 2020/0037930 | A1 | 2/2020 | Abramoff et al. |
| 2020/0046244 | A1 * | 2/2020 | Alam ..................... G16H 50/20 |
| 2020/0077951 | A1 | 3/2020 | Nallathambi et al. |
| 2020/0093386 | A1 | 3/2020 | Biswas et al. |
| 2020/0107807 | A1 | 4/2020 | Hussain |
| 2020/0107810 | A1 | 4/2020 | Hussain |
| 2020/0163627 | A1 | 5/2020 | Sayadi et al. |
| 2020/0178850 | A1 | 6/2020 | Thakur et al. |
| 2020/0214618 | A1 | 7/2020 | Vullings |
| 2020/0237313 | A1 | 7/2020 | Gill et al. |
| 2020/0245889 | A1 * | 8/2020 | Telenkov ............. A61B 5/6885 |
| 2020/0327985 | A1 | 10/2020 | Du et al. |
| 2020/0335123 | A1 | 10/2020 | Kirsch et al. |
| 2020/0388287 | A1 * | 12/2020 | Anushiravani ........ G16H 20/10 |
| 2021/0030390 | A1 | 2/2021 | Jeevannavar |
| 2021/0090734 | A1 | 3/2021 | Singh et al. |
| 2021/0145306 | A1 | 5/2021 | Karankevich et al. |
| 2021/0186426 | A1 | 6/2021 | Raju et al. |
| 2021/0233554 | A1 | 7/2021 | Buddhadev et al. |
| 2021/0298688 | A1 | 9/2021 | Banerjee et al. |
| 2021/0361227 | A1 | 11/2021 | Chou et al. |

FOREIGN PATENT DOCUMENTS

| | | |
|---|---|---|
| CN | 102271589 A | 12/2011 |
| CN | 105873499 A | 8/2016 |
| CN | 107811649 A | 3/2018 |
| CN | 110363090 A | 10/2019 |
| CN | 110558944 A | 12/2019 |
| CN | 110731778 A | 1/2020 |
| EP | 1389957 A1 | 2/2004 |
| EP | 2197342 B1 | 7/2013 |
| EP | 1915095 B1 | 11/2013 |
| EP | 3219253 A1 | 9/2017 |
| EP | 3330974 A1 | 6/2018 |
| EP | 3424432 A1 | 1/2019 |
| EP | 3539464 A1 | 9/2019 |
| EP | 3591663 A1 | 1/2020 |
| EP | 3270774 B1 | 5/2020 |
| GB | 2560339 B | 6/2020 |
| GB | 2582124 A | 9/2020 |
| KR | 102186157 B1 | 12/2020 |
| WO | 2018186807 A1 | 10/2018 |
| WO | 2019038109 A1 | 2/2019 |
| WO | 2019171021 A1 | 9/2019 |
| WO | 2019229543 A1 | 12/2019 |
| WO | 2020165758 A1 | 8/2020 |

OTHER PUBLICATIONS

Extended European Search Report of European Patent Application Serial No. EP21912168.8, Oct. 14, 2024, 11 pages.

P. Heindel et al., "Predicting Radiocephalic Arteriovenous Fistula Success with Machine Learning," npj Digital Medicine, vol. 5, No. 160, Oct. 25, 2022, 9 pages.

T. W. Secomb et al., "Blood Viscosity in Microvessels: Experiment and Theory," Comptes Rendus Physique, vol. 14, No. 6, Jun.-Jul. 2013, pp. 470-478.

M. J. Lighthill, "On Sound Generated Aerodynamically, I. General Theory," Proceedings of the Royal Society A, vol. 211, No. 1107, Mar. 20, 1952, 24 pages.

K. Abreo et al., "Physical Examination of the Hemodialysis Arteriovenous Fistula to Detect Early Dysfunction," The Journal of Vascular Access, vol. 20, No. 1, Jan. 2019, pp. 7-11.

A. Dosovitskiy et al., "An Image is Worth 16x16 Words Transformers for Image Recognition at Scale," The International Conference on Learning Representations, arXiv:2010.11929v2, Jun. 3, 2021, 22 pages.

T. N. Epperson et al., "Anatomy, Shoulder and Upper Limb, Brachial Artery," StatPearls [Internet], https://www.ncbi.nlm.nih.gov/books/NBK537145/, Jul. 25, 2022, 8 pages.

R. M. Marchese et al., "Anatomy, Shoulder and Upper Limb, Forearm Radial Artery," StatPearls Publishing, https://europepmc.org/article/nbk/nbk546626, Feb. 3, 2023, 6 pages.

M. Loukas et al., "The Clinical Anatomy of the Cephalic Vein in the Deltopectoral Triangle," Folia Morphol, vol. 67, No. 1, Dec. 3, 2007, pp. 72-77.

A. Kiray et al., "Anatomical Evaluation of the Superficial Veins of the Upper Extremity as Graft Donor Source in Microvascular Reconstructions: A Cadaveric Study," Acta Orthopaedica et Traumatologica Turcica, vol. 47, No. 6, Jul. 2, 2014, pp. 405-410.

K. He et al., "Deep Residual Learning for Image Recognition," Proceedings of the IEEE Conference on Computer Vision and Pattern Recognition, arXiv:1512.03385v1, Dec. 10, 2015, 12 pages.

J. Deng et al., "ImageNet: A Large-Scale Hierarchical Image Database," IEEE Conference on Computer Vision and Pattern Recognition, Jun. 2009, 8 pages.

J.-P. Eckmann et al., "Recurrence Plots of Dynamical Systems," Europhysics Letters, vol. 4, No. 9, Nov. 1, 1987, pp. 973-977.

R. Shekhar et al., "Automated Identification of Innocent Still's Murmur Using a Convolutional Neural Network," Frontiers in Pediatrics, Sep. 21, 2022, 10 pages.

M. A. Kotb et al., "Improving the Recognition of Heart Murmur" International Journal of Advanced Computer Science and Applications, Dec. 6, 2015, 10 pages.

A. Gharehbaghi et al., A Hybrid Machine Learning Method for Detecting Cardiac Ejection Murmurs, International Federation for Medical and Biological Engineering Proceedings, Jun. 2018, pp. 787-790.

J.-K. Wang et al., "Automatic Recognition of Murmurs of Ventricular Septal Defect Using Convolutional Recurrent Neural Networks with Temporal Attentive Pooling," Scientific Reports, vol. 10, No. 21797, Dec. 11, 2020, 10 pages.

(56)　　　　　References Cited

OTHER PUBLICATIONS

C. G. Degroff et al., "Artificial Neural Network-Based Method of Screening Heart Murmurs in Children," Circulation, vol. 103, No. 22, Jun. 5, 2001, pp. 2711-2716.

W. Chen et al., "Deep Learning Methods for Heart Sounds Classification: A Systematic Review," Entropy, vol. 23, No. 667, May 26, 2021, 18 pages.

S. Latif et al., "Phonocardiographic Sensing using Deep Learning for Abnormal Heartbeat Detection," arXiv:1801.08322v4, Jul. 28, 2020, 7 pages.

F. A. Khan et al., "Automatic Heart Sound Classification from Segmented/Unsegmented Phonocardiogram Signals Using Time and Frequency Features," Physiological Measurement, Author Manuscript, Apr. 2020, 12 pages.

J. S. Chorba et al., "Deep Learning Algorithm for Automated Cardiac Murmur Detection via a Digital Stethoscope Platform," Journal of the American Heart Association, vol. 10, No. 9, May 4, 2021, 19 pages.

Y. Xu et al., "Pay More Attention With Fewer Parameters: A Novel 1-D Convolutional Neural Network for Heart Sounds Classification," Computing in Cardiology, vol. 45, Sep. 2018, 4 pages.

A. I. Humayun et al., "Towards Domain Invariant Heart Sound Abnormality Detection using Learnable Filterbanks," arXiv:1910.00498v3, Oct. 2, 2020, 10 pages.

S. L. Oh et al., "Classification of Heart Sound Signals Using a Novel Deep WaveNet Model," Computer Methods and Programs in Biomedicine, Jun. 2020, 21 pages.

N. Baghel et al., "Automatic Diagnosis of Multiple Cardiac Diseases from PCG Signals using Convolutional Neural Network," Computer Methods and Programs in Biomedicine, vol. 197, Sep. 2020, 16 pages.

O. Deperlioglu et al., "Diagnosis of Heart Diseases by a Secure Internet of Health Things System Based on Autoencoder Deep Neural Network," Computer Communications, vol. 162, Oct. 1, 2020, pp. 31-50.

S. Sun et al., "A Novel Intelligent System Based on Adjustable Classifier Models for Diagnosing Heart Sounds," Scientific Reports, vol. 12, Jan. 25, 2022, 17 pages.

F. Demir et al., "Towards the Classification of Heart Sounds Based on Convolutional Deep Neural Network," Health Information Science and Systems, vol. 7, No. 16, Aug. 7, 2019, 9 pages.

T. Nilanon et al., "Normal/Abnormal Heart Sound Recordings Classification Using Convolutional Neural Network," Computing in Cardiology, vol. 43, Sep. 2016, 4 pages.

J. P. Dominguez-Morales et al., "Deep Neural Networks for the Recognition and Classification of Heart Murmurs Using Neuromorphic Auditory Sensors," IEEE Transactions on Biomedical Circuits and Systems, vol. 12, No. 1, Feb. 2018, 11 pages.

X. Cheng et al., "Design and Application of a Laconic Heart Sound Neural Network," IEEE Access, vol. 7, Aug. 12, 2019, pp. 124417-124425.

J. Rubin et al., "Classifying Heart Sound Recordings using Deep Convolutional Neural Networks and Mel-Frequency Cepstral Coefficients," Computing in Cardiology Conference, Sep. 2016, 4 pages.

Z. Wang et al., "Encoding Time Series as Images for Visual Inspection and Classification Using Tiled Convolutional Neural Networks," Workshops at the Twenty-Ninth AAAI Conference on Artificial Intelligence, Jan. 2015, 7 pages.

J. Oliveira et al., "The CirCor DigiScope Dataset: From Murmur Detection to Murmur Classification," IEEE Journal of Biomedical and Health Informatics, vol. 26, No. 6, Jun. 2022, pp. 2524-2535.

Z. Tariq et al., "Feature-Based Fusion Using CNN for Lung and Heart Sound Classification," Sensors, vol. 22, No. 4, Feb. 16, 2022, 28 pages.

V. Kudriavtsev et al., "Heart Energy Signature Spectrogram for Cardiovascular Diagnosis," BioMedical Engineering OnLine, vol. 6, No. 16, May 4, 2007, 22 pages.

C. Tuchinda et al., "Cardiac Auscultatory Recording Database: Delivering Heart Sounds Through the Internet," Proceedings of the AMIA Annual Symposium, Nov. 2001, pp. 716-720.

A. M. Menillo et al., "Atrial Septal Defect," StatPearls [Internet], https://www.ncbi.nlm.nih.gov/books/NBK535440/, Aug. 8, 2022, 10 pages.

J. Heaton et al, "Pulmonic Stenosis," StatPearls [Internet], https://www.ncbi.nlm.nih.gov/books/NBK560750/, Jan. 4, 2023, 9 pages.

S. Bhansali et al., "Truncus Arteriosus," StatPearls [Internet], https://www.ncbi.nlm.nih.gov/books/NBK534774/, Aug. 8, 2022, 10 pages.

M. W. Szymanski et al., "Transposition of The Great Arteries," StatPearls [Internet], https://www.ncbi.nlm.nih.gov/books/NBK538434/, Jan. 15, 2023, 8 pages.

A. Konduri et al., "Partial and Total Anomalous Pulmonary Venous Connection," StatPearls [Internet], https://www.ncbi.nlm.nih.gov/books/NBK560707/, Aug. 16, 2022, 9 pages.

C. H. Attenhofer Jost et al., "Ebstein's Anomaly," Circulation, vol. 115, No. 2, Jan. 16, 2007, pp. 277-285.

R. P. Campos et al., "Accuracy of Physical Examination and Intra-Access Pressure in the Detection of Stenosis in Hemodialysis Arteriovenous Fistula," Seminars in Dialysis, vol. 21, No. 3, May 2008, pp. 269-273.

J. Wang et al., "Intelligent Diagnosis of Heart Murmurs in Children with Congenital Heart Disease," Hindawi Journal of Healthcare Engineering, May 11, 2020, 9 pages.

A, K. Viecelli et al., "Report of the Standardized Outcomes in Nephrology-Hemodialysis (SONG-HD) Consensus Workshop on Establishing a Core Outcome Measure for Hemodialysis Vascular Access," American Journal of Kidney Diseases, Feb. 2018, 11 pages.

J. Bonatti et al., "Neointimal Hyperplasia in Coronary Vein Grafts: Pathophysiology and Prevention of a Significant Clinical Problem," The Heart Surgery Forum, #2003-153203, vol. 7, No. 1, Jan. 2004, pp. E72-E87.

E. Kostopoulou et al., "Cardiac Murmurs in Children: A Challenge for the Primary Care Physician," Current Pediatric Reviews, vol. 15, No. 3, Mar. 2019, pp. 131-138.

A. Yadav et al., "Machine Learning-Based Classification of Cardiac Diseases from PCG Recorded Heart Sounds," Neural Computing and Applications, Dec. 2020, vol. 32, No. 24, pp. 17843-17856.

T. Nielsen et al., "The Development of a New Cardiac Auscultation Test: How Do Screening and Diagnostic Skills Differ?" Medical Teacher, vol. 32, No. 1, pp. 56-61.

Children's Hospital of Philadelphia, "Heart Murmur in Children," https://www.chop.edu/conditions-diseases/heart-murmur, Accessed Mar. 19, 2021, 4 pages.

E. Mejia et al., "Innocent Murmur," https://www.ncbi.nlm.nih.gov/books/NBK507849/, Sep. 8, 2020, 7 pages.

I. Haney et al., "Accuracy of Clinical Assessment of Heart Murmurs by Office Based (General Practice) Paediatricians," Archives of Disease in Childhood, vol. 81, No. 5, 1999, pp. 409-412.

A. S. Bensky et al., "Primary Care Physicians' Use of Screening Echocardiography," Pediatrics, vol. 103, No. 4, Apr. 1999, 5 pages.

T. Gokhale, "Machine Learning Based Identification of Pathological Heart Sounds," Computing in Cardiology, vol. 43, Sep. 2016, 4 pages.

M. E. H. Chowdhury et al., "Real-Time Smart-Digital Stethoscope System for Heart Diseases Monitoring," Sensors, Jun. 20, 2019, vol. 19, No. 2781, pp. 1-22.

Y. Chen et al., "Classification of Heart Sounds Based on the Combination of the Modified Frequency Wavelet Transform and Convolutional Neural Network," Medical & Biological Engineering & Computing, Jul. 7, 2020, 9 pages.

J. Acharya et al., "Deep Neural Network for Respiratory Sound Classification in Wearable Devices Enabled by Patient Specific Model Tuning," arXiv:2004.08287v1, Apr. 16, 2020, 10 pages.

S. Dhuper et al., "Improvement of Cardiac Auscultation Skills in Pediatric Residents with Training," Clinical Pediatrics, vol. 46, No. 3, Apr. 2007, pp. 236-240.

D. Juniati et al., "Fractal Dimension to Classify the Heart Sound Recordings with KNN and Fuzzy c-Mean Clustering Methods," The 2nd International Joint Conference on Science and Technology, Journal of Physics Conference Series, 2017, 9 pages.

S.-W. Deng et al., "Towards Heart Sound Classification without Segmentation via Autocorrelation Feature and Diffusion Maps," Future Generation Computer Systems, vol. 60, 2016, pp. 13-21.

(56) References Cited

OTHER PUBLICATIONS

W. Zhang et al., "Heart Sound Classification Based on Scaled Spectrogram and Tensor Decomposition," Expert Systems With Applications, vol. 84, 2017, pp. 220-231.

T.-C. I. Yang et al., "Classification of Acoustic Physiological Signals Based on Deeplearning Neural Networks with Augmented Features," Computing in Cardiology, vol. 43, Sep. 14, 2016, 4 pages.

A. Raza et al., "Heartbeat Sound Signal Classification Using Deep Learning," Sensors, vol. 19, No. 4819, Nov. 5, 2019, 15 pages.

H. Ryu et al., "Classification of Heart Sound Recordings using Convolution Neural Network," Computing in Cardiology, vol. 43, Sep. 14, 2016, 4 pages.

A. Halevy et al., "The Unreasonable Effectiveness of Data," IEEE Intelligent Systems, Mar./Apr. 2009, vol. 24, pp. 8-12.

C. Sun et al., "Revisiting Unreasonable Effectiveness of Data in Deep Learning Era," arXiv:1707.02968v2, Aug. 4, 2017, 13 pages.

C. Shorten et al., "A Survey on Image Data Augmentation for Deep Learning," Journal of Big Data, vol. 6, No. 60, Jul. 6, 2019, 48 pages.

C. Liu et al., "An Open Access Database for the Evaluation of Heart Sound Algorithms," Physiological Measurement, Nov. 2016, 38 pages.

A. L. Goldberger et al., "PhysioBank, PhysioToolkit, and PhysioNet: Components of a New Research Resource for Complex Physiologic Signals," Circulation, vol. 101, No. 23, Jun. 13, 2000, 6 pages.

S. Mcgee, "Auscultation of the Heart: General Principles," Evidence-Based Physical Diagnosis, Elsevier, 2012, pp. 320-324.

A. Krizhevsky et al., "ImageNet Classification with Deep Convolutional Neural Networks," Communications of the ACM, vol. 60, No. 6, Jun. 2017, 9 pages.

W. Zhang et al., "Towards Heart Sound Classification Without Segmentation Using Convolutional Neural Network," Computing in Cardiology, Sep. 14, 2017, 4 pages.

M. Tschannen et al., "Heart Sound Classification Using Deep Structured Features," Computing in Cardiology, Sep. 2016, 4 pages.

B. M. Whitaker et al., "Combining Sparse Coding and Time-Domain Features for Heart Sound Classification," Physiological Measurement, vol. 38, No. 8, Draft, 14 pages.

D. S. Park et al., "SpecAugment: A Simple Data Augmentation Method for Automatic Speech Recognition," arXiv:1904.08779v3, Dec. 3, 2019, 6 pages.

P. R. A. Gaskin et al, "Clinical Auscultation Skills in Pediatric Residents," Pediatrics, vol. 105, No. 6, Jun. 2000, pp. 1184-1187.

T. Geva et al., "Reappraisal of the Approach to the Child with Heart Murmurs: Is Echocardiography Mandatory?" International Journal of Cardiology, vol. 19, No. 1, Apr. 1988, pp. 107-113.

T. John et al., "A Smartphone Stethoscope and Application for Automated Identification of Innocent Still's Murmur," Proceedings of the 2018 Design of Medical Devices Conference, Apr. 2018, 3 pages.

S. Mangione, "Cardiac Auscultatory Skills of Physicians-in-Training: A Comparison of Three English-Speaking Countries," The American Journal of Medicine, vol. 110, No. 3, Feb. 15, 2001, pp. 210-216.

W. Liu et al., "Additive White Gaussian Noise Level Estimation in SVD Domain for Images," IEEE Transactions on Image Processing, vol. 22, No. 3, Mar. 2013, pp. 872-883.

G. Zhou et al., "On the Analysis of Data Augmentation Methods for Spectral Imaged Based Heart Sound Classification Using Convolutional Neural Networks," https://doi.org/10.21203/rs.3.rs-888104/v1, Sep. 20, 2021, 34 pages.

G. Zhou et al., "On the Analysis of Data Augmentation Methods for Spectral Imaged Based Heart Sound Classification Using Convolutional Neural Networks," BMC Medical Informatics and Decision Making, vol. 22, No. 226, Aug. 29, 2022, 21 pages.

N. Gjorgjievski et al., "Primary Failure of the Arteriovenous Fistula in Patients with Chronic Kidney Disease Stage 4/5," Macedonian Journal of Medical Sciences, vol. 7, No. 11, Jun. 15, 2019, pp. 1782-1787.

J. Gameiro et al., "Factors Affecting Arteriovenous Fistula Dysfunction: A Narrative Review," The Journal of Vascular Access, vol. 21, No. 2, May 22, 2019, 14 pages.

H. Hu et al., "Future Research Directions to Improve Fistula Maturation and Reduce Access Failure," Seminars in Vascular Surgery, vol. 29, No. 4, Dec. 2016, pp. 153-171.

R. Stolic, "Most Important Chronic Complications of Arteriovenous Fistulas for Hemodialysis," Medical Principles and Practice, vol. 22, No. 3, Mar. 2013, pp. 220-228.

L. Turmel-Rodrigues et al., "Treatment of Failed Native Arteriovenous Fistulae for Hemodialysis by Interventional Radiology," Kidney International, vol. 57, No. 3, Mar. 2000, pp. 1124-1140.

R. Stolic et al., "Early Pathohistological Changes in Dysfunction of Arteriovenous Fistula for Hemodialysis," Vojnosanitetski Pregled, vol. 67, No. 1, Jan. 2010, pp. 65-68. [Article in Serbian].

R. J. Nordyke et al., "Costs Attributable to Arteriovenous Fistula and Arteriovenous Graft Placements in Hemodialysis Patients with Medicare Coverage," American Journal of Nephrology, vol. 50, No. 4, Aug. 21, 2019, pp. 320-328.

M. Thamer et al., "Medicare Costs Associated with Arteriovenous Fistulas Among US Hemodialysis Patients," American Journal of Kidney Diseases, vol. 72, No. 1, Jul. 2018, pp. 10-18.

C. E. Lok et al., "Vascular Access Morbidity and Mortality: Trends of the Last Decade," Clinical Journal of the American Society of Nephrology, vol. 8, No. 7, Jul. 2013, pp. 1213-1219.

R. P. Campos et al., "Stenosis in Hemodialysis Arteriovenous Fistula: Evaluation and Treatment," Hemodialysis International, vol. 10, No. 2, Apr. 2006, pp. 152-161.

C. E. Lok et al., "KDOQI Clinical Practice Guideline for Vascular Access: 2019 Update," American Journal of Kidney Diseases, vol. 75, No. 4, Supplement 2, Apr. 2020, pp. S1-S164.

K. E. Chan et al., "Access Survival Amongst Hemodialysis Patients Referred for Preventive Angiography and Percutaneous Transluminal Angioplasty," Clinical Journal of the American Society of Nephrology, vol. 6, No. 11, Nov. 2011, pp. 2669-2680.

N. Tessitore et al., "Should Current Criteria for Detecting and Repairing Arteriovenous Fistula Stenosis Be Reconsidered? Interim Analysis of a Randomized Controlled Trial," Nephrology Dialysis Transplantation, vol. 29, No. 1, Jan. 2014, pp. 179-187.

A. A. Al-Jaishi et al., "Complications of the Arteriovenous Fistula: A Systematic Review," Journal of the American Society of Nephrology, vol. 28, No. 6, Jun. 2017, pp. 1839-1850.

J. Hoggard et al, "Guidelines for Venous Access in Patients with Chronic Kidney Disease. A Position Statement from the American Society of Diagnostic and Interventional Nephrology," Seminars in Dialysis, vol. 21, No. 2, Mar. 2008, pp. 186-191.

H. Hafke-Dys et al., "The Accuracy of Lung Auscultation in the Practice of Physicians and Medical Students," PLOS One, Aug. 12, 2019, 9 pages.

R. Peralta et al., "Development and Validation of a Machine Learning Model Predicting Arteriovenous Fistula Failure in a Large Network of Dialysis Clinics," International Journal of Environmental Research and Public Health, vol. 18, No. 23, Nov. 24, 2021, 12 pages.

International Search Report and Written Opinion of PCT/US2021/064926 dated Mar. 24, 2022, 10 pages.

D. M. Nogueira et al., "Classifying Heart Sounds Using Images of Motifs, MFCC and Temporal Features," Journal of Medical Systems, vol. 43, No. 6, May 6, 2019, 13 pages.

M. Hamidi et al., "Classification of Heart Sound Signal Using Curve Fitting and Fractal Dimension," Biomedical Signal Processing and Control, vol. 39, Jan. 2018, pp. 351-359.

V. Maknickas et al., "Recognition of Normal-Abnormal Phonocardiographic Signals Using Deep Convolutional Neural Networks and Mel-Frequency Spectral Coefficients," Physiological Measurement, vol. 38, No. 8, Jul. 31, 2017, pp. 1671-1684.

M. E. Karar et al., "Automated Diagnosis of Heart Sounds Using Rule-Based Classification Tree," Journal of Medical Systems, vol. 41, No. 60, Mar. 1, 2017, 7 pages.

X. Cheng et al., "A High Recognition Rate of Feature Extraction Algorithm Without Segmentation," IEEE 6th International Conference on Industrial Engineering and Applications (ICIEA), Apr. 2019, pp. 923-927.

(56)

References Cited

OTHER PUBLICATIONS

P. Wang et al., "Phonocardiographic Signal Analysis Method Using a Modified Hidden Markov Model," Annals of Biomedical Engineering, vol. 35, No. 3, Mar. 2007, pp. 367-374.

S. Chauhan et al., "A Computer-Aided MFCC-Based HMM System for Automatic Auscultation," Computers in Biology and Medicine, vol. 38, No. 2, Feb. 2008, pp. 221-233.

B. Bozhurt et al., "A Study of Time-Frequency Features for CNN-Based Automatic Heart Sound Classification for Pathology Detection," Computers in Biology and Medicine, vol. 100, No. 1, Sep. 2018, pp. 132-143.

S. Kang et al., "Automated Identification of Innocent Still's Murmur in Children," IEEE Transactions on Biomedical Engineering, vol. 64, No. 6, Jun. 2017, pp. 1326-1334.

G. Saravanan et al., "Real Time Implementation of RGB to HSV/HSI/HSL and Its Reverse Color Space Models," International Conference on Communication and Signal Processing, Apr. 2016, 5 pages.

J. Shijie et al., "Research on Data Augmentation for Image Classification Based on Convolution Neural Networks," Chinese Automation Congress (CAC), Oct. 2017, pp. 4165-4170.

M. Fokou et al., "Complications of Arteriovenous Fistula for Hemodialysis: An 8-Year Study," Annals of Vascular Surgery, vol. 26, No. 5, Jul. 2012, pp. 680-684.

C. Mercado et al., "Early and Late Fistula Failure," Clinical Nephrology, vol. 69, No. 2, Feb. 2008, pp. 77-83.

J. H. W. Lee et al., "Turbulent Jets and Plumes: A Lagrangian Approach," Kluwer Academic Publishers, 2003, 390 pages.

B. W. Mccrindle et al., "Factors Prompting Referral for Cardiology Evaluation of Heart Murmurs in Children," Archives of Pediatrics and Adolescent Medicine, vol. 149, No. 11, Nov. 1995, pp. 1277-1279.

K. Kumar et al., "Evaluation of Cardiac Auscultation Skills in Pediatric Residents," Clinical Pediatrics, vol. 52, No. 1, Jan. 2013, pp. 66-73.

J. Wen et al., "Prevalence of Innocent Murmurs in Pediatric Patients," Pediatrics, Aug. 2019, Abstract Only.

E. Pretorius et al., "Development of a Pediatric Cardiac Computer Aided Auscultation Decision Support System," 32nd Annual International Conference of the IEEE EMBS, Aug.-Sep. 2010, pp. 6078-6082.

B. Xiao et al., "Follow the Sound of Children's Heart: A Deep-Learning-Based Computer-Aided Pediatric CHDs Diagnosis System," IEEE Internet of Things Journal, vol. 7, No. 3, Mar. 2020, pp. 1994-2004.

J. Liu et al., "Deep Learning-Based Computer-Aided Heart Sound Analysis in Children with Left-to-Right Shunt Congenital Heart Disease," International Journal of Cardiology, vol. 348, Feb. 1, 2022, pp. 58-64.

B. Xiao et al., "Heart Sounds Classification Using a Novel 1-D Convolutional Neural Network with Extremely Low Parameter Consumption," Neurocomputing, vol. 392, Jun. 7, 2020, pp. 153-159.

T. Alafif et al., "Normal and Abnormal Heart Rates Recognition Using Transfer Learning," 12th International Conference on Knowledge and Systems Engineering (KSE), Nov. 2020, pp. 275-280.

X. Huai et al., "Heart Sound Recognition Technology Based on Convolutional Neural Network," Informatics for Health and Social Care, vol. 46, No. 3, Apr. 4, 2021, pp. 320-332.

J. F. Keane et al., "Pulmonary Stenosis," Chapter 31 in Nadas' Pediatric Cardiology, Jun. 15, 2006, Preview Only.

M. J. Lighthill, "On Sound Generated Aerodynamically II. Turbulence as a Source of Sound," Proceedings of the Royal Society A, Feb. 23, 1954. Abstract Only.

* cited by examiner

MEL-SCALED, dB-SCALED SPECTROGRAM

SPECTROGRAM ON A LINEAR SCALE

UNALTERED MEL-SPECTROGRAM

HORIZONTALLY FLIPPED MEL-SPECTROGRAM        VERTICALLY FLIPPED MEL-SPECTROGRAM

600

1st CONVOLUTION LAYER — 602

1st MAX POOLING LAYER — 604

2nd CONVOLUTION LAYER — 606

2nd MAX POOLING LAYER — 608

FULLY CONNECTED LAYER — 610

SOFTMAX LAYER — 612

NORMAL PEDIATRIC HEART SOUND

SPECTROGRAM IMAGE REPRESENTATION

RECURRENCE PLOT IMAGE REPRESENTATION

VENTRAL SEPTAL DEFECT PEDIATRIC HEART SOUND

SPECTROGRAM IMAGE REPRESENTATION

RECURRENCE PLOT IMAGE REPRESENTATION a. Normal

Mel-spectrogram          Markov transition field          Gramian angular field b. Still's Murmur

Mel-spectrogram          Markov transition field          Gramian angular field c. Mitral Regurgitation
*Mel-spectrogram*          *Markov transition field*          *Gramian angular field* d. Tetralogy of Fallot
*Mel-spectrogram*          *Markov transition field*          *Gramian angular field*

CLASSIFYING BIOMEDICAL ACOUSTICS BASED ON IMAGE REPRESENTATION

RELATED APPLICATIONS

The present application is a continuation-in-part of PCT International Application No. PCT/US2021/064926, filed Dec. 22, 2021 and entitled "Classifying Biomedical Acoustics Based on Image Representation," which is incorporated by reference herein in its entirety, and which claims priority to and fully incorporates by reference U.S. Provisional Patent Application Ser. No. 63/129,179, filed Dec. 22, 2020, also incorporated by reference herein in its entirety.

FIELD

The field relates generally to information processing systems, and more particularly to machine learning and other types of artificial intelligence implemented in such systems.

BACKGROUND

Many emergent medical conditions have specific and reproducible physical exam findings. Sounds produced by the human body contain a rich amount of information that reflect the underlying pathophysiology. For example, sounds produced by the heart reflect its underlying biology, and can cue a trained physician to differentiate between heart pathologies such as valvular defects or congenital diseases. Thus, auscultation has long been a core element of the physical exam. However, relevant audio cues can be missed by even the most seasoned clinicians, and the decline in accurate auscultation is a well-documented phenomenon. In recent years, cardiac auscultation has been challenged for its diagnostic utility, as internal medicine residents in the US made a correct assessment of auscultation findings only 22% of the time. This is observed across many different medical disciplines. A need therefore exists for improved techniques for accurate and efficient point-of-care diagnosis, and more generally for improvements in analysis of medical sounds and other biomedical acoustics.

SUMMARY

Illustrative embodiments disclosed herein implement biomedical acoustics classifiers based on image representations of acoustic signals. For example, some embodiments provide systems implementing techniques for classifying various biomedical acoustics such as heart sounds, blood flow sounds, lung sounds, bowel sounds, cough sounds, and/or other physiological sounds based on their respective image representations. Such techniques are highly accurate and efficient, and provide substantial improvements relative to conventional approaches, in a wide variety of different medical contexts as well as other processing contexts.

One or more such embodiments illustratively further provide various types of automated remediation responsive to classifications generated by a biomedical acoustics classifier. For example, some embodiments implement classification and remediation algorithms to at least partially automate various aspects of patient care in healthcare applications such as telemedicine. Such applications can involve a wide variety of different types of remote medical monitoring and intervention.

In an illustrative embodiment, a method comprises obtaining an acoustic signal for a given individual, generating an image representation of at least a portion of the acoustic signal, processing the image representation in at least one neural network of an acoustics classifier to generate a classification for the acoustic signal, and executing at least one automated action based at least in part on the generated classification. The automated action may comprise, for example, a remedial action, or another type of action.

The acoustic signal illustratively comprises, for example, at least one of a heart sound signal, a blood flow sound signal, a lung sound signal, a bowel sound signal, a cough sound signal, a nerve conduction sound signal, a neuronal cell firing sound signal, a muscle cell contraction sound signal, a subcutaneous emphysema sound signal, and/or another physiological sound of the given individual. Other types of acoustic signals characterizing one or more biomedical conditions of the given individual may be used.

In some embodiments, generating the image representation illustratively comprises generating at least one spectrogram, with each such spectrogram representing frequency, time and amplitude in respective dimensions thereof.

Other types of image representations can be used in other embodiments. For example, some embodiments disclosed herein utilize recurrence plots, Markov transition field image representations and/or Gramian angular field image representations in addition to or in place of spectrograms.

Additional image representations can be generated using image data augmentation techniques including but not limited to geometric transformations, color-space transformations, masking, kernel filters, and/or other techniques not available at the audio signal level, to expand a training set for processing by a neural network.

In some embodiments, executing at least one automated action based at least in part on the generated classification illustratively comprises generating at least one output signal in a telemedicine application. For example, such output signals in a telemedicine application can comprise classification information for presentation on a user terminal or other display device, classification information transmitted over a network to a medical professional, and/or classification information transmitted over a network to a prescription-filling entity. A wide variety of other signals can be generated in conjunction with execution of one or more automated actions in illustrative embodiments.

It is to be appreciated that the foregoing arrangements are only examples, and numerous alternative arrangements are possible.

These and other illustrative embodiments include but are not limited to systems, methods, apparatus, processing devices, integrated circuits, and computer program products comprising processor-readable storage media having software program code embodied therein.

DETAILED DESCRIPTION

Figure 1:
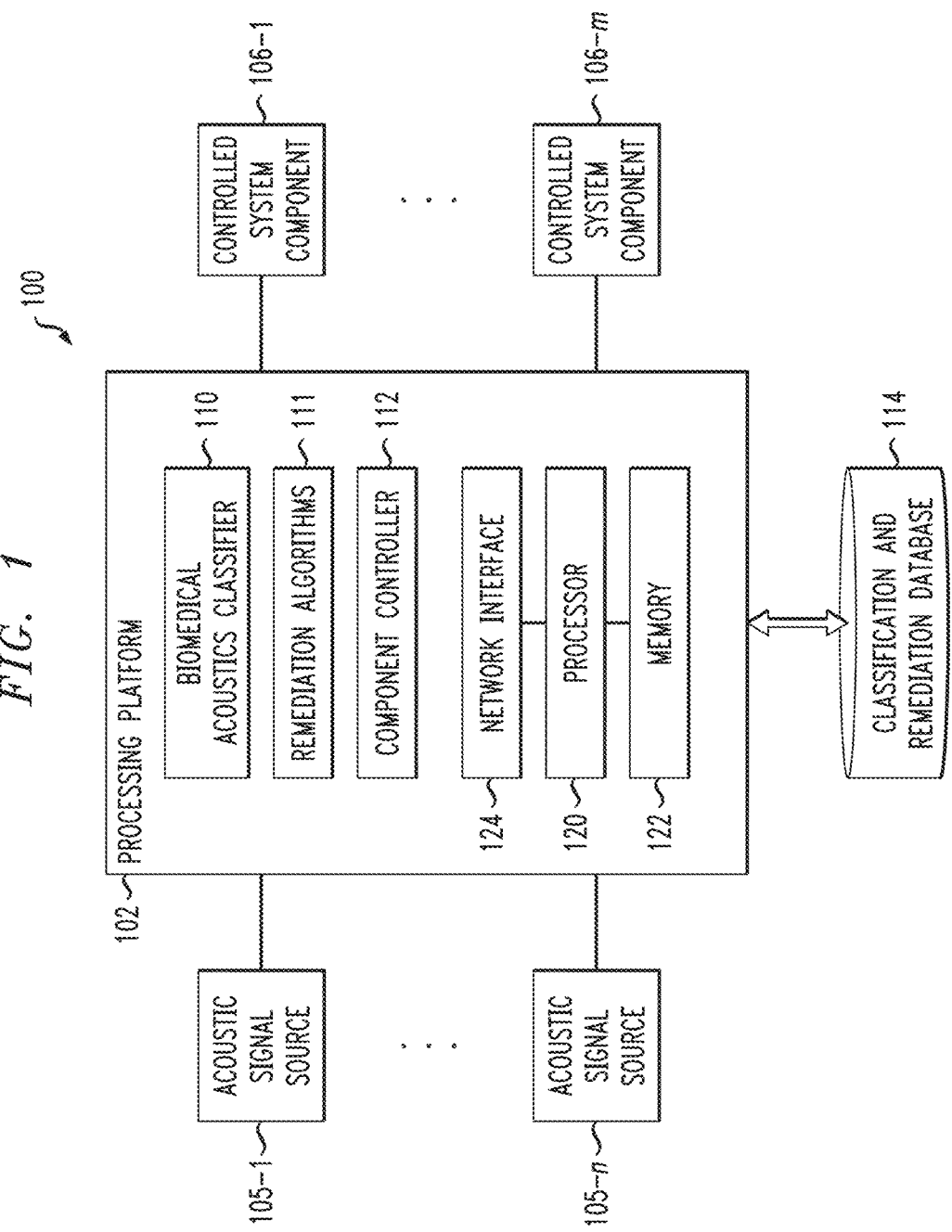
FIG. 1 shows an information processing system comprising a processing platform implementing functionality for biomedical acoustics classification based on image representation in an illustrative embodiment.

Illustrative embodiments can be implemented, for example, in the form of information processing systems comprising one or more processing platforms each having at least one computer, server or other processing device. A number of examples of such systems will be described in detail herein. It should be understood, however, that embodiments of the invention are more generally applicable to a wide variety of other types of information processing systems and associated computers, servers or other processing devices or other components. Accordingly, the term "information processing system" as used herein is intended to be broadly construed so as to encompass these and other arrangements.

The need for accurate and efficient point-of-care diagnosis has spurred an active area of research in developing suitable machine learning models to classify physical exam findings. Audio signals are of particular interest, because they are easily acquired and relatively inexpensive to obtain.

Many of the current methods of sound classification depend on comparing novel recordings against a standardized control. The reliance on statistically significant differences between pathological and normal is a severe limitation on the robustness of automated classification. There are stringent requirements on the purity of the recording, and any extraneous noises, recording artifacts and signal complexity can drastically reduce prediction performance. A natural solution to the convoluted nature of medical signal analysis is deep learning, which maintains the capacity for multiclass labeling, is not reliant on hand-picked features and is more resistant to random variances between samples. Cardiac and lung sound classification using deep learning are two applications that are extensively explored. These sounds are often rhythmic, predictable, and present with distinctive patterns of abnormality. Furthermore, the prevalence of cardiovascular and pulmonary diseases make them high-yield, high-impact targets for automation.

Existing methods of automated heart sound classification typically utilize three steps: segmentation, feature extraction, and classification. Segmentation is the process of identifying the positions and boundaries of S1, S2, systole, and diastole in the cardiac cycle, where S1 and S2 denote respective first and second heart sounds. The subsequent feature extraction and classification steps in the current state-of-the-art methods are reliant on an accurate segmentation step.

However, segmentation has proven to be a challenging task that has limited many heart sound classification algorithms, which has prevented their adoption in real-world, clinical settings. Even an algorithm with a theoretically perfect classification step will only be as accurate as the segmentation step.

A major shortcoming with many existing segmentation methods proposed in literature is that the methods depend on a priori information. For example, one popular method, Shannon-energy-envelope based heart sound segmentation, computes the average Shannon energy of a heart signal using a sliding window to extract the heart sound envelope. Thresholding is used to generate a list of sound lobes that are S1 and S2 candidates. The determination of whether a lobe is S1 or S2 is based on the apriori information that the diastolic period (from S2 to S1) is longer in duration compared to systole (from S1 to S2). From this example, one can quickly see how this algorithm will be unable to handle any cardiac sounds in addition to S1 or S2. If there is an S3 or S4 sound, or the presence of a systolic ejection click (e.g., bicuspid aortic valve), a midsystolic click (e.g., mitral valve prolapse), an opening snap (e.g., mitral stenosis), or a pericardial knock (e.g., constrictive pericarditis) among other possible sounds, their segmentation algorithm will produce additional lobes that become candidates for S1 and S2, leading to erroneous segmentation results. Many other methods also cannot be generalized past identifying S1 and S2. In other words, their segmentation algorithm performs well if the patient is healthy and has a normal heart sound, but will fail for patients that have additional sounds like S3, S4, midsystolic clicks, opening snaps etc. Yet, it is this exact patient demographic that this technology screens for.

The reliance on the a priori information that diastole is longer in duration than systole is not specific to envelope and thresholding methods, but is the basis for many of the published segmentation methods. Even for more robust segmentation algorithms designed to handle S3, S4 etc., those algorithms are still designed around the critical assumption that diastole is longer than systole. This is a problematic assumption because this is not always true. It is known that as heart rate increases, the duration of diastole shortens, becoming comparable to that of systole. Two important patient populations that have increased heart rates are patients with tachycardia and children.

One existing segmentation method addresses these issues by incorporating electrocardiogram (ECG) data. Electrical data from the heart is correlated with the phonocardiogram to determine S1 and S2. However, this has limited real-world, clinical applicability because ECG data is not routinely recorded. The requirement of ECG data for these types of algorithms to work turns auscultation from an easy, rapid screening test to a much more cumbersome task.

Accordingly, conventional segmentation methods suffer from the limitations of relying on apriori information, whether that is in the form of an assumption that diastole is longer in duration than systole, or concurrent ECG data. Moreover, the issue of split S2 sounds, which can be physiologic (e.g., the closure of the aortic valve and pulmonary valve are not synchronized during inspiration) or pathologic (e.g., pulmonic stenosis, right/left bundle branch block, atrial septal defect) is a possibility that has yet to be addressed by any segmentation algorithm. Segmentation has been a rate limiting step that has slowed the uptake of heart classification algorithms in the clinical setting.

With regards to lung sound classification, the ability to identify distinctive characteristics from the signal is the main limitation on model accuracy. Based on a survey of existing computer-based lung-sound analysis methods, features that are most commonly extracted include autoregressive (AR) model, Mel-frequency cepstral coefficient (MFCC), energy, entropy, spectral features, and wavelet. Machine-learning techniques that are most frequently used in prior studies are ANN and k-nearest neighbor algorithms. Other common iterations include GMM, HMM, Fuzzy and GA. Unfortunately, these and other known techniques are unable to satisfy the need for accurate and efficient classification.

Illustrative embodiments disclosed herein overcome the above-noted drawbacks of conventional approaches, at least in part by analyzing medical sounds and other biomedical acoustics based on their image representations. Such an approach advantageously circumvents the above-noted issues associated with segmentation by completely negating the need for it in the first place. Furthermore, an integral input to the model in some embodiments is visual information on the time-frequency domain, which can facilitate accurate and efficient classification of biomedical acoustics in those embodiments.

Some embodiments disclosed herein providing biomedical acoustics classification using deep learning based on image representations can be further generalized to other areas of medical diagnostics. Additional examples of use cases include a broad spectrum of audio signals physicians may obtain as part of the initial screening, or with point-of-care tools that are becoming increasingly common at the bedside. For instance, bowel sound auscultation is an assessment that currently suffers from low accuracy and low inter-observer agreement. However, there is potential for correlating the sounds that are present to normal gastrointestinal motility, small bowel obstruction, or postoperative ileus at the physical exam stage, using the techniques disclosed herein.

Similarly, some embodiments herein are configured to use machine learning to identify asymptomatic Covid-19 cough from regular cough sounds, or classification of pneumonia versus asthma in a pediatric population. Additionally, outside of traditional cough or lung sounds, some embodiments can use audible percussion signals to identify pulmonary injuries such as pneumothorax.

Examples of such illustrative embodiments will be described in detail below with reference to FIGS. 1 through 17.

FIG. 1 shows an information processing system 100 implementing a biomedical acoustics classifier adapted to classify acoustic signals in one or more designated physiological contexts, such as patient diagnosis. The system 100 comprises a processing platform 102. Coupled to the processing platform 102 are acoustic signal sources 105-1, . . . 105-n and controlled system components 106-1, . . . 106-m, where n and m are arbitrary integers greater than or equal to one and may but need not be equal.

Accordingly, some embodiments can include only a single acoustic signal source and/or only a single controlled system component. For example, the acoustic signal source can comprise a transducer of an intelligent stethoscope, with the processing platform 102 being deployed internal to the intelligent stethoscope to receive an acoustic signal from the transducer, and the controlled system component comprising an alert or notification generator or other information display of the intelligent stethoscope. Numerous alternative arrangements are possible.

The processing platform 102 implements at least one biomedical acoustics classifier 110, multiple remediation algorithms 111, and at least one component controller 112. The biomedical acoustics classifier 110 in the present embodiment more particularly implements a neural network based classification algorithm using image representations of acoustic signals, although other arrangements are possible.

In operation, the processing platform 102 is illustratively configured to obtain an acoustic signal for a given individual, such as a patient undergoing diagnosis or treatment, to generate an image representation of at least a portion of the acoustic signal, to process the image representation in at least one neural network of the biomedical acoustics classifier 110 to generate a classification for the acoustic signal, and to execute under the control of the remediation algorithms 111 at least one automated remedial action based at least in part on the generated classification, illustratively via the component controller 112.

Different ones of the remediation algorithms 111 are illustratively configured to provide different automated remedial actions for different classification outcomes. For example, some embodiments active different ones of the controlled system components in different ways via the component controller 112 based on different classification outcomes generated by the biomedical acoustics classifier 110.

The term "remedial action" as used herein is intended to be broadly construed, so as to encompass any type of action that attempts to address, correct or otherwise respond to a particular classification outcome. For example, a remedial action may involve presenting information associated with the classification outcome to a medical professional for use in diagnosing a patient. As another example, a remedial action may comprise generating an alert and sending such an alert over a network. A wide variety of other types of remedial actions can be performed. Also, other types of automated actions not necessarily involving remediation can be performed responsive to particular classification outcome.

In some embodiments, the acoustic signal sources 105 can comprise, for example, one or more internal devices of the given individual, one or more wearable devices of the given individual, a smartphone of the given individual, and/or one or more other types of sensors associated with the given individual.

The generated classification can comprise, for example, an indicator of a particular detected physiological condition of the given individual, although a wide variety of other types of classifications can be generating using the biomedical acoustics classifier 110 in other embodiments.

An acoustic signal applied to the processing platform 102 illustratively comprises, for example, at least one of a heart sound signal, a blood flow sound signal, a lung sound signal, a bowel sound signal, a cough sound signal, a nerve conduction sound signal, a neuronal cell firing sound signal, a muscle cell contraction sound signal, a subcutaneous emphysema sound signal, and/or another physiological sound of the given individual. Other types of acoustic signals characterizing one or more physiological conditions or other biomedical conditions of the given individual may be used.

In some embodiments, generating the image representation illustratively comprises generating at least one spectrogram, with each such spectrogram representing frequency, time and amplitude in respective dimensions thereof. Other types of image representations can be used in other embodiments. For example, some embodiments disclosed herein utilize recurrence plots in addition to or in place of spectrograms. As further examples, additional image representations can be generated using image data augmentation techniques including but not limited to geometric transformations, color-space transformations, masking, kernel filters, and/or other techniques not available at the audio signal level, to expand a training set for processing by a neural network. Such data augmentation techniques can be applied to spectrograms, recurrence plots, or other types of image representations.

Additional details regarding generation and processing of spectrograms, recurrence plots or other types of image representations in the biomedical acoustics classifier 110 will be described elsewhere herein.

Numerous other arrangements of system components and associated generated classifications are possible.

It is to be appreciated that the term "biomedical acoustics classifier" as used herein is intended to be broadly construed to encompass a wide variety of different types of processor-based classification algorithms. Such a classifier is executed by at least one processing device comprising a processor coupled to a memory.

The component controller 112 generates one or more control signals for adjusting, triggering or otherwise controlling various operating parameters associated with the controlled system components 106 based at least in part on classifications generated by the biomedical acoustics classifier 110 and processed by one or more of the remediation algorithms 111. A wide variety of different type of devices or other components can be controlled by component controller 112, possibly by applying control signals or other signals or information thereto, including additional or alternative components that are part of the same processing device or set of processing devices that implement the processing platform 102. Such control signals, and additionally or alternatively other types of signals and/or information, can be communicated over one or more networks to other processing devices, such as user terminals associated with respective system users.

The processing platform 102 is configured to utilize a classification and remediation database 114. Such a database illustratively stores user data, user profiles and a wide variety of other types of information, including data from one or more of the acoustic signal sources 105, that may be utilized by the biomedical acoustics classifier 110 in performing classification and remediation operations. The classification and remediation database 114 is also configured to store related information, including various processing results, such as classifications or other outputs generated by the biomedical acoustics classifier 110.

The component controller 112 utilizes outputs generated by the biomedical acoustics classifier 110 and/or one or more of the remediation algorithms 111 to control one or more of the controlled system components 106. The controlled system components 106 in some embodiments therefore comprise system components that are driven at least in part by outputs generated by the biomedical acoustics classifier 110. For example, a controlled component can comprise a processing device such as a computer, a smartphone, a wearable device, an internal device, an intelligent stethoscope, a handheld sensor device or other type of processing device that presents a display to a user and/or directs a user to respond in a particular manner responsive to an output of classification algorithm. These and numerous other different types of controlled system components 106 can make use of outputs generated by the biomedical acoustics classifier 110, including various types of equipment and other systems associated with one or more of the example use cases described elsewhere herein.

Although the biomedical acoustics classifier 110, remediation algorithms 111 and the component controller 112 are all shown as being implemented on processing platform 102 in the present embodiment, this is by way of illustrative example only. In other embodiments, the biomedical acoustics classifier 110, remediation algorithms 111 and the component controller 112 can each be implemented on a separate processing platform, or using other arrangements. A given such processing platform is assumed to include at least one processing device comprising a processor coupled to a memory.

Examples of such processing devices include computers, servers or other processing devices arranged to communicate over a network. Storage devices such as storage arrays or cloud-based storage systems used for implementation of classification and remediation database 114 are also considered "processing devices" as that term is broadly used herein.

The network can comprise, for example, a global computer network such as the Internet, a wide area network (WAN), a local area network (LAN), a satellite network, a telephone or cable network, a cellular network such as a 3G, 4G or 5G network, a wireless network implemented using a wireless protocol such as Bluetooth, WiFi or WiMAX, or various portions or combinations of these and other types of communication networks.

It is also possible that at least portions of other system elements such as one or more of the acoustic signal sources 105 and/or the controlled system components 106 can be implemented as part of the processing platform 102, although shown as being separate from the processing platform 102 in the figure.

For example, in some embodiments, the system 100 can comprise a laptop computer, tablet computer or desktop personal computer, a smartphone, a wearable device, an internal device, an intelligent stethoscope, a handheld sensor device, or another type of computer or communication device, as well as combinations of multiple such processing devices, configured to incorporate at least one acoustic signal source and to execute a classification algorithm for controlling at least one system component.

Examples of automated remedial actions that may be taken in the processing platform 102 responsive to outputs generated by the biomedical acoustics classifier 110 and/or the remediation algorithms 111 include generating in the component controller 112 at least one control signal for controlling at least one of the controlled system components 106 over a network, generating at least a portion of at least one output display for presentation on at least one user terminal, generating an alert for delivery to at least user terminal over a network, and/or storing the outputs in the classification and remediation database 114.

A wide variety of additional or alternative automated remedial actions may be taken in other embodiments. The particular automated remedial action or actions will tend to vary depending upon the particular use case in which the system 100 is deployed. Other types of automated actions can be performed in other embodiments.

For example, some embodiments implement classification and remediation algorithms to at least partially automate various aspects of patient care in healthcare applications such as telemedicine. Such applications illustratively involve a wide variety of different types of remote medical monitoring and intervention.

An example of an automated remedial action in this particular context includes generating at least one output signal, illustratively comprising at least one of classification information for presentation on a user terminal or other display device, classification information transmitted over a network to a medical professional, and/or classification information transmitted over a network to a pharmacy or other prescription-filling entity. Such classification information can comprise, for example, a classification visualization signal or other type of signal suitable for presentation on a display device.

Additional examples of such use cases are provided elsewhere herein. It is to be appreciated that the term "automated remedial action" as used herein is intended to be broadly construed, so as to encompass the above-described automated remedial actions, as well as numerous other actions that are automatically driven based at least in part on one or more classifications generated using a classification algorithm as disclosed herein, with such actions being configured to address or otherwise remediate various conditions indicated by the corresponding classifications.

The processing platform 102 in the present embodiment further comprises a processor 120, a memory 122 and a network interface 124. The processor 120 is assumed to be operatively coupled to the memory 122 and to the network interface 124 as illustrated by the interconnections shown in the figure.

The processor 120 may comprise, for example, a microprocessor, an application-specific integrated circuit (ASIC), a field-programmable gate array (FPGA), a central processing unit (CPU), a tensor processing unit (TPU), a graphics processing unit (GPU), an arithmetic logic unit (ALU), a digital signal processor (DSP), or other similar processing device component, as well as other types and arrangements of processing circuitry, in any combination. At least a portion of the functionality of at least one neural network or associated classification and/or remediation algorithm provided by one or more processing devices as disclosed herein can be implemented using such circuitry.

In some embodiments, the processor 120 comprises one or more graphics processor integrated circuits. Such graphics processor integrated circuits are illustratively implemented in the form of one or more GPUs. Accordingly, in some embodiments, system 100 is configured to include a GPU-based processing platform. Such a GPU-based processing platform can be cloud-based configured to implement one or more biomedical acoustics classifiers for processing data associated with a large number of system users. Other embodiments can be implemented using similar arrangements of one or more TPUs.

Numerous other arrangements are possible. For example, in some embodiments, one or more neural networks and associated classification algorithms can be implemented on a single processor-based device, such as a computer, a smartphone, a wearable device, an internal device, an intelligent stethoscope, a handheld sensor device or other processing device, utilizing one or more processors of that device. Such embodiments are also referred to herein as "on-device" implementations of classification algorithms.

The memory 122 stores software program code for execution by the processor 120 in implementing portions of the functionality of the processing platform 102. For example, at least portions of the functionality of biomedical acoustics classifier 110, remediation algorithms 111 and/or component controller 112 can be implemented using program code stored in memory 122.

A given such memory that stores such program code for execution by a corresponding processor is an example of what is more generally referred to herein as a processor-readable storage medium having program code embodied therein, and may comprise, for example, electronic memory such as SRAM, DRAM or other types of random access memory, flash memory, read-only memory (ROM), magnetic memory, optical memory, or other types of storage devices in any combination.

Articles of manufacture comprising such processor-readable storage media are considered embodiments of the invention. The term "article of manufacture" as used herein should be understood to exclude transitory, propagating signals.

Other types of computer program products comprising processor-readable storage media can be implemented in other embodiments.

In addition, illustrative embodiments may be implemented in the form of integrated circuits comprising processing circuitry configured to implement processing operations associated with one or more of the biomedical acoustics classifier 110, the remediation algorithms 111 and the component controller 112 as well as other related functionality. For example, at least a portion of the biomedical acoustics classifier 110 of system 100 is illustratively implemented in at least one neural network integrated circuit of a processing device of the processing platform 102.

The network interface 124 is configured to allow the processing platform 102 to communicate over one or more networks with other system elements, and may comprise one or more conventional transceivers.

It is to be appreciated that the particular arrangement of components and other system elements shown in FIG. 1 is presented by way of illustrative example only, and numerous alternative embodiments are possible. For example, other embodiments of information processing systems can be configured to implement classification algorithm and remediation algorithm functionality of the type disclosed herein.

Also, terms such as "acoustic signal source" and "controlled system component" as used herein are intended to be broadly construed. For example, a given set of acoustic signal sources in some embodiments can comprise one or more internal devices of an individual, one or more wearable devices of the individual, a smartphone of the individual, and/or one or more other types of sensors associated with the individual.

Additionally or alternatively, acoustic signal sources can comprise intelligent stethoscopes, electrodes, video cameras, sensor arrays or other types of imaging or data capture devices. Other examples of acoustic signal sources include various types of databases or other storage systems accessible over a network, where such databases store acoustic signals and other related data. A wide variety of different types of acoustic signal sources can therefore be used to provide input data to a classification algorithm in illustrative embodiments. A given controlled component can illustratively comprise a computer, a smartphone, a wearable device, an internal device, an intelligent stethoscope, a handheld sensor device or other type of processing device that receives an output from a classification algorithm and/or an associated remedial algorithm and performs at least one automated remedial action in response thereto.

Example implementations of biomedical acoustics classifiers will now be described in more detail with reference to FIGS. 2 through 17.

Figure 2:
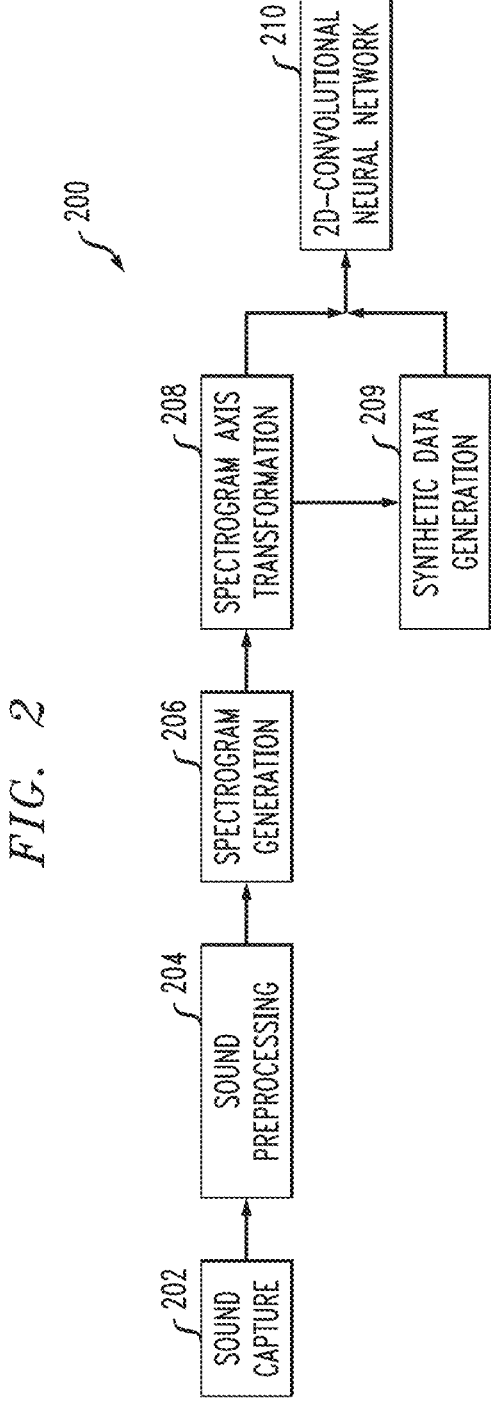
FIG. 2 is a block diagram of an example biomedical acoustics classifier in an illustrative embodiment.

FIG. 2 shows one example of a biomedical acoustics classifier 200 in an illustrative embodiment.

In this embodiment, the biomedical acoustics classifier 200 illustratively comprises a sound capture component 202, a sound preprocessing component 204, a spectrogram generation component 206, a spectrogram axis transformation component 208, a synthetic data generation component 209 and a two-dimensional (2D) convolutional neural network (CNN) 210, also referred to as a 2D-CNN, arranged as shown in the figure. The 2D-CNN 210 is used as an example, and other types of neural networks, as well as associated classifier components, can be used in other embodiments.

In the sound capture component 202, sound produced from the body is captured, for example, by a transducer or other type of sensor, such as a sensor associated with an intelligent stethoscope or other patient monitoring device. The transducer converts pressure waves into electrical signals. The electrical signal is digitized by an analog-to-digital converter, to provide a digitized audio signal. Such an audio signal or other type of sound signal is an example of what is more generally referred to herein as an "acoustic signal." It is to be appreciated that a wide variety of other types of acoustic signals can be used in other embodiments. The sound capture component may be viewed as an example of one of the acoustic signal sources 105 of FIG. 1, although other acoustic signal sources can be used. In some embodiments, the sound capture component 202 is considered part of the biomedical acoustics classifier 200, while in other embodiments it is implemented as a separate component that is not part of the biomedical acoustics classifier 200.

The sound preprocessing component 204 performs one or more preprocessing operations to clean up the sounds signal for better classification performance. For example, the amplitude of the sound signal is illustratively normalized to unity to compensate for possible amplitude variations. Additionally or alternatively, a bandpass filter is illustratively used to selectively isolate the sounds in their biological frequency range, filtering out unwanted higher and lower frequency sounds.

In the spectrogram generation component 206, the sound signal is segmented into overlapping windows, and then a Fast Fourier Transform (FFT) is applied on each window to generate a spectrogram. In some embodiments, windowing is accomplished using a Hann window of size 512 and hop length of 256, although other techniques can be used. A 512-point FFT is illustratively applied to each window to generate a spectrogram, which depicts frequency over time, with the amplitude of a particular frequency at a particular time represented by the intensity of color of the corresponding point in the spectrogram. Such a spectrogram has three dimensions, time, frequency and amplitude, each corresponding to a different axis of the spectrogram, although other spectrogram formats can be used. The term "spectrogram" as used herein is therefore intended to be broadly construed.

A spectrogram is an example of what is more generally referred to herein as an "image representation" of a sound signal or other acoustic signal. Other types of image representations can be used in other embodiments, such as recurrence plots.

In the spectrogram axis transformation component 208, the generated spectrograms are transformed from linear scale to logarithmic scale. More particularly, a logarithmic transform is applied to both the frequency axis and the amplitude axis of the spectrogram. The motivation behind the logarithmic scaling is that humans tend to perceive sounds logarithmically, with more discriminative ability at lower frequencies and intensities and less discriminative ability at higher frequencies and intensities. For example, humans are better able to hear the difference between 200 Hz and 300 Hz compared to the difference between 2000 Hz and 2100 Hz, despite the fact that the difference in frequency is 100 Hz in both cases. Furthermore, sounds produced by the body are more concentrated in the lower frequency ranges.

The logarithmic transformation illustratively ensures a more perceptually accurate, human-centric representation of sound. This is important for two reasons. First, it improves model performance since biomedical sounds are typically found within the lower frequency ranges. A logarithmic transformation provides more resolution at the lower frequency ranges which contain the more useful information, and less resolution at higher frequency ranges which contain less useful information. Second, in illustrative embodiments, the 2D-CNN 210 is trained to discern sounds as a human would, since the established clinical protocol of what to do depending on the sound heard is formulated around the sounds that doctors or other medical professionals can perceive.

In some embodiments, the logarithmic transformation for the frequency axis is a transformation based on the Mel scale, which is characterized by the following equation:

$$Mel = 2595 * \log\left(1 + \frac{f}{500}\right)$$

where f is frequency in Hz. Other logarithmic transformations that can be used for the frequency axis include, for example, the Bark scale. In some embodiments, the logarithmic transformation for the amplitude axis is based on the decibel (dB) scale. Again, this is only an example, and other types of logarithmic transformations can be used.

In some embodiments, different transformations are applied to each of the axes of the spectrogram. For example, respective first, second and third distinct transformations can be applied to respective first, second and third axes of the spectrogram. Alternatively, the same or similar transformations may be applied to two or more of the axes of the spectrogram. Numerous alternative transformations can be used, as described elsewhere herein.

Figure 3B:
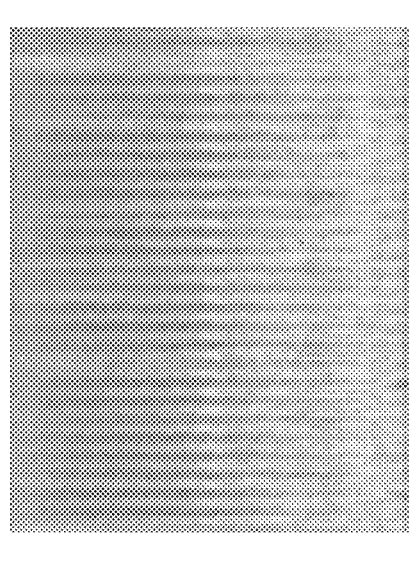
FIGS. 3A, 3B and 3C illustrate example spectrograms utilized in illustrative embodiments. These figures are collectively referred to herein as FIG. 3.
Figure 3A:
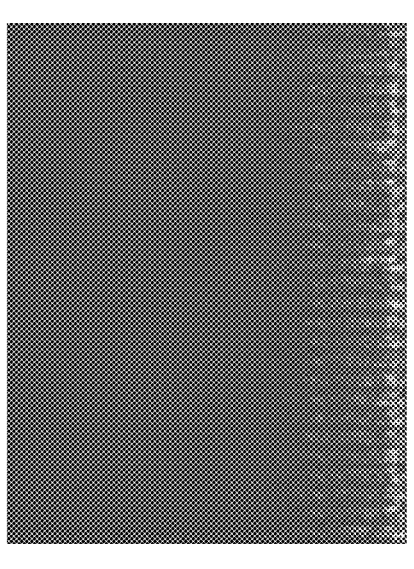

FIGS. 3A and 3B illustrate the difference between a spectrogram on a linear scale, shown in FIG. 3A, and a Mel-scaled, dB-scaled spectrogram shown in FIG. 3B, for the same heart sound signal. For the linear scale spectrogram, no transformations are applied, while for the other spectrogram, logarithmic transformations are applied on the frequency and amplitude axes, using respective Mel scale and dB scale transformations. A given such Mel-scaled, dB-scaled spectrogram may be viewed as an example of what is more generally referred to herein as a "Mel-spectrogram."

Figure 3C:
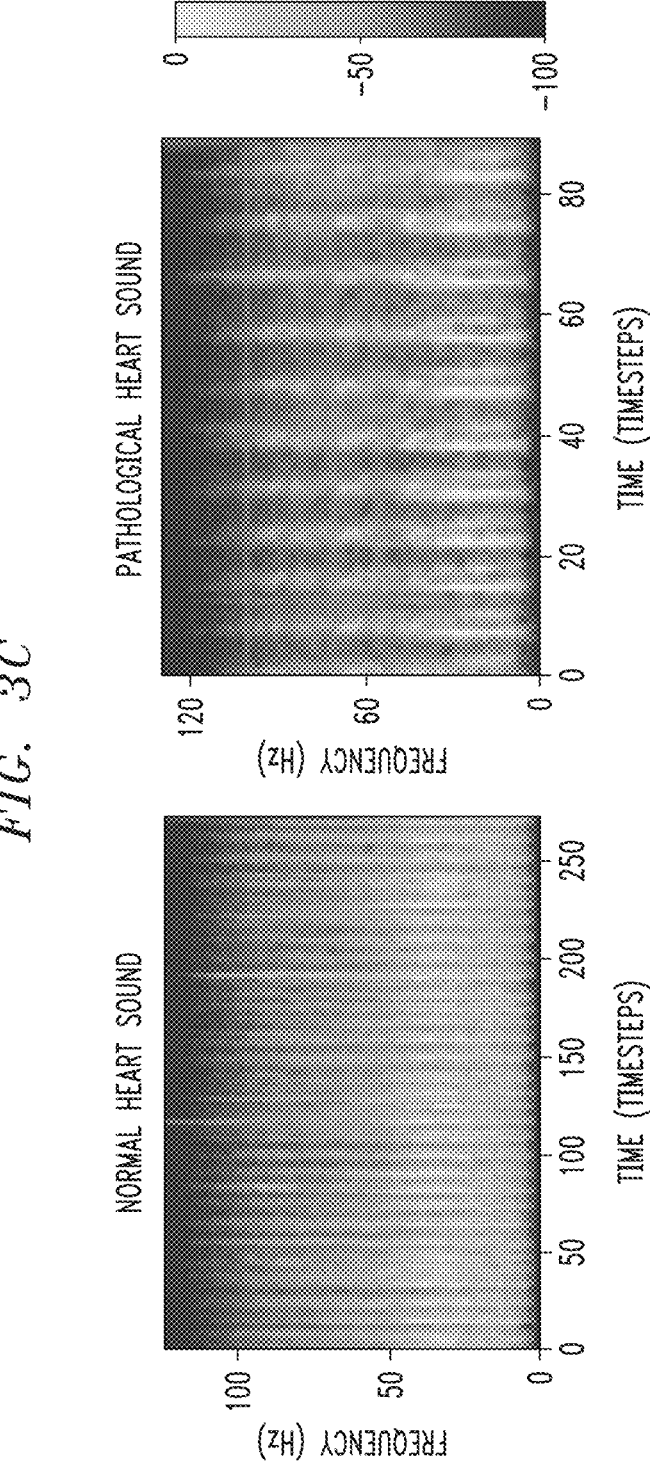

As illustrated in FIG. 3C, spectrograms of the type shown in FIG. 3B can be used to distinguish normal heart sounds from pathological heart sounds using the techniques disclosed herein. The left side of FIG. 3C shows a spectrogram for a normal heart sound, and the right side of FIG. 3C shows a spectrogram for a pathological heart sound.

Referring again to FIG. 2, in the synthetic data generation component 209, synthetic data is generated from real data by applying masks in the time and frequency domain onto the spectrograms generated in the previous step.

In some embodiments, three masks are randomly applied in the time domain, and three masks are randomly applied in the frequency domain. In frequency masking, the frequency channels $[f_0, f_0+f)$ are masked, where f is randomly chosen from the uniform distribution [0, 20], and where $f_0$ is randomly chosen from $(0, v-f)$, where v is the total number of frequency channels. In time masking, the time steps $[t_0, t_0+t)$ are masked, where t is a randomly chosen from the uniform distribution [0, 20], and where $t_0$ is randomly chosen from $(0, \tau-t)$, where $\tau$ is the total number of time steps.

Figure 4:
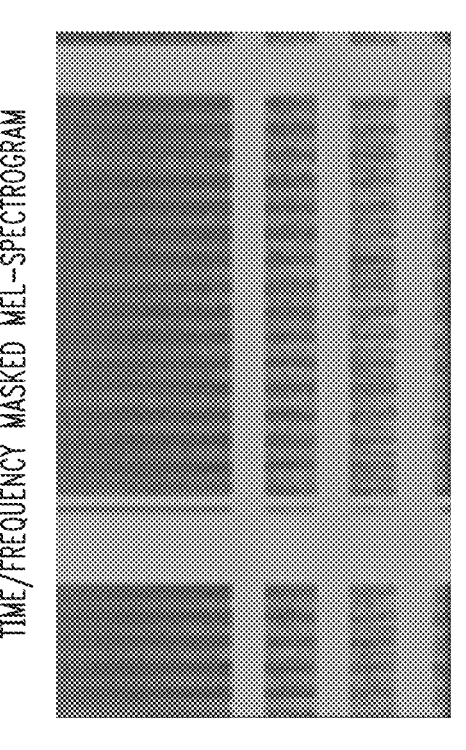
FIGS. 4 and 5 show examples of synthetic spectrograms generated using various data augmentation techniques as disclosed herein.

FIG. 4 shows an example of a synthetically-generated spectrogram, obtained using masks of the type described above. It is to be appreciated that other types of masks can be used in other embodiments. Also, other types of data augmentation techniques can be used, in addition to or in place of masking-based data augmentation techniques.

In some embodiments, data augmentation using the synthetic data generation component 209 is carried out in a one-to-one correspondence with real audio signals, meaning that for each real audio signal, a corresponding synthetic audio signal is generated from it. This doubles the size of the acoustics dataset available for training. In this context, a real audio signal refers to a sound signal collected directly from a patient, and a synthetic audio signal refers to an audio signal that is created from a corresponding real audio signal using the synthetic data generation component 209 of the biomedical acoustics classifier 200.

Masking induces information loss at various points in the time and frequency domains. The 2D-CNN 210 is forced to learn multiple independent representations of the same data, which combats overfitting. Disease-appropriate forms of data augmentation are integral to improvements in model performance in the medical domain, and synthetic data is most meaningful when it lies within the scope of human physiology and can accurately mimic clinical findings. Masking is a powerful data augmentation technique for clinical data since it will never suffer from the possibility of pushing data outside the scope of normal physiological or even pathophysiological limits, since it is not modifying the underlying data and only inducing partial information loss to the data prior input into the 2D-CNN 210.

Illustrative embodiments herein utilize masking as a data augmentation technique in order to facilitate classification of audio signals based on their respective image representations. Generating synthetic data as disclosed herein addresses one of the major issues in machine learning in the medical domain: creating and validating a large enough database to train a machine learning model suitable for real-world clinical applications is limited by the scarcity of labeled clinical data. This scarcity issue can be attributed to several challenges unique to the medical domain, including: the relative paucity of available clinical databases structured for machine learning research, the administrative and logistical hurdles associated with collecting and working with patient data and protected health information due to Health Insurance Portability and Accountability Act (HIPAA) laws and Institutional Review Board (IRB) regulations, and finally the time-consuming and expensive nature of properly annotating health data. For example, the gold standard for validating heart sounds is echocardiogram imaging plus the diagnosis from a cardiologist, both of which are costly to obtain. An additional challenge in creating a machine learning model to classify biomedical sounds is that sounds are not actually recorded and stored anywhere in electronic health records (EHR). Mining EHR databases is not an option, meaning sounds must be collected and labeled from scratch, one-by-one. This is an expensive, labor-intensive, and time-consuming process.

Thus, an important advantage of generating synthetic data in the manner disclosed herein resides in its ability to significantly expand the size of available training data without the onerous task of having to actually obtain and label a large enough volume of data. An expanded dataset can improve model performance because the new data created from class-preserving transformations can help the model better learn the unique features that constitute the essence of a class, instead of the random variance that is present within each class. Data augmentation combats overfitting and can help the model make better predictions on unseen data.

As noted above, other types of additional or alternative data augmentation techniques can be used in other embodiments.

For example, another synthetic data generation method that can be applied in illustrative embodiments disclosed herein involves using the spectrogram images to train a Generative Adversarial Network (GAN), and then using the trained GAN to generate new, synthetic spectrograms to train the CNN.

Figure 5:
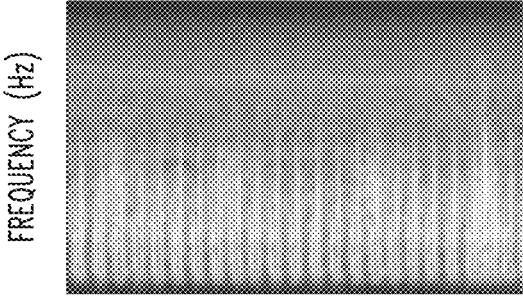

FIG. 5 illustrates another example data augmentation technique, involving horizontal or vertical flipping of a spectrogram. The upper portion of the figure shows an unaltered spectrogram, and the lower portion of the figure shows on the left the result of horizontally flipping the spectrogram and on the right the result of vertically flipping the spectrogram. In the context of heart sound classification, experiments conducted on illustrative embodiments disclosed herein indicate that horizontal flipping of a spectrogram about the central vertical axis generally provides better performance than a similar vertical flipping arrangement.

Other synthetic data generation methods are described elsewhere herein. Accordingly, it is to be appreciated that illustrative embodiments are not limited to use with masking-based data augmentation techniques, GAN-based data augmentation techniques, and/or flipping-based data augmentation techniques.

The operation of the 2D-CNN 210 of the biomedical acoustics classifier 200 will now be described in further detail with reference to FIGS. 6 and 7.

The spectrograms generated in the manner described above are treated as images and standardized in size using bicubic interpolation. Both the real and artificially created spectrograms are used to train the 2D-CNN 210 for classification.

Figure 6:
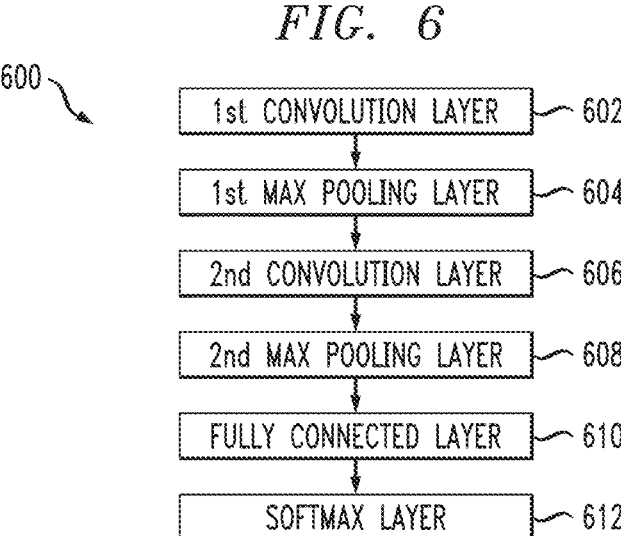
FIG. 6 shows an example convolutional neural network utilized in a biomedical acoustics classifier in an illustrative embodiment.

In some embodiments, the 2D-CNN 210 comprises a layered architecture 600 as shown in FIG. 6, including a first convolutional layer 602, a first max pooling layer 604, a second convolutional layer 606, a second max pooling layer 608, a fully connected layer 610, and a softmax layer 612. Other types and arrangements of dimensions and layers can be used in other embodiments. For example, the softmax layer in some embodiments can be replaced with at least one of a built-in activation function and an activation layer.

Additionally or alternatively, other embodiments can include more or fewer convolutional layers and max pooling layers. For example, other embodiments can utilize three convolutional layers and three max pooling layers, instead of two convolutional layers and two max pooling layers as in the example of FIG. 6. Numerous other variations can be made in the numbers and types of layers and their specific configuration in other embodiments, as will be appreciated by those skilled in the art.

Figure 7:
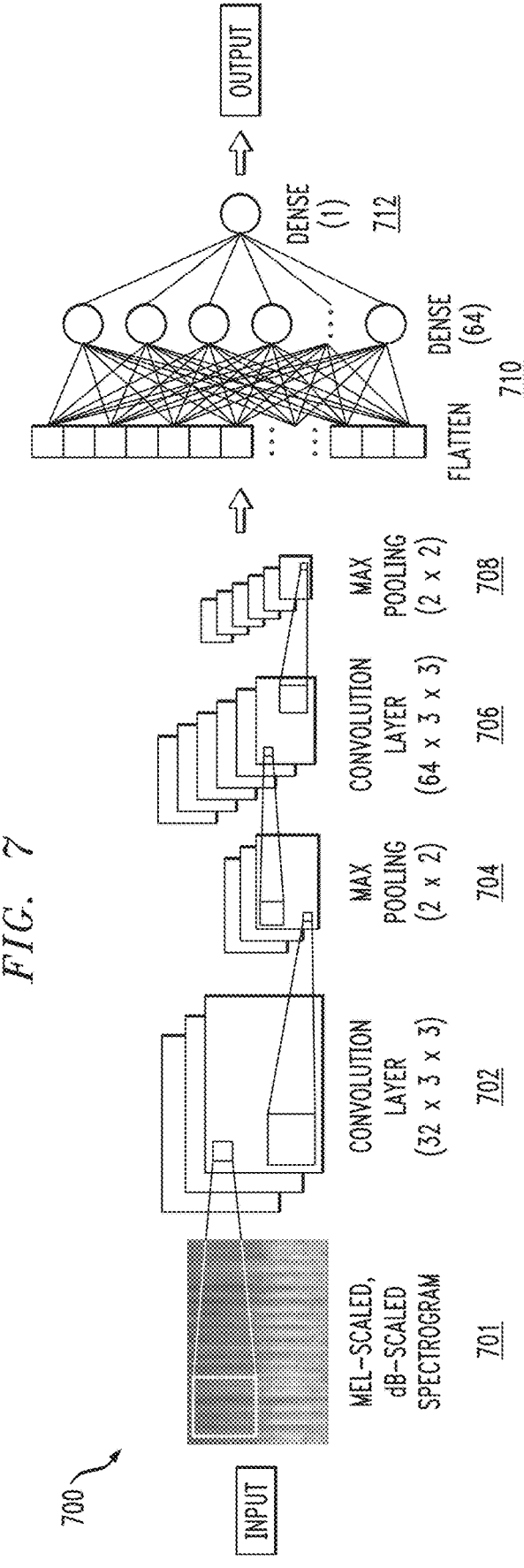
FIG. 7 shows a more detailed view of one possible implementation of the convolutional neural network of FIG. 6.

FIG. 7 shows a more detailed view of one possible implementation of a layered architecture 700 of the 2D-CNN 210. The layered architecture 700 receives as an input a Mel-scaled, dB-scaled spectrogram 701. In some embodiments, the spectrogram 701 illustratively comprises red, green and blue (RGB) decomposition matrices, although numerous other spectrogram formats may be used. A first convolutional layer 702 comprises 32 3×3 kernels, each with a stride length of one; the activation function used is a rectified linear unit (ReLU) activation function. This is followed by a max pooling layer 704 with a filter of size 2×2 and stride length of two. The next layer is a second convolutional layer 706 with 64 3×3 kernels, each with a stride length of one; the activation function used is a ReLU activation function. Similarly, it is followed by a max pooling layer 708 with a filter of size 2×2 and a stride length of two. Padding is not used in any layer in the present embodiment. The output from the previous operation is flattened into a one-dimensional feature vector, and then passed to the next layer, which is a fully-connected layer 710 with 64 hidden units. A final layer 712 comprises a single neuron with a softmax activation function to make the final classification.

Again, these particular layers and their respective configurations are presented by way of illustrative example only, and can be varied in other embodiments, as will be readily apparent to those skilled in the art. For example, illustrative embodiments are not limited to use with softmax activation functions.

Additional illustrative embodiments of biomedical acoustics classifiers will now be described with reference to FIGS. 8A and 8B.

Figure 8A:
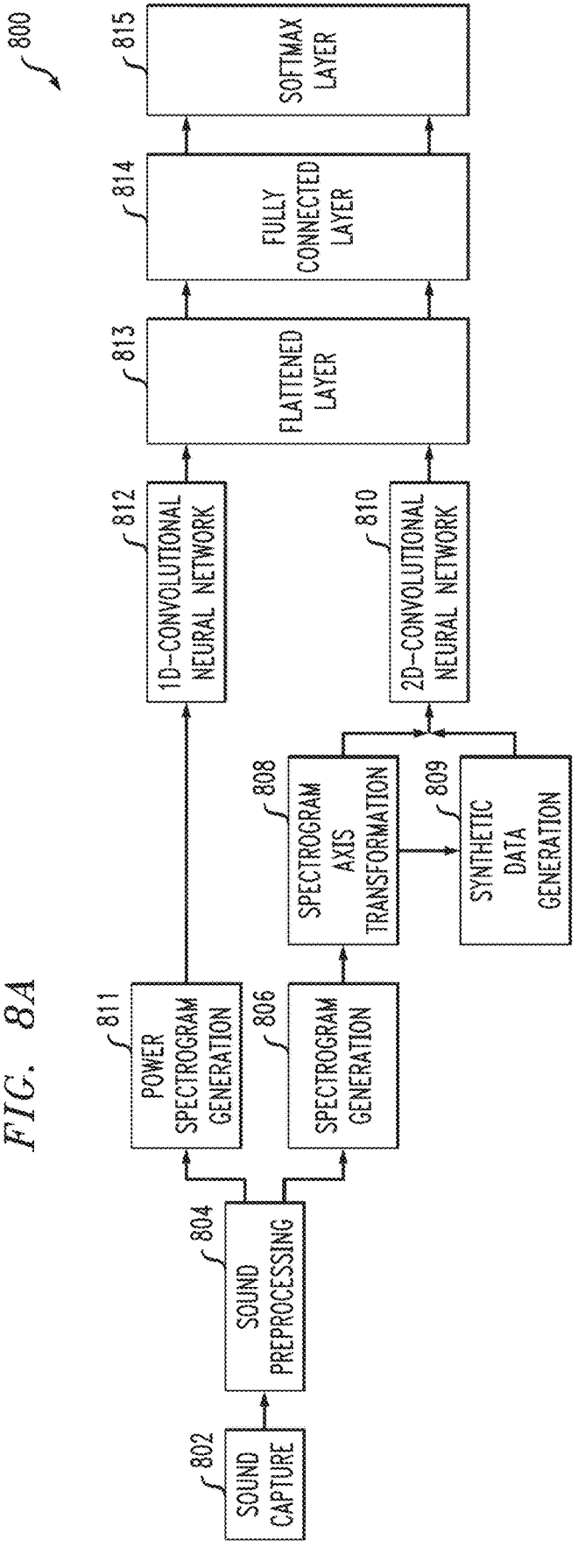
FIGS. 8A and 8B are block diagrams of other example biomedical acoustics classifiers in illustrative embodiments. These figures are collectively referred to herein as FIG. 8.

Referring initially to FIG. 8A, a biomedical acoustics classifier 800 utilizing a spectrogram and a power spectrum is shown. The biomedical acoustics classifier 800 includes a number of components similar to those of the FIG. 2 embodiment as described above, including a sound capture component 802, a sound preprocessing component 804, a spectrogram generation component 806, a spectrogram axis transformation component 808, a synthetic data generation component 809, and a 2D-CNN 810, each generally configured in a manner similar to that of the corresponding component of the FIG. 2 embodiment.

The biomedical acoustics classifier 800 further includes a power spectrum generation component 811, a one-dimensional (ID) CNN 812, also referred to as a 1D-CNN, and a plurality of additional layers, including a flattened layer 813, a fully connected layer 814 and a softmax layer 815, arranged as shown in the figure. The 1D-CNN 812 in this embodiment operates on the power spectrum of the sound signal, as will be described in more detail below, in parallel with the 2D-CNN 810 which operates on the image representations in a manner similar to that previously described. Again, the softmax layer 815 in some embodiments can be replaced with at least one of a built-in activation function and an activation layer. Other types and arrangements of layers can also be used.

In the power spectrum generation component 811, a Discrete Fourier Transform (DFT) is applied to the sound signal (amplitude vs. time) to generate a power spectrum (power vs. frequency). The resulting power spectrum is treated as time series data and used to train the 1D-CNN 812.

In the flattened layer 813, output from the 1D-CNN 812 and 2D-CNN 810 are flattened and concatenated together into one feature vector. This feature vector is passed into the fully connected layer 814, with the result being applied to the softmax layer 815 for classification.

The example parallel neural network structure of the FIG. 8A embodiment allows acoustic signal information encoded in the time domain and frequency domain to be analyzed simultaneously and the learned features to be merged together in determining the final classification.

Figure 8B:
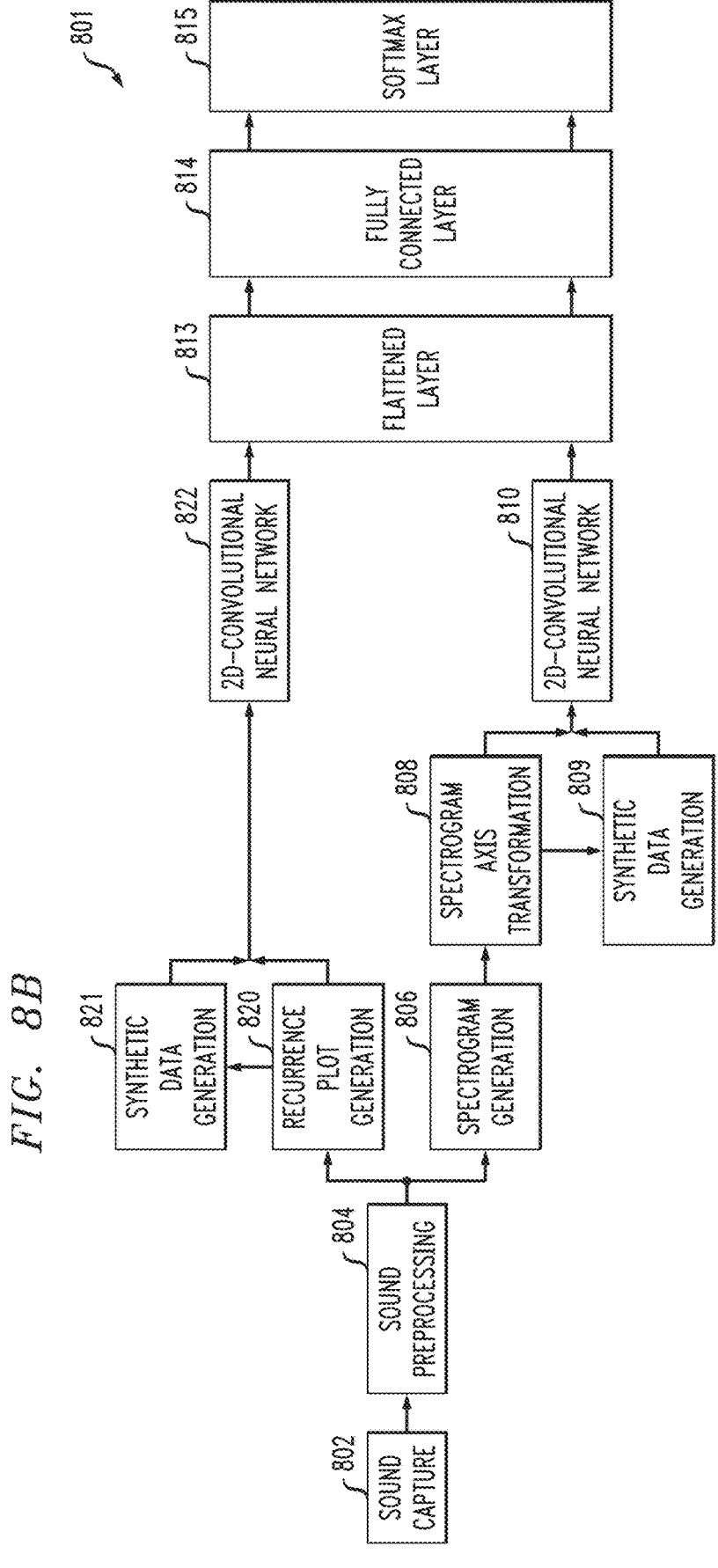

Referring now to FIG. 8B, a biomedical acoustics classifier 801 utilizing both a spectrogram and a recurrence plot is shown. Like the biomedical acoustics classifier 800 of FIG. 8A, the biomedical acoustics classifier 801 includes sound capture component 802, sound preprocessing component 804, spectrogram generation component 806, spectrogram axis transformation component 808, synthetic data generation component 809, 2D-CNN 810, flattened layer 813, fully connected layer 814 and softmax layer 815, each generally configured in a manner similar to that of the corresponding component of the FIG. 8A embodiment.

The biomedical acoustics classifier 801 further includes a recurrence plot generation component 820, a synthetic data generation component 821, and a 2D-CNN 822. The recurrence plot generation component 820 generates a recurrence plot of the sound signal in the manner described elsewhere herein. The 2D-CNN 822 in this embodiment operates on the recurrence plot of the sound signal, in parallel with the 2D-CNN 810 which operates on the spectrogram in a manner similar to that previously described. Other types and arrangements of layers can also be used in other embodiments.

The example parallel neural network structure of the FIG. 8B embodiment allows acoustic signal information encoded in the spectrogram and the recurrence plot to be analyzed simultaneously and the learned features to be merged together in determining the final classification.

Figure 9:
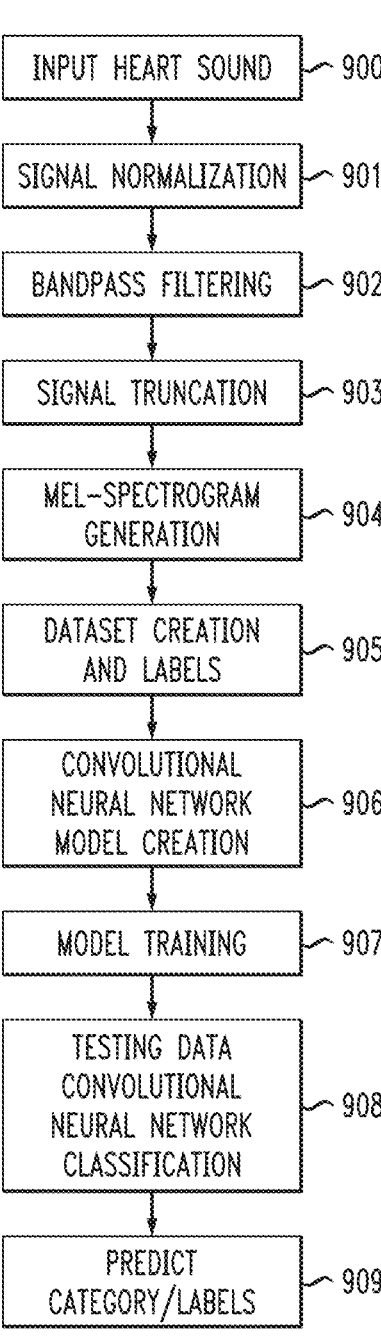
FIG. 9 is a flow diagram of an example process for classifying a heart sound in an illustrative embodiment.

FIG. 9 shows a flow diagram of an example process for use in conjunction with classifying a heart sound in an illustrative embodiment, using a biomedical acoustics classifier of the type illustrated in FIG. 2 or FIG. 8A. The process illustratively comprises steps 900 through 909 as shown. In this embodiment, the acoustic signal to be classified is a heart sound, but the various steps shown in the figure can be similarly implemented for classification of other types of acoustic signals.

The process in this embodiment includes obtaining an input heart sound in step 900, performing signal normalization, bandpass filtering and signal truncation in respective steps 901, 902 and 903, generating a Mel-spectrogram in step 904, dataset creation and labeling in step 905, CNN model creation in step 906, model training in step 907, testing data CNN classification in step 908, and prediction of category/labels in step 909. Different instances of the process are illustratively performed using different input heart signals, possibly using only subsets of the process operations. For example, once the CNN is adequately trained and tested, one or more associated process steps can be omitted in subsequent instances of the process.

The particular process operations shown in FIG. 9, although illustrated as being performed sequentially, can in other embodiments be performed at least in part in parallel with one another, or in different orders. Also, additional or alternative processing operations can be used in other embodiments.

Again, the particular classifiers and their components as shown in FIGS. 2, 6, 7 and 8 are considered illustrative examples only.

Additional examples of biomedical acoustics classifiers comprising different arrangements of multiple parallel CNNs will be described below in conjunction with the illustrative embodiments of FIGS. 11 and 12.

In other embodiments, different types of neural networks can be used. For example, some embodiments can be implemented using recurrent neural networks (RNNs). Acoustic signal data can be acquired and transformed into an image representation in a manner similar to that described previously. The output from this step can be passed through a memory segment known as a Long Short-Term-Memory (LSTM) block that contains three gates, with input, output and forget functions of experimentally determined weights. The output is then passed through a dropout layer to reduce overfitting and optimize model generalizability. The resulting vectors then go through a dense layer and activation function for classification. The RNN's capacity to handle time series information provides robust analysis and detection against noisy and shortened samples, which are frequent in clinical settings.

As another example of an alternative neural network arrangement, some embodiments are configured to utilize a merged CNN and RNN architecture. Such an embodiment leverages the long-term dependencies that are present in some types of acoustic signals, such as heart sound signals. In a first step, a CNN architecture with convolution and max pooling layers is used to generate feature vectors. This allows for the organic discovery of attributes that are most relevant to the analysis. The output then gets passed through an LSTM block with input, output and forget gates, adaptive multiplicative gates and peephole connections, and subsequent dense layers for classification. This hybrid CNN and RNN/LSTM structure expands the analytical range of the model, and allows training data to include image, plot or graphic representation of the original acoustic signal.

Other embodiments can use alternative techniques for generating additional, synthetic acoustic data from real audio signals while preserving the class label. Generating synthetic acoustic data with a preserved class label greatly expands the training data available for acoustic classification models to learn from. Such embodiments overcome the scarcity issue in creating a large enough database for training acoustic classification models suitable for real-world, clinical use. The inclusion of synthetic acoustic data will force the model to learn the relevant features that characterize each sound. This will combat overfitting, and lead to a model that has greater generalizability.

More detailed examples of techniques for generating additional, synthetic acoustic data from real audio signals will now be described, in the context of heart sounds although the disclosed techniques are broadly applicable to other types of acoustic signals.

It is assumed for these examples that heart sounds are recorded from patients using a transducer that converts pressure waves into electrical signals. The electrical signal is digitized by an analog-to-digital converter. The digitized heart signal is processed to generate the additional, synthetic acoustic data, using one or more of the following independent operations: noise injection, time shifting, pitch shifting, speed shifting, random silencing, and signal inversion. Each such operation is a transformation that takes a digitized heart sound as its input and produces a new, never-been-heard before digitized heart sound as the output.

Each operation has its own set of parameters. The value of the parameters modulates the degree of the transformation each operation applies to an input signal in generating the output signal. For example, the parameter for the time shifting operation is the number of seconds to shift the signal forward or backwards. Thus, many synthetic heart sounds can be generated from a single operation by varying its parameter(s).

Each operation simulates a potential situation that can arise at bedside not captured in the original audio recording (e.g., down shifting the pitch of a heart sound reflects hearing the same heart hemodynamics but in a patient with a thicker chest wall).

Each operation preserves the essential temporal and spectral features that characterized the input signal, meaning the label assigned to the input signal is preserved and can be assigned to the output signal.

Each operation can also be used in combination with any number of the other operations (e.g., the output of pitch shifting operation can be the input to the random silencing operation to generate yet another never-been-heard before audio signal). Thus, a vast variety of new synthetic heart sounds can be generated from a single, real heart sound recording.

The example independent operations are each described in turn below. Other similar operations, or combinations of these or other operations, can also be used.

The noise injection operation generates a new audio signal by introducing noise into the input signal. The noise can be either white noise; common hospital ambient noises such footsteps, alarms, beeping of machines, coughing, talking, ringing phones, tray tables being pushed, ambulance sirens; or internal bodily noises such as lung and bowel sounds. The two parameters associated with the noise injection operation are the type of ambient noise, and the time at which the ambient noise is added. This operation aims to create data that captures the large gamut of potential environmental noises encountered in patient rooms, differing conditions during physical exams, and the variable nature of recording artifacts. Noise injection teaches the algorithm to selectively identify and correctly weigh relevant features, since noise will vary from sample to sample but the label will remain constant.

The shifting time operation generates a new audio signal that is a time shift of the input signal. The output signal is generated by extracting out a defined window of the input signal. The parameters associated with the shifting time operation include t, the time at which to start the window (measured from time zero in the input signal), and l, the length of the window. The output signal at time 0 corresponds with the input signal at time x, and the output signal at time l corresponds with the input signal at time x+l. In clinical settings, doctors may begin acquisition at any point amid the heart cycle, so it is important that a model recognizes different time shifts of the same signal.

The changing pitch operation generates a new audio signal by altering the pitch of the input signal. The output signal is created in three steps. First, the instantaneous frequency-amplitude relationship of the input signal is calculated using the short-time Fourier transform (STFT). The amplitudes at each frequency bin are collectively shifted up (increasing pitch) or down (decreasing pitch) the frequency axis by the same factor. The frequencies of the signal components retain their harmonic relationships, but the perceived pitch will now be different. Finally, the inverse STFT is performed on each frequency bin and the resulting waveforms are combined to produce the output signal. The parameter associated with the changing pitch operation is the factor by how much to shift the amplitudes up or down in the frequency domain, which in turn controls the perceived pitch. Changing pitch reflects different anatomical variations physicians may encounter in auscultating the heart including differing myocardium wall thickness, body fat/water composition, patient bone/rib structure, and the actual heart size, all of which may lead to variabilities in heart sound attenuation. Creating a model that recognizes the temporal features and other distinctive characteristics of the signal irrespective of pitch will improve its performance.

The changing speed operation generates a new audio signal that is a sped up or slowed down version of the input signal. The output signal is created by increasing (speeding up) or decreasing (slowing down) the sampling rate of the input signal. The parameter associated with the changing speed operation is the factor by how much to increase or decrease the sampling rate. This operation is analogous to changing the heart rate of a patient. It may introduce pitch shifts to the audio signal (in a sense, similar to above), and addresses the issue of the natural variability in patient heart rates. An important application is in classification of pediatric heart sounds as a child's normal heart rate drops as they grow, so simulating a spectrum of heart rates in the original training set will make the model more robust for a wider age range.

The random silences operation generates a new audio signal by overriding portions of the input signal with null values (silence). The two parameters associated with this operation are t, the time in the input signal to introduce the silence, and l, the length of the silence. This will train the model to interpolate missing data given time series information, and overcome the difficulties that gaps and null values impose on feature extraction. This will mimic unsteady connections or scenarios where the signal acquisition process is interrupted, and will enable the model to become relevant in a wider range of settings (e.g., rural/global health clinics).

The signal inversion/reversal operation generates a new audio signal that is a mirror of the original signal. Some embodiments utilize both time inversion and amplitude inversion, or other arrangements of additional or alternative augmentation operations. There are no associated parameters with this operation. While not directly correlated to a bedside scenario, it may help improve the sensitivity and specificity of the machine learning model during the training process because the model will have more labeled training data from which to learn the relevant features.

Additional examples of data augmentation techniques suitable for use in illustrative embodiments herein will now be described.

Some data augmentation techniques disclosed herein provide a solution to the legal limitations and constraints around clinical data. Data augmentation in some embodiments comprises a process of generating synthetic data from real data, while preserving the class label. In the context of developing machine learning models for heart sound classification, real data illustratively comprises heart sounds collected directly from a patient, whereas synthetic data illustratively comprises artificial heart sounds generated from real heart sounds via various computer-implemented methods, although the terms "real" and "synthetic" as used herein are intended to be more broadly construed.

A major value add of data augmentation for heart sound classification resides in its ability to significantly expand the size of available training data without the onerous task of having to actually obtain and label a large enough volume of heart sounds. An expanded dataset can improve model performance because the new data created from class-preserving transformations can help the model better learn the unique features that constitute the essence of a class, instead of the random variance that is present within each class. Data augmentation combats overfitting and can help the disclosed models make better predictions on unseen data.

Data augmentation is necessarily domain specific, as the applied transformations should reflect realistic variations and preserve the underlying features that distinguish different classes from each other. In other words, the data augmentation should "make sense" for the task at hand. Two important constraints unique to heart sound spectrograms are considered in designing effective data augmentation strategies as disclosed herein.

The first constraint, referred to herein as the "physiological constraint," is related directly to the phenomenon under study, the heart sound itself. Heart sounds naturally fall within a narrow physiological scope: heart rates are typically 60-100 beats per minute and the principal frequencies of heart sounds are 20 to 500 Hz. A healthy heart sound can be deconstructed into four main frequency components: S1 (mitral and tricuspid valve closing), systole (ventricles contracting), S2 (aortic and pulmonic valve closing), and diastole (ventricles relaxing). A pathological heart sound has all the same frequency components. The difference between a healthy heart sound and pathological heart sound is that a pathological heart sound will have additional frequency components such as murmurs from valve stenosis or regurgitation, rubs from pericarditis, S3 gallops (e.g., from increased atrial pressure, as seen in congestive heart failure or dilated cardiomyopathy), or S4 gallops (e.g., atrium contracting against stiff ventricle caused by hypertension, pulmonary hypertension, ventricular outflow obstruction, or ischemic heart disease). Of note, an additional sound that can be produced by a healthy heart is the physiological splitting of S2 due to delayed pulmonic valve closing. Thus, the physiological constraint in illustrative embodiments specifies that the data augmentation method reflects realistic variations of possible heart sounds and also ensures that the presence or absence of additional frequency components is preserved for each individual heart sound or else the distinguishing factor between a normal and abnormal heart sound is lost and the class labels lose their meaning.

The second constraint, which is referred to herein as the "spectrogram constraint," is related to the spectrogram image and what it represents. One advantage for using example CNNs as disclosed herein to classify heart sounds is that this converts an audio classification problem into a computer vision problem, which opens the door to the extensive library of data augmentation techniques developed for images. Examples of image data augmentation techniques include flipping, cropping, rotation, translations, color space transformations, kernel filters to sharpen or blur images, mixing images, and random erasing. However, not all image data augmentation techniques will translate appropriately to particular biomedical acoustics contexts. Although spectrograms are images from a data structure point of view, spectrograms and traditional images have a fundamental difference in terms of what information is conveyed along the x-axis and y-axis. For a traditional image, these axes represent physical distances, while for spectrograms the x-axis represents time and the y-axis represents frequency. Moreover, color also carries a different meaning for traditional images versus spectrogram images. The meaning of color is self-evident for traditional images. For spectrograms, color is an additional dimension that represents decibels, or the loudness and intensity of the heart sound. Thus, the spectrogram constraint specifies that any data augmentation method that operates on the spectrogram as a simple image should correlate with a real-world, physical transformation of the sound.

With these constraints in mind, experiments were performed on illustrative embodiments to evaluate example data augmentation techniques at the audio level, including pitch shifting and time stretching/compressing and noise injection, and at the image level, including horizontal flips, vertical flips, hue/brightness transformations, principal component analysis (PCA) color augmentation, random color filters, and time/frequency masking, for classification of heart sounds based on their spectral image. These examples include data augmentation methods that are consistent with, and others that contradict, what would be an effective data augmentation method as predicted by the theoretical considerations described above. Additional description below will 1) examine the individual effectiveness of each augmentation technique on heart sound classification and 2) assess the validity of the associated theoretical framework.

To study the effects of these example data augmentation methods on heart sound classification, the experiments performed on illustrative embodiments were separated into two phases. The first phase established the baseline performance of an example CNN on spectral images of heart sounds. In the second phase, the same CNN is trained on both real and synthetically generated heart sounds. Model performance with and without data augmentation on the same binary classification task is compared. Each individual data augmentation method is carried out in accordance with a one-to-one correspondence, meaning for every real heart sound, one synthetic heart sound is generated from it. This doubles the size of the dataset available for training, from N to 2N.

The data in this study was sourced from a publicly available database assembled from the PhysioNet/Computing in Cardiology (CinC) Challenge in 2016. The directory contains 3,239 recorded heart sounds that range between 5-120 seconds. The sounds were compiled by physicians and research teams across seven countries over the course of a decade. Experts in cardiology labelled the heart sounds as either normal or abnormal. Normal sounds are sounds collected from patients with no underlying cardiometabolic conditions. Abnormal sounds are sounds collected from patients with an underlying cardiac pathology, including valvular defects (e.g., mitral prolapse, mitral regurgitation, aortic regurgitation, aortic stenosis and valvular surgery), as well as coronary artery disease. Of the recorded heart sounds, 2575 were labeled as normal and the remaining 664 sounds were labeled as abnormal.

With regard to preprocessing, the raw heart sounds were first processed by a third-order Butterworth filter with a passband of 20-500 Hz, which encapsulates the range of normal heart sound and murmur frequencies. All sounds under 8 seconds were discarded. Then, the samples were either truncated to 30 seconds if their length exceeded that limit, or preserved in their entirety if the length was less than 30 seconds. Subsequently, the amplitudes of the signals were normalized in accordance with the following equation:

$$X_{norm} = \frac{X}{\max(|X|)}$$

where X refers to the amplitude of the signal, to ensure that signal amplitude is standardized across all recordings.

Mel-spectrogram images were generated from the preprocessed heart sounds in the manner described elsewhere herein. The resulting Mel-spectrogram images were standardized by rescaling each image to be of size 100×180 using bicubic interpolation.

Example data augmentation techniques are applied in the manner described below.

Pitch Shifting and Time Stretching/Compression—Method 1

To create a synthetic heart sound using pitch shifting and time stretching/compression, each real heart sound is first randomly pitch shifted up or down by p semitones, where p is a randomly chosen integer between 1 and 10. A semitone is defined as the interval between two adjacent notes in a 12-tone scale. For example, on a musical scale, the interval between C and C# is one semitone. Then the pitch shifted sound is randomly time stretched/compressed by a factor of t, where t is randomly chosen from the uniform distribution [0.5, 2.0]. For example, if t=2.0, then a 30 second audio file is stretched to 60 seconds, or if t=0.5, then a 30 second audio file is compressed to 15 seconds. The pitched shifted and time stretched/compressed sounds are then converted to Mel-spectrogram images, which are used to supplement the Mel-spectrogram images derived from real heart sounds to train the example CNN.

Noise Injection—Method 2

To create a synthetic heart sound using noise injection, additive white Gaussian noise (AWGN) is injected element-wise into the original signal. The amplitude of AWGN is modeled as a Gaussian distribution, with μ=0. The standard deviation of the noise signal is described with the following formula:

$$RMS = \sqrt{\frac{\sum_i x_i^2}{n}}$$

Assuming a signal-to-noise ratio (SNR) of 0, the required $RMS_{noise}$ can be approximated by $RMS_{signal}$. Each element of the noise signal is independently sampled from the distribution X~N(μ, σ²) where μ=0, σ=$RMS_{signal}$. The resulting noise signal is summed with the original sample. The synthetic samples are converted to Mel-spectrogram images and combined with the real heart sound Mel-spectrogram database to train the CNN model.

Image Flipping—Methods 3.1 and 3.2

To create synthetic data using image flipping, each real heart sound is first converted to a Mel-spectrogram. For Method 3.1, the images are flipped horizontally, along an imaginary vertical axis that passes through its center, such that a given pixel with coordinate (x, y) will now be situated at (width−x−1, y). For Method 3.2, the images are flipped vertically along a centered horizontal axis, such that a given pixel with coordinates (x, y) will now be situated at (x, height−y−1). FIG. 5 shows illustrative examples of a horizontally flipped and vertically flipped spectrogram image.

Color-Space Transformations—Methods 4.1, 4.2 and 4.3

To create synthetic heart sound spectrograms using color-space transformations, the real heart sounds are first converted into Mel-spectrograms. Then, each image was transformed into its RGB representation, allowing for the extrapolation of other color-space values using pre-established conversion factors and mathematical operations. For example, in an RGB-to-HSV transformation, the red, green, and blue values which range from ([0,255]) for each pixel, are converted into hue ([0°,360°]), saturation ([0-100%]), and value/brightness ([0-100%]) using the following formulas:

$$R' = \frac{R}{255}$$

$$G' = \frac{G}{255}$$

$$B' = \frac{B}{255}$$

$$C_{max} = MAX(R', G', B')$$

$$C_{min} = MIN(R', G', B')$$

$$\Delta = C_{max} - C_{min}$$

$$H = \begin{cases} 60° \times \left(\frac{G' - B'}{\Delta} \bmod 6\right), & C_{max} = R' \\ 60° \times \left(\frac{B' - R'}{\Delta} + 2\right), & C_{max} = G' \\ 60° \times \left(\frac{R' - G'}{\Delta} + 4\right), & C_{max} = B' \end{cases}$$

$$S = \begin{cases} 0, & C_{max} = 0 \\ \frac{\Delta}{C_{max}}, & C_{max} \neq 0 \end{cases}$$

$$V = C_{max}$$

Within the scope of color space transformations, three modalities of data augmentation were explored. Method 4.1 created new images from saturation and value perturbations. Method 4.2 created new images from PCA color augmentation. Method 4.3 created new images from applying random color filters.

In Method 4.1, two numbers, $\alpha_{brightness}$ and $\alpha_{saturation}$, were randomly drawn from a uniform distribution X~U(a, b). Experimentally, it was determined that the $\alpha_{brightness}$ would be bounded by a=0.5 and b=2, and $\alpha_{saturation}$ by a=0.1 and b=2. $\alpha_{brightness}$ and $\alpha_{saturation}$ control the degree of brightness and saturation perturbations, respectively. The merging operation can be described with the following formula:

Blending Image*(1−α)+Original Image*α

Brightness alterations were achieved by blending the original image with a pure black image of the same dimensions. Saturation alterations were achieved by blending the original image with a grey-scale image of the same dimensions. The two perturbations were applied sequentially to the original image, and the adjustment factors $\alpha_{brightness}$ and $\alpha_{saturation}$ were redrawn for each input spectrogram.

In Method 4.2, PCA was implemented on the unaltered input images, yielding a sorted set of eigenvectors and eigenvalues that are associated with the 3×3 covariance matrix of the RGB color channels. A random variable a is drawn from the normal distribution X~N($\mu$, $\sigma^2$), where $\mu$=800, $\sigma$=10, and multiplied to the original eigenvalues. The principal components are scaled by the output from the previous step, and the product is added to the RGB vector of each individual pixel. $\alpha$ is drawn once for each training image. The specific mean and standard deviation values of the perturbation were chosen experimentally, to intentionally produce more pronounced differences in the output images.

In Method 4.3, iteration through a library of 150 different color-space conversions was performed using the OpenCV package, effectively generating random color balance perturbations, but preserving the underlying shapes and content of the input images. The transformed Mel-spectrograms are used to supplement the Mel-spectrograms from real heart sounds as additional training data.

Time and Frequency Masks—Method 5

To create synthetic heart sound data using time and frequency masks, the real heart sounds are left untouched and converted to Mel-spectrogram images. To the Mel-spectrogram image, three masks are randomly applied in the time domain, and three masks are randomly applied in the frequency domain, in the manner described elsewhere herein. The location of the masks is chosen independently, meaning it is possible for masks to overlap and merge into one larger mask. The transformed Mel-spectrogram images are used to supplement the Mel-spectrogram images derived from real heart sounds to train the convolutional neural network. FIG. 4 shows a spectrogram with time and frequency masking applied.

Results of experiments performed using the above-described data augmentation techniques will now be described.

Reported metrics are based on a stratified 10-fold cross validation. The folds are created in a consistent way across the different models. This serves to limit any potential variability in model performance that would be due to the underlying variability in the data itself. Test folds only contain real heart sounds.

The models utilized in performing the experiments are denoted Model 0, corresponding to a baseline model, and Model 1, Model 2, Models 3.1 and 3.2, Models 4.1, 4.2 and 4.3, and Model 5, corresponding to the various data augmentation methods described above, but each using the CNN configuration illustrated in FIGS. 6 and 7.

The training of the different models was performed as follows.

Model 0 was trained on real data.

Model 1 was trained on real and synthetic data from Method 1.

Model 2 was trained on real and synthetic data from Method 2.

Models 3.1 and 3.2 were trained on real and synthetic data from Methods 3.1 and 3.2, respectively.

Models 4.1, 4.2 and 4.3 were trained on real and synthetic data from Methods 4.1, 4.2 and 4.3, respectively.

Model 5 was trained on real and synthetic data from Method 5.

Table 1 below shows average performance of each model according to accuracy, sensitivity, specificity and the ROC AUC, where ROC denotes receiver operating characteristic, and AUC denotes area under the curve.

TABLE 1

| | Accuracy (±Stdev) | Specificity (±Stdev) (at 90% Sensitivity) | ROC AUC (±Stdev) |
|---|---|---|---|
| Model 0 Baseline | 89.7% (1.7) | 86.6% (3.8) | 0.945 (0.016) |
| Model 1 Pitch/time alterations | 88.2% (2.4) ↓ | 82.3% (4.7) ↓ | 0.926 (0.013) ↓ |
| Model 2 Noise Injection | 88.6% (2.1) ↓ | 82.2% (6.2) ↓ | 0.929 (0.021) ↓ |
| Model 3.1 Horizontal Flip | 90.2% (1.8) ↑ | 90.8% (2.7) ↑ | 0.957 (0.009) ↑ |

TABLE 1-continued

|  | Accuracy (±Stdev) | Specificity (±Stdev) (at 90% Sensitivity) | ROC AUC (±Stdev) |
|---|---|---|---|
| Model 3.2 Vertical Flip | 89.2% (2.7) ↓ | 79.5% (6.9) ↓ | 0.919 (0.017) ↓ |
| Model 4.1 SV Perturbations | 90.6% (1.7) ↑ | 80.3% (26.9) ↓ | 0.946 (0.019) ↑ |
| Model 4.2 PCA Color Augmentation | 89.2% (2.2) ↓ | 87.8% (4.3) ↑ | 0.949 (0.014) ↑ |
| Model 4.3 Random Color Filters | 87.4% (3.0) ↓ | 81.4% (7.0) ↓ | 0.927 (0.024) ↓ |
| Model 5 Time/Frequency Masking | 89.5% (1.7) ↓ | 86.2% (5.1) ↓ | 0.948 (0.012) ↑ |

In these experiments, an example CNN model as illustrated in FIGS. 6 and 7 was utilized to classify cardiac sound recordings as either normal or abnormal. The baseline control model achieved an ROC AUC of 0.945±0.016. Among the example data augmentation techniques explored, horizontal flipping of the spectrogram image improved the model performance the most in these illustrative embodiments, with an ROC AUC of 0.957±0.009. PCA color augmentation and perturbations of saturation-value (SV) of the hue-saturation-value (HSV) color scale achieved an ROC AUC of 0.949±0.014 and 0.946±0.019, respectively. Time and frequency masking resulted in an ROC AUC of 0.948±0.012. Pitch shifting, time stretching and compressing, noise injection, vertical flipping, and applying random color filters all negatively impacted model performance.

An objective of these experiments was to identify optimal forms of data augmentation for illustrative embodiments in the binary classification of PCG signals using their spectral image representation. The baseline CNN model achieved specificity of 86.6% at 90% sensitivity, and a ROC AUC of approximately 0.95. As previously discussed, one of the unique challenges of heart sound augmentation is that the generated samples should fulfill the physiological constraint to remain meaningful. More explicitly, the rate, rhythm, and pitch of cardiac sounds are bounded within a narrow range. Values that fall outside of these limits would be unrealistic, and hence detract from the classification. Additionally, the original spectral components of the heart sounds should be maintained to ensure that a normal sound does not become pathological. The presence or absence of frequency components like murmurs, rubs, and S3 or S4 gallops should be preserved through these transformations. Secondly, the spectrogram constraint stems from the fact that spectrograms and photographs fundamentally convey different information along their respective dimensions. Image data augmentation methods tend to work best for spectral images if they correlate with realistic physical variations in the sound.

The example data augmentation method that satisfied both the physiological constraint and the spectrogram constraint improved model performance in illustrative embodiments, while the example data augmentation methods that failed to satisfy at least one of the constraints worsened model performance in some respect in illustrative embodiments, experimentally supporting the disclosed theoretical framework. In the following, a rationale is provided for why each data augmentation method either improved, did not effect, or worsened model performance in illustrative embodiments using the disclosed theoretical framework.

The first example data augmentation method was pitch shifting and time stretching/compressing, also referred to as Method 1. Since this augmentation is done at the audio level, the spectrogram constraint does not apply. Natural pitch variations reflect different anatomical variations of the heart including differing myocardium wall thickness, body fat/water composition, patient bone/rib structure, and the actual heart size, all of which may lead to variabilities in heart sound attenuation. The data augmentation technique of pitch shifting aims to capture these natural variations. There is also variability in how fast the heart beats. Time stretching and compressing represents heart sounds at different heart rates, such as in tachycardia or bradycardia.

Although pitch shifting and time stretching/compressing as data augmentation techniques reflects possible physiological variations, experimentally worsening model performance is seen when these data augmentation techniques are applied. At first this seems to contradict the theoretical framework because the physiological constraint is supposedly satisfied. However, considering that the natural heart sound exists within a very narrow physiological range, it is likely that the upper and lower limits of the pitch shifting and time stretching/compressing may have pushed the audio outside the normal physiological range. Thus, the physiological constraint was not actually satisfied because this augmentation technique created sounds that would never exist clinically, which is consistent with the worsening model performance.

The second example data augmentation method was noise injection, also referred to as Method 2. Noise injection has a regularization effect that can improve model performance by reducing overfitting and is a widely used audio data augmentation method for improving model performance. This augmentation is also done at the audio level, so again the spectrogram constraint does not apply. Despite the known ability of noise injection for improving model performance, it is observed that noise injection actually worsens model performance for heart sound spectral image classification. This can be understood from the fact that the fundamental difference between normal and abnormal heart sounds is that the latter has additional frequency components (e.g., murmurs, rubs, S3 gallops, S4 gallops). By definition, noise injection is the act of introducing new frequency components to an audio file. Thus, noise injection is essentially converting normal heart sounds into abnormal heart sounds. Noise injection fails to satisfy the physiological constraint because it ruins the distinction that separates normal and abnormal heart sounds.

The next set of example data augmentation methods involve horizontally and vertically flipping the spectrogram image, also referred to as Method 3.1 and Method 3.2, respectively. Horizontal flipping improved model performance on all three counts, while vertical flipping worsened model performance on all three counts. This is explained by the fact that information conveyed by sound is encoded in the frequency domain, which is represented on the y-axis of spectrogram images. This is an important distinction from traditional images, where the y-axis represents a physical distance. Although vertical flipping has been shown to be an effective augmentation technique for improving model performance on many image datasets such as ImageNet and CIFAR-10 (which consist of images of commonplace objects like dogs, cats, cars, etc.), a vertical flip is not appropriate for a spectrogram image in some embodiments. Transformations of the y-axis of spectrograms would scramble the frequency content of the sound, rendering any meaningful information that was encoded in the sound to be lost. A vertical flip has no physical correlation, and so does not satisfy the spectrogram constraint. In fact, the vertical flip worsened model performance the most out of all the example data augmentation techniques explored in these experiments performed on illustrative embodiments, underscoring the importance of not distorting the y-axis of spectrogram images.

Horizontal flipping leaves the frequency axis intact, so it satisfies the spectrogram constraint. A horizontal flip alters the temporal relationships of the frequency components, but as discussed above, a normal and pathological heart sound mostly contain the same frequency components (S1, S2, systole, diastole). The major difference is the presence or absence of other frequency components such as murmurs. It is not so much the temporal relationship of these frequency components with each other that help discern a normal heart sound from a pathological one. Thus, horizontal flips satisfy the physiological constraint as well, and experimentally it is observed that horizontal flips improve model performance the most out of the example data augmentation methods explored in these experiments. Horizontal flipping as a data augmentation technique is most likely unique to heart sound spectral images compared to many other audio classification problems that represent sound as spectral images, owing to the rhythmic nature of heart sounds. In other audio classification tasks such as speech recognition, the temporary relationship of the different frequency components is important, and thus a horizontal flip would most likely hinder model performance.

The next set of example data augmentation methods involve various color space transformations, also referred to as Method 4.1, Method 4.2 and Method 4.3. Although these transformations do not distort the frequency axis of the spectrogram, it is important to keep in mind the role of color as an additional dimension in spectrogram images. In a regular photo, color represents the wavelength of light reflecting off an object. In a spectrogram, color represents the loudness/intensity of the signal measured in decibels. Factors that contribute to the natural variation in heart sound amplitudes (e.g., how loud the heart sound is) include the size and position of the heart in the mediastinum, the presence of fluid within or fibrous thickening of the pericardium, and the position and extent of aeration of the lungs. For example, heart sounds are usually loudest at the apex where the heart is in direct contact with the anterior wall of the thorax. Younger patients tend to have louder heart sounds due to elastic and thin chest walls, whereas older patients tend to have quieter heart sounds due to stiffer and thicker chest walls. Heart sounds are louder when the patient is in full expiration, and quieter when the patient is in full inspiration. The example data augmentation techniques involving color space transformations aim to capture these variations.

Experimentally, it was observed that SV (Method 4.1) and PCA (Method 4.2) did not lead to statistically significant improvements in model performance, while adding random color filters (Method 4.3) unequivocally worsened model performance. Neither SV (Method 4.1) nor PCA (Method 4.2) introduces temporal or spectral distortions to the underlying image, thus satisfying the spectrogram constraint. However, specificity post-SV augmentation worsened significantly, likely due to the unconstrained shading changes to the spectrogram, which translates to drastic alterations of loudness/intensity at the audio level. The model is less able to identify "normal" heart sounds due to the sheer amount of unnatural variations in the training set that were labeled as normal based on the lack of murmurs.

In contrast, incorporation of PCA data in the training set improved sensitivity and ROC AUC at the expense of a minor decrease in accuracy, and overall appears to be the second-best data augmentation method for cardiac analysis next to horizontal flip. At root, PCA establishes new features, known as "principal components," from the original dataset. The goal is to compress the initial input dimensionality without compromising the most valuable information that were conveyed. Alterations along these principal components accomplish two objectives. First, they enrich the image along the axes of natural variation, which are by definition where the maximum between-sample variabilities exist. Second, since changes are made at the color level, the underlying object invariance is maintained, which preserves the temporal and spectral properties of the original spectrograms. While intensity changes are unpredictable in SV because they are randomly generated, PCA's perturbations were derived mathematically, though still unconstrained by human physiological limits. Therefore, PCA suffers a similar pitfall as SV, though the detrimental effects are arguably much more blunted because the physiological constraint is satisfied to a greater extent.

In contrast to the previous two techniques, random color filters entirely shift the hues outside the scope of a predetermined color-axis (e.g., orange). This may work for images of commonplace objects like cars, which can be observed in a wide variety of colors, but these augmentations are nonsensible for heart sound spectrograms as they have no associated physical meaning. The spectrogram constraint is severely violated, and experimentally it is observed that multicolor filters worsen model performance to the largest degree on all three counts. It is also important to note that in addition to the natural variations in heart sound amplitudes, changes in amplitude may also reflect clinically relevant information. Pathological conditions such as cardiac tamponade classically lead to diminished heart sounds. Pleural effusions, subcutaneous edema, pneumothorax, and chronic obstructive pulmonary diseases (COPD) such as emphysema would also muffle heart sounds, although in these conditions the heart itself would be considered healthy. Similar to noise injection, alterations in heart sound amplitude could potentially blur the distinction between normal and abnormal heart sounds, which would worsen model performance. Epidemiologically, distant heart sounds from tamponade, pneumothorax, or COPD that is severe enough to muffle heart sounds are much rarer than murmurs. The majority of abnormal heart sounds in the example dataset are characterized by murmurs rather than distant heart sounds, explaining why amplitude perturbations did not have as much as a deleterious effect compared to noise injections.

The fifth augmentation method is time and frequency masking, also referred to as Method 5. Masking induces partial information loss at random points in the time and frequency domain. It is possible that masking has a similar effect to the regularization technique of dropout, where randomly selected neurons are ignored during training. However, in clinical practice, sudden quiescent periods occur in diseases such as AV heart block, cardiac arrest, or sick sinus syndrome. The original labels are preserved, so images that sprung from masking of normal spectrograms are still labeled as normal, despite the introduction of sudden pauses. Hence, masking does not satisfy the physiological constraint and it is observed that model performance is not improved. Unlike noise injection and similar to amplitude changes, this type of pathological heart sound is relatively rare, thus there is no drastic reduction in performance. This stands in contrast to the state-of-the art results that masking has achieved in automated speech recognition, further illustrating the distinction between clinical sound analysis and traditional audio processing.

These experimental results from illustrative embodiments corroborate techniques disclosed herein for heart sound spectrogram classification. Methods that violated the spectrogram constraint, such as vertical flipping and applying random color filters, worsened model performance by the greatest extent. Among the methods that did not violate the spectrogram constraint, the degree to which the physiological constraint was adhered to correlated with how much model performance improved or worsened. Noise injection is not a safe operation in some embodiments because the fundamental distinction between normal and abnormal heart sounds is blurred since the majority of abnormal heart sounds (murmurs, gallops, rubs) are just normal heart sounds with additional frequency components. Amplitude variation (via sensible color space transformations) and masking are also limited by fact that the distinction between normal and abnormal heart sounds are blurred: heart sounds with decreased amplitudes can be found in diseases such as cardiac tamponade, and heart sounds with quiescent periods can be found in diseases such as AV block. However, these augmentation methods are less fatal compared to noise injection because epidemiologically these heart sounds are much rarer, explaining the absence of a drastic reduction in model performance compared to noise injection. Pitch shifting and time stretching/compressing worsened model performance most likely because the alterations were outside physiological ranges. There is potential for this augmentation method to work, given that heart sounds naturally exist within a narrow physiologic range, by precisely defining these boundaries. Interestingly, horizontal flipping is not actually rooted in any true physiological variation but has proven to be the superior data augmentation method in these experiments involving illustrative embodiments. Horizontal flipping is able to create variation in the data without unnatural variations (such as at the extreme ends of pitch and time alterations) or run the risk of transforming normal sounds into abnormal sounds (such as with amplitude variations or masking).

The physiological constraint and spectrogram constraint described herein can be used as a guide for implementing additional or alternative data augmentation methods for heart sound classification based on their spectral image. Moreover, the ideas behind the physiological constraint can be extended to related techniques seeking to classify heart sounds, while the ideas behind the spectrogram constraint can be extended to related techniques using spectrograms to classify audio.

The above-described experiments demonstrate that there is value in data augmentation if done correctly, particularly for binary classification of PCG signals, and most likely for other medical classification problems as well. By synthetically generating samples using simple transformations, the existing reservoir of patient data is expanded, further enriching the documentation of select pathological conditions, which may be rare in nature and difficult to obtain. Machine learning models are increasingly used to streamline the repetitive processes in healthcare, such as initial screening, preliminary classifications, triage, patient sorting, and specialist recommendations. Data augmentation techniques as disclosed herein can improve model performance in cardiac sound analysis and are expected to provide similar improvements in other areas as well. In addition, this study corroborates the idea that models are only as good as the data from which it learns. Disease-appropriate forms of data augmentation are integral to improvements in model performance, and synthetic data is most meaningful when it lies within the scope of human physiology and can accurately mimic clinical findings. Hence, physician input should be considered when creating models, so these tools can be useful and pragmatic both empirically and at the bedside.

The experimental results described above relate to particular illustrative embodiments, and should not be construed as limiting the types and configurations of data augmentation techniques that can be applied in other embodiments. For example, one or more data augmentation techniques that were found in the above-described experimental results to not significantly improve performance in the particular embodiments in the particular biomedical acoustics context of heart sound classification, may improve performance in other embodiments and/or other biomedical acoustics contexts involving other types of sounds.

It should be noted that the particular data augmentation techniques described above and elsewhere herein are only examples, and additional or alternative data augmentation techniques can be used in other embodiments. Moreover, data augmentation techniques described herein in the context of spectrograms can be applied to other types of image representations, such as recurrence plots.

Additional illustrative embodiments of biomedical acoustics classification will now be described with reference to FIGS. 10 through 12.

In some embodiments, additional or alternative image representations are used that are not spectrograms. The term "image representation" as used herein is therefore intended to be broadly construed, and should not be viewed as being limited to spectrograms.

For example, in some embodiments, the image representations comprise respective recurrence plots. In such embodiments, sound is treated as time series data and recurrence plots are generated for the sound. A given such recurrence plot illustratively provides a visualization or graph of data of a square matrix, in which the matrix elements correspond to those times at which a state of a dynamic system recurs, with the columns and rows corresponding to a particular pair of times.

Biomedical sounds, such as heart sounds, blood flow sounds, and lung sounds, typically have a natural recurring rhythm. For example, heart sounds cycle through the four phases S1, systole, S2, diastole. Blood flow sounds are produced by the heart cycling through systole and diastole. Lung sounds cycle through an inspiratory and expiratory phase. A recurrence plot of these biomedical sounds is illustratively in the form of an image that depicts the rhythmic nature of a trajectory vector $\vec{x}$ through a phase space. The recurrence plot illustratively visualizes the set of all pairs in time $(t_n, t_m)$ in which $\vec{x}(t_n) = \vec{x}(t_m)$.

In some embodiments, a recurrence plot for biomedical sounds is constructed in the following manner. Let $T = \{t_0, t_1, t_2, \ldots t_n \ldots t_N\}$ represent the discretized time points over which the audio signal spans, separated by the time interval $\delta$. The trajectory of the audio signal through the phase space is given by $\vec{X} = \{\vec{x}(t_0), \vec{x}(t_1), \vec{x}(t_2), \ldots \vec{x}(t_n) \ldots \vec{x}(t_N)\}$. The recurrence states of $\vec{x}(t_n)$ are states $\vec{x}(t_m)$ that fall within a given radius $\varepsilon$ around $\vec{x}(t_n)$. The recurrence plot is constructed as an N×N lattice of squares with side length $\delta$ and with each coordinate axis reporting T. The value at coordinates $(t_n, t_m)$ is given by the recurrence value function $R(t_n, t_m)=\Theta(\varepsilon-\|\vec{x}(t_n)-\vec{x}(t_m)\|)$, where $\Theta$ is the Heaviside step function. Other types of recurrence plots can be used in other embodiments.

The recurrence plot exhibits characteristic large scale and small scale patterns that can be used to classify sounds (e.g., innocent vs. pathologic heart murmur). For example, single isolated reoccurrence points occur if certain states of the phase space are rare (e.g., a recording artifact). Diagonal lines mean the evolution of states is similar at different times. Vertical and horizontal lines mean that states do not change or change slowly over time (e.g., the sound of laminar blood flow through a patent vessel). Diagonal lines juxtaposed to single isolated points means state is not deterministic (e.g., the sound of turbulent blood through a stenotic vessel). A recurrence plot image representation of sound can be used to train a CNN to classify sounds based on these recurrence plot image patterns.

It should be noted that the various data augmentation techniques described herein in the context of spectrograms can be similar applied to recurrence plots, and to other types of image representations. Accordingly, the disclosed data augmentation techniques should not be viewed as being limited in any way to spectrograms, recurrence plots or other particular types of image representations.

Figure 10A:
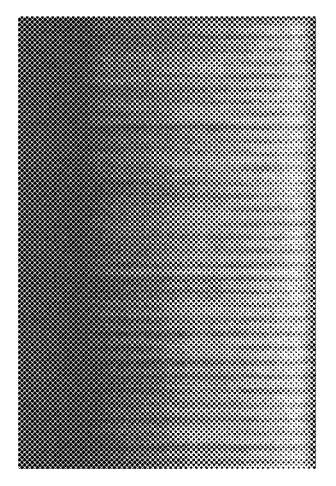
FIGS. 10A and 10B show example recurrence plots and corresponding spectrograms for two different pediatric heart sounds. These figures are collectively referred to herein as FIG. 10.
Figure 10B:
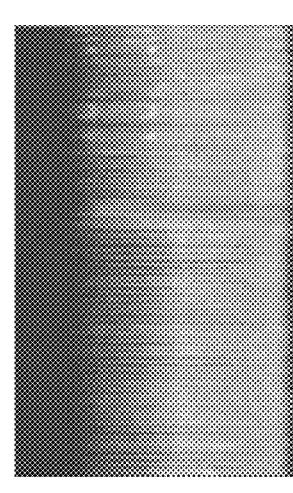
Figure 10B:
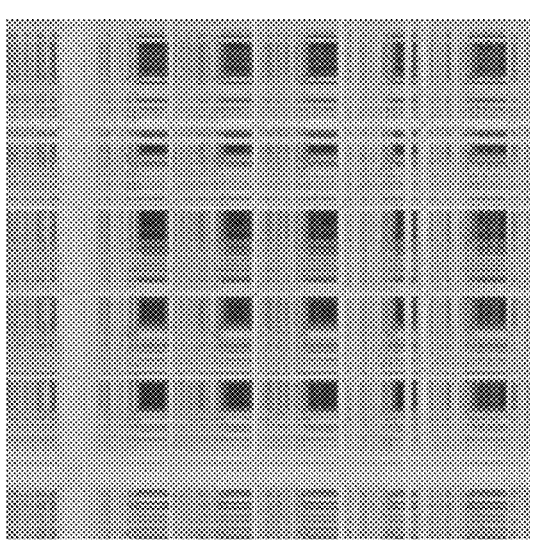

FIGS. 10A and 10B show recurrence plots and spectrograms for two different pediatric heart sounds. FIG. 10A shows a recurrence plot image representation on the left side of the figure, and a corresponding spectrogram image representation on the right side of the figure, for a normal pediatric heart sound. FIG. 10B shows a recurrence plot image representation on the left side of the figure, and a corresponding spectrogram image representation on the right side of the figure, for a ventral septal defect pediatric heart sound.

In some embodiments, representing sound as a recurrence plot image for CNN classification may outperform representing sound as a spectrogram image for certain tasks such as murmur classification.

For example, as is apparent from FIGS. 10A and 10B, the difference between a normal and pathological sound is much more visually apparent in the recurrence plots than in the corresponding spectrograms.

Other types and arrangements of recurrence plots, or other image representations, can be used in other embodiments. Accordingly, illustrative embodiments herein are not limited to use with spectrograms or other particular image representations.

Figure 11:
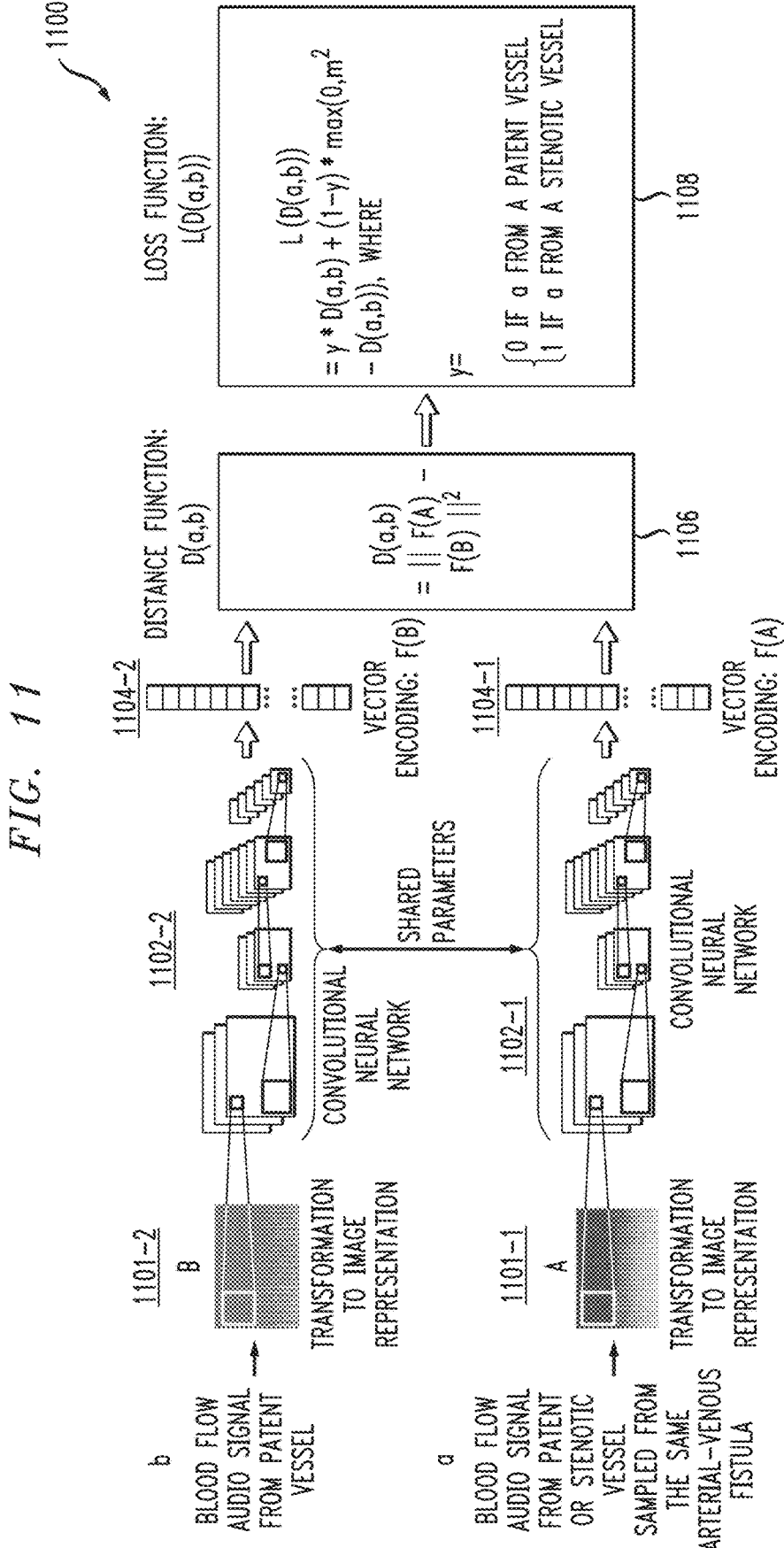
FIGS. 11 and 12 are block diagrams of other example biomedical acoustics classifiers in illustrative embodiments.
Figure 12:
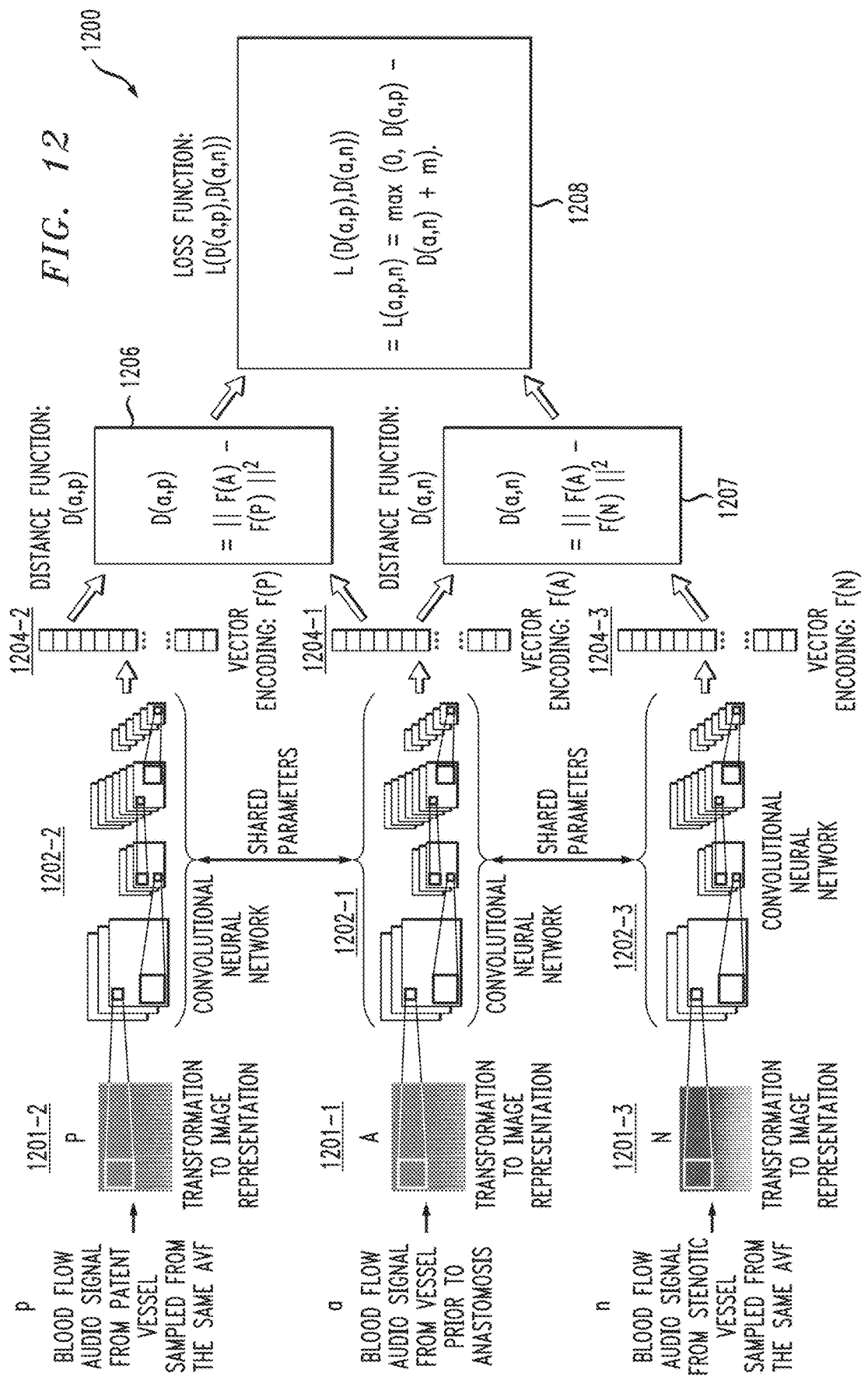

FIGS. 11 and 12 illustrate example biomedical acoustics classifiers 1100 and 1200 particularly configured to detect arteriovenous fistula (AVF) stenosis via blood flow sounds. These classifiers are also adaptable for use in other contexts, such as in detecting blood flow issues relating to grafts.

Patients with chronic renal failure who need hemodialysis will have an AVF or graft created where viable. There are multiple types of fistulas that can be created between the vessels in the arm, depending on the individual's anatomy and vessel sizes and patency. Most commonly, the radial or brachial artery is connected to the cephalic vein. The purpose of the AVF is to create an engorged vein to allow for easier access during dialysis and to create higher blood flow within the vein to ensure that largest amount of blood can pass through the dialyzer.

Fistula failure is a well-known vascular complication of AVFs. The mechanism of AVF failure is failure to mature, stenosis formation, or thrombosis of the AVF. The North American Vascular Access Consortium reported that the overall estimated risk of AVF failure is 23% in the general hemodialysis patient population, and 37% in the elderly. Routine screening of AVF and graft integrity in an ultrasound lab is therefore necessary for hemodialysis patients for early detection and intervention in the event of fistula failure.

In the event an AVF or graft fails, and dialysis is needed in the interim, the next step is placement of a central venous catheter (CVC) for dialysis access, which exposes patients to the increased mortality and morbidity associated with CVCs. Compared to AVFs and grafts, CVCs have a high risk of complications, with a cumulative risk of catheter-related complications of 30% in 1 year, and 1-year risk of bacteremia of 9%. Other important complications of AVF or graft failure that necessitate early surgical or endovascular intervention include infection, aneurysm, congestive heart failure, ischemic neuropathy, and thrombosis.

Illustrative embodiments disclosed herein provide machine learning models that can correctly identify fistula failure from blood flow sounds through the AVF, which automates the aforementioned screening process for hemodialysis patients, minimizing the resource burden needed to screen for fistula failure (e.g., vascular surgery consults, duplex ultrasound centers, and skilled lab techs). Not only will this improve patient quality of life by saving HD patients a trip to the vascular lab, but more importantly, this has the potential to decrease the associated morbidity and mortality of AVF or graft failure by facilitating early detection of vascular access-related complications.

Such embodiments advantageously provide a new standard of care in dialysis. Currently, patients with dialysis access complications are at two opposite ends of the spectrum of care. In resource deficient areas, dialysis patients have a significant burden of care—in addition to dialysis for several hours a day three times a week, they have several other appointments with doctors every year, including screening of their vascular access site every three months. Patient compliance for these screening appointments is therefore often low; patients are understandably unwilling to spend any additional time in the healthcare setting on top of their time spent in dialysis. In rural environments, the scarcity of facilities for detection and intervention poses an additional challenge. As a result, many are only detecting fistula complications once it's too late to salvage vascular access, and patients end up in situations where they need to be hospitalized for emergency dialysis access. In areas with an over-abundance of resources and high competition between providers, patients are being recommended for interventions on their existing fistulas every three months, regardless of the actual fistula status. Dialysis currently costs the US healthcare system on average $90,000 per patient per year. A single emergency hospitalization can cost up to $50,000. Early detection of AVF stenosis or thrombosis would reduce these costs significantly.

Additional details regarding example approaches for detecting AVF stenosis using neural network processing of image representations of blood flow sounds will now be described. These example approaches include a classification learning approach and a similarity learning approach, and although described primarily in the context of AVFs are applicable to grafts and other blood flow contexts.

The classification approach utilizes techniques similar to those previously described in conjunction with FIGS. 2 through 9. For example, in the classification approach, blood flows sounds are acquired from various anatomical locations (e.g., brachial artery, anastomosis of the artery and vein, distal upper arm cephalic vein, mid upper arm cephalic vein, proximal upper arm cephalic vein, and cephalic arch). The recorded sounds are classified as either patent or stenosed based on duplex ultrasound findings, which validates the data and provides the ground truth label. The sounds are converted into respective image representations in the manner previously described. Additional image representations can be generated using one or more of the data augmentation techniques disclosed herein, such as masking, GAN, horizontal flipping, etc. The image representations (both real and synthetic) are used to train a CNN for classification. At run time, the trained CNN can be used to classify blood flow sounds through AVFs as patent or stenotic. In this context, the term "patent" generally refers to normal or non-stenotic, but is intended to be broadly construed.

The similarity learning approach uses the previously-described techniques for CNN processing of image representations of sound as a core building block for a more elaborate machine learning model.

The example model in similarity learning embodiments is illustratively configured to determine how similar or dissimilar a given blood flow sound is compared to a reference blood flow sound. The reference blood flow sound comes from a point along the patient's vasculature that is already known to be patent. Blood flow sound from any point of interest along the AVF is compared to the reference sound. If the two sounds are determined to be similar by the example model, then that point of interest along the AVF from which the non-reference sound was derived from is considered patent. If the two sounds are determined to be dissimilar by the example model, then that point along the AVF which the non-reference sound was derived from is considered stenotic.

An advantage of this similarity learning approach is that it is more robust against the natural physiologic variation that exists from patient to patient. This approach emulates the actual clinical practice of how the patency status of AVFs is determined, which involves a relative comparison of the blood flow speed as measured by duplex ultrasound in the context of the patient's specific vasculature. For example, a blood flow speed of 550 ml/min is in of itself not an indicator for stenosis, but if the blood flow speed along other points of the patient's vasculature is only 150 ml/min, then that point where the blood flow speed is 550 ml/min is most likely stenotic. For a different patient where the blood flow speed measures 550 ml/min throughout the AVF, it is likely that the vasculature is patent throughout. Natural physiological variation that affects the speed and sound of blood flow from patient to patient include heart rate, diameter of the vessel, elasticity of the vessel wall, degree of preexisting atherosclerosis, and viscosity of the blood, among others. Since patency status of a given point in the vasculature is determined by comparison to a point in the vasculature that is already known to be patent from the same patient, all these confounding factors are controlled for.

Blood flow sounds are acquired from various anatomical locations (e.g., brachial artery, anastomosis of the artery and vein, distal upper arm cephalic vein, mid upper arm cephalic vein, proximal upper arm cephalic vein, and cephalic arch). The recorded sounds are classified as either patent or stenosed based on duplex ultrasound findings, which validates the data and provides the ground truth label. The sounds are converted into respective image representations in the manner previously described. Additional image representations can be generated using one or more of the data augmentation techniques disclosed herein, such as masking, GAN, horizontal flipping, etc.

The example model in some embodiments comprises a set of multiple CNNs arranged in parallel with one another. The number of CNNs in parallel illustratively depends on the loss function used.

All the CNNs in parallel illustratively share exactly or substantially the same learnable parameters (e.g., weights and biases) that are updated with the same values during model training and share exactly or substantially the same hyperparameters (e.g., number of hidden units and learning rate). The output of a given one of the CNNs is illustratively a vector encoding of the corresponding input image.

A distance function is illustratively used to determine how similar the blood flow sounds are to each other based on how close together their vector encodings are in the feature space. Any of a wide variety of distance functions can be used in the disclosed embodiments.

The loss function is illustratively defined in terms of the distance function. The loss function in some embodiments guides how the model parameters are updated during training such that the distance function is minimized for image representations of sound that are similar and such that the distance function is maximized for image representations of sound that are dissimilar. Like the distance functions, any of a wide variety of loss functions can be used in the disclosed embodiments.

Examples of the similarity learning approach are implemented in the respective biomedical acoustics classifiers 1100 and 1200 of respective FIGS. 11 and 12.

FIG. 11 illustrates an embodiment in which a contrastive loss function is used and the example model comprises two CNNs 1102-1 and 1102-2 in parallel. The two parallel CNNs 1102-1 and 1102-2 process respective image representations 1101-1 and 1101-2 as illustrated in the figure. Outputs of the CNNs 1102-1 and 1102-2 are subject to vector encoding in respective vector encoding components 1104-1 and 1104-2, with the encoded results from these components being applied as respective inputs to a distance function component 1106. The output of the distance function component 1106 is provided to a loss function component 1108 for generation of an output classification decision.

In the FIG. 11 embodiment, the model architecture of the biomedical acoustics classifier 1100 can be described mathematically as follows. Let a represent the blood flow audio signal sound coming from a portion of the AVF that is patent and let A represent the image representation of a. Let b represent the blood flow audio signal sound coming from a different portion of the AVF that is either patent or stenotic and let B represent the image representation of b. F(A) represents the vector encoding of image A as determined by the CNN 1102-1 and the vector encoding component 1104-1. F(B) represents the vector encoding of image B as determined by the CNN 1102-2 and the vector encoding component 1104-2. How similar a and b distance are to each other is determined by a distance function D(a, b) applied in the distance function component 1106. In some embodiments, the distance function is the L2 norm:

$$D(a,b)=\|F(A)-F(B)\|^2.$$

As shown in FIG. 11, the contrastive loss function applied in the loss function component 1108 is illustratively defined as:

$$L(a,b)=y*D(a,b)+(1-y)*\max(0,m^2-D(a,b)),$$

where

36

$$y = \begin{cases} 0 \text{ if } a \text{ is the blood flow audio signal coming from a patent vessel} \\ 1 \text{ if } a \text{ is the blood flow audio signal coming from a stenotic vessel} \end{cases}$$

and m is the margin, or minimum distance from the decision boundary. As indicated previously, other distance and loss functions can be used.

FIG. 12 illustrates an embodiment in which a triplet loss function is used and the example model comprises three CNNs 1202-1, 1202-2 and 1202-3 in parallel. The three parallel CNNs 1202-1, 1202-2 and 1202-3 process respective image representations 1201-1, 1201-2 and 1201-3 as illustrated in the figure. Outputs of the CNNs 1202-1, 1202-2 and 1202-3 are subject to vector encoding in respective vector encoding components 1204-1, 1204-2 and 1204-3, with the encoded results from different pairs of these components being applied as respective inputs to distance function components 1206 and 1207 as shown. The outputs of the distance function components 1206 and 1207 are provided to a loss function component 1208 for generation of an output classification decision.

In the FIG. 12 embodiment, the model architecture of the biomedical acoustics classifier 1200 can be described mathematically as follows. Let a represent the blood flow audio signal sound coming from a portion of the AVF that is patent and let A represent the image representation of a. Let P represent the blood flow audio signal sound coming from a different portion of the AVF that is also patent and let P represent the image representation of p. Let n represent the blood flow audio signal sound coming from a different portion of the AVF that is stenotic and let N represent the image representation of n. F(A) represents the vector encoding of image A as determined by the CNN 1202-1 and the vector encoding component 1204-1. F(P) represents the vector encoding of image P as determined by the CNN 1202-2 and the vector encoding component 1204-2. F(N) represents the vector encoding of image N as determined by the CNN 1202-3 and the vector encoding component 1204-3.

In some embodiments, the distance function utilized in the distance function components 1206 and 1207 is the L2 norm. Accordingly, how similar a and p are to each other is determined by the distance function:

$$D(a,p) = \|F(A) - F(P)\|^2.$$

How similar a and n are to each other is determined by the distance function:

$$D(a,n) = \|F(A) - F(N)\|^2.$$

As shown in FIG. 12, the triplet loss function applied in the loss function component 1208 is illustratively defined as:

$$L(a,p,n) = \max(0, D(a,p) - D(a,n) + m),$$

where m is the margin, or minimum distance from the decision boundary. As indicated previously, other distance and loss functions can be used.

Techniques for training the above-described example models will now be described in more detail.

In the FIG. 11 embodiment where the contrastive loss function is used and the model comprises two CNNs 1102-1 and 1102-2 in parallel, the input to the model is pairwise data, a and b, where a is the reference sound, which is illustratively sound known to be coming from a patent vessel. It can be guaranteed that a will represent sound coming from a patent vessel by using the point along the AVF before the anastomosis of the artery and vein. For example, in an AVF constructed from the brachial artery and cephalic vein, a can be sound from anywhere along the brachial artery. The data b is sounds collected at and downstream of the anastomosis, which can either be patent or stenotic. The pairwise data a and b used as input to train the CNN is illustratively sampled from the same AVF from the same patient at a particular point in time, although it is to be appreciated that additional or alternative training arrangements can be used.

In the FIG. 12 embodiment where the triplet loss function is used and the model comprises the three CNNs 1202-1, 1202-2 and 1202-3 in parallel, the input to the model is triple-wise data, a, p, n, where data a is the reference sound, which is illustratively sound known to be coming from a patent vessel. It can be guaranteed that a will represent sound coming from a patent vessel by using the point along the AVF before the anastomosis of the artery and vein. For example, in an AVF constructed from the brachial artery and cephalic vein, a can be sound from anywhere along the brachial artery. The data p is sounds from patent vessels collected at or downstream of the anastomosis. The data n is sounds from stenotic vessels collected at or downstream of the anastomosis. The triple-wise data a, p, n used as input to train the CNNs is illustratively sampled from the same AVF from the same patient at a particular point in time, although again it is to be appreciated that additional or alternative training arrangements can be used.

At run time, the trained CNNs are used to detect stenosis of AVFs in the manner previously described.

It is to be appreciated that the embodiments of FIGS. 11 and 12 are presented by way of illustrative example only, and numerous alternative arrangements can be used. For example, in other embodiments comprising a pair of CNNs arranged in parallel, similar to the CNN arrangement of FIG. 11, the input to the model illustratively comprises pairwise data, which can be characterized in this embodiment as a reference sound r and a sound of interest i. The reference sound illustratively comprises sound from a point prior to the anastomosis (e.g., from the brachial artery in a brachial artery-cephalic vein fistula). The sound of interest illustratively comprises sound from any point of interest along the AVF. A distance function is used to calculate how far apart the vector encodings are in the feature space. In some embodiments, the distance function is the cosine similarity function:

$$d(r, i) = \frac{d(r) \cdot F(i)}{\|F(r) \times F(i)\|}.$$

If d(r, i) is less than or equal to a certain threshold value t, the point of interest is patent. If d(r, i) is greater than t, the point of interest is stenotic.

Again, numerous other arrangements of one or more neural networks can be used in classifying image representations of biomedical acoustics in illustrative embodiments.

Additional illustrative embodiments of biomedical acoustics classification will now be described with reference to FIGS. 13 through 17.

Figure 13:
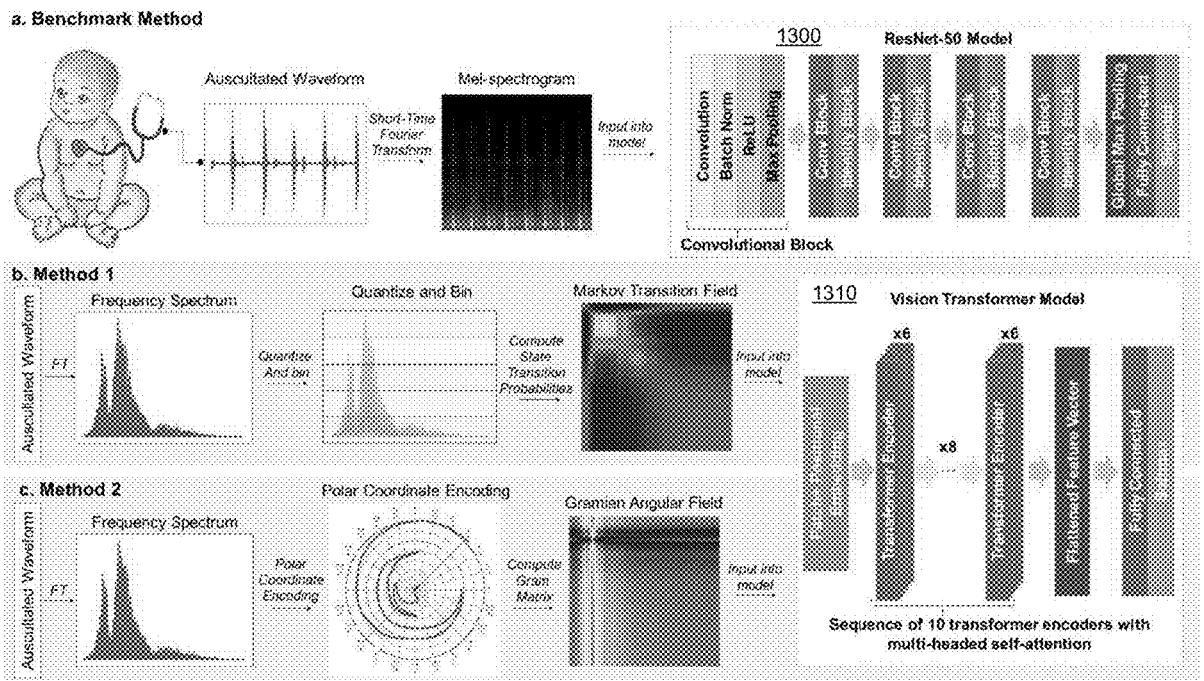
FIG. 13 illustrates the operation of example biomedical acoustics classifiers utilizing images comprising spectrograms, Markov transition fields and Gramian angular fields for pediatric heart sound classification in illustrative embodiments.
Figure 14:
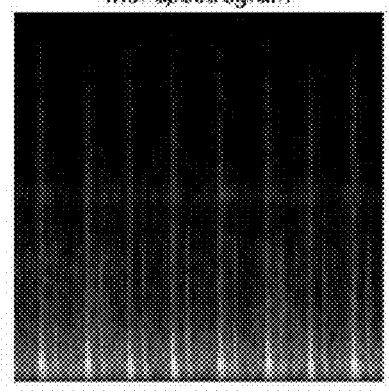
FIG. 14 shows example image representations comprising spectrograms, Markov transition fields and Gramian angular fields for each of a plurality of different types of pediatric heart sounds.
Figure 14:
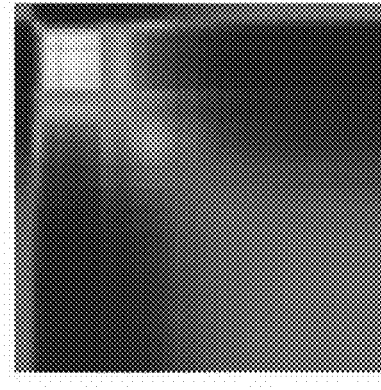
Figure 14:
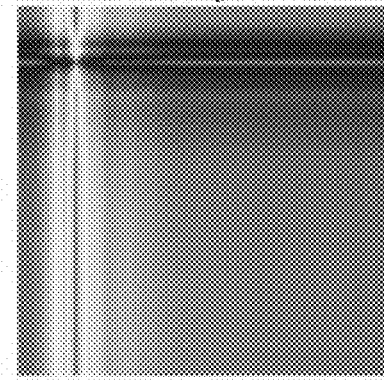
Figure 14:
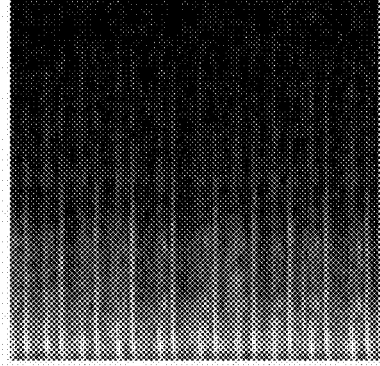
Figure 14:
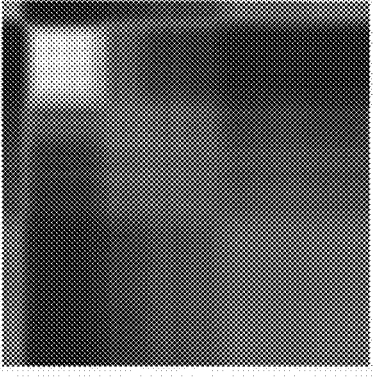
Figure 14:
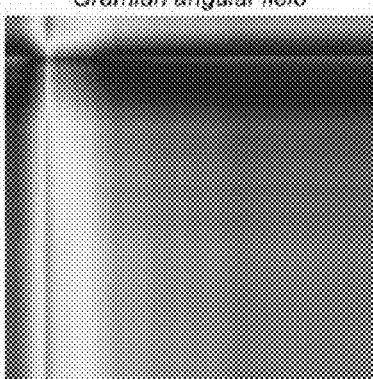
Figure 14:
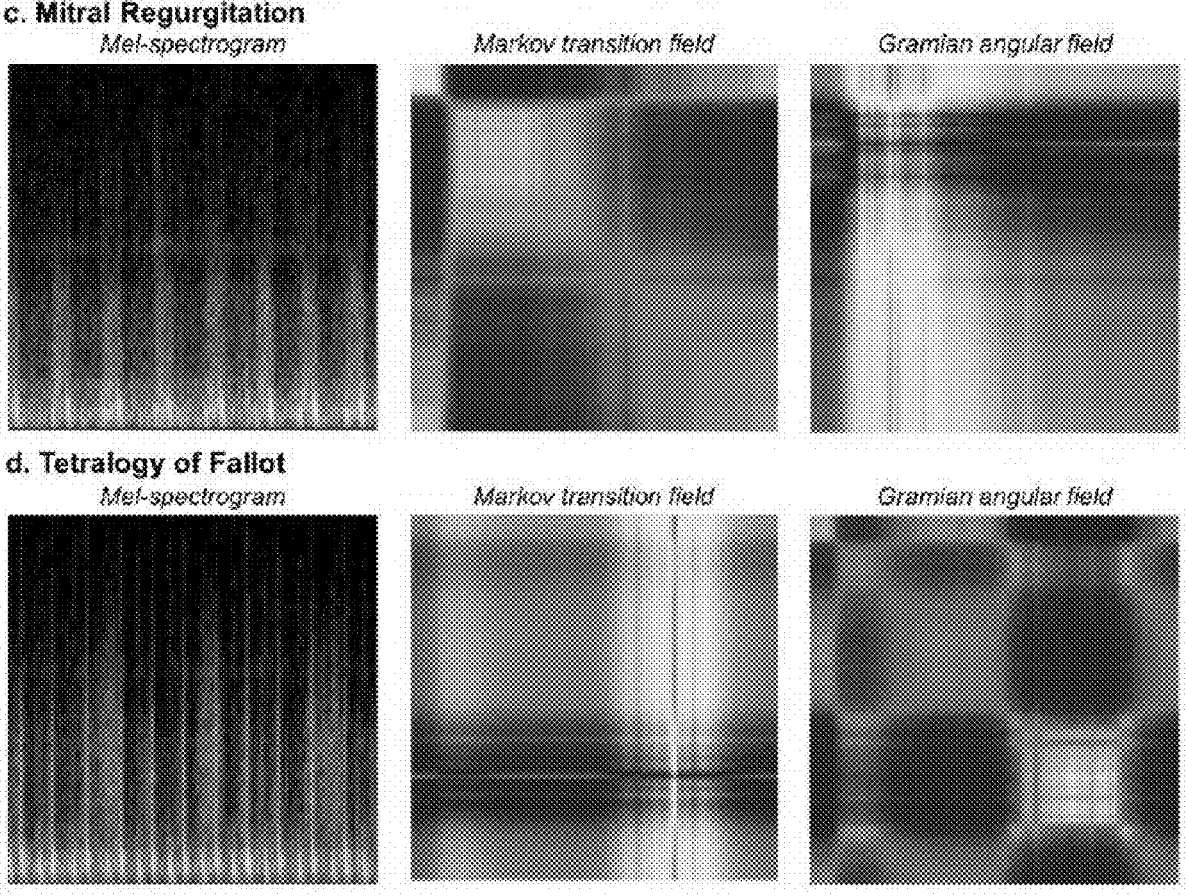
Figure 15:
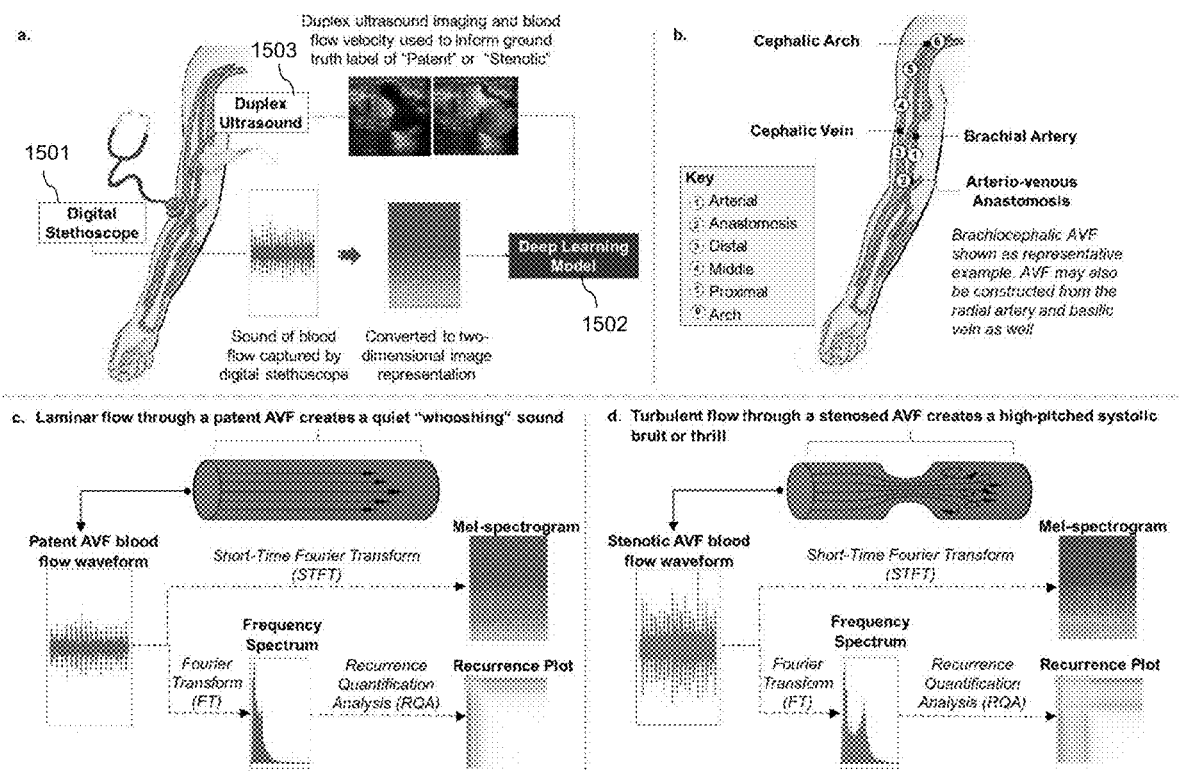
FIG. 15 illustrates the operation of example biomedical acoustics classifiers utilizing image representations comprising spectrograms and recurrence plots for blood flow sound classification in illustrative embodiments.
Figure 16:
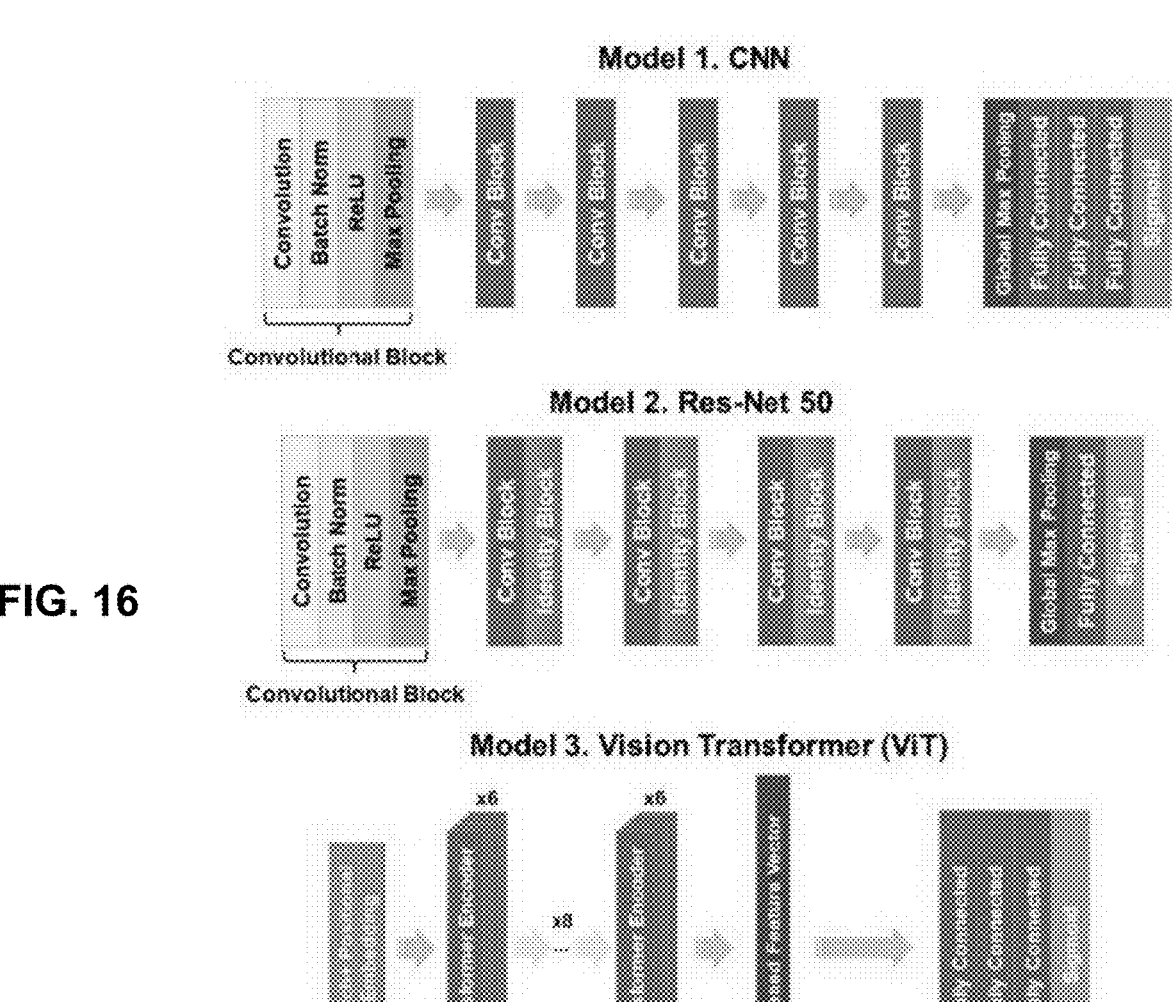
FIG. 16 shows examples of neural networks utilized in the example biomedical acoustics classifiers of FIG. 15 in illustrative embodiments.
Figure 17:
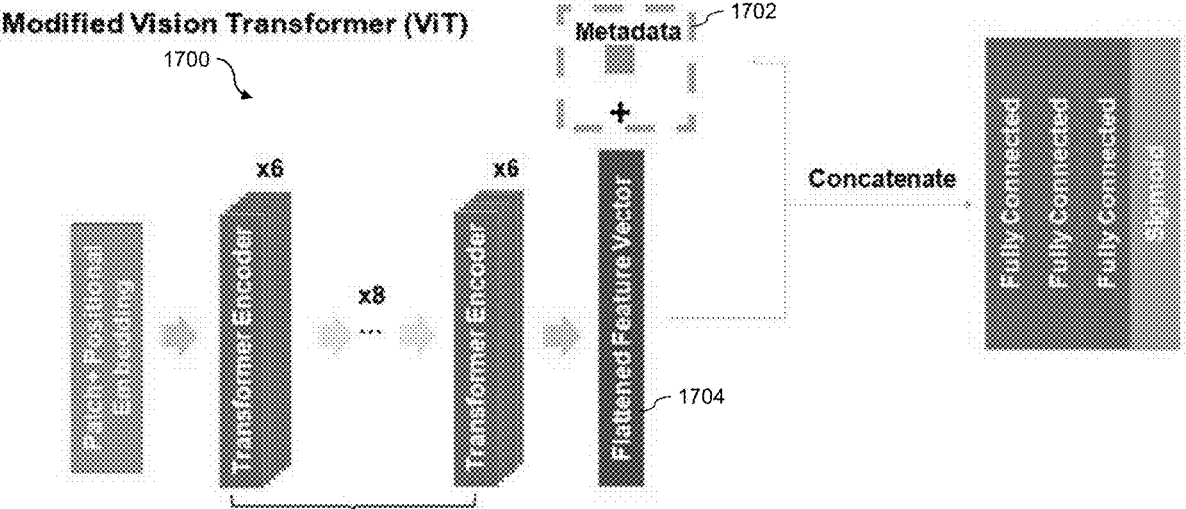
FIG. 17 shows another example of a neural network comprising a modified vision transformer in an illustrative embodiment.

The embodiments of FIGS. 13 and 14 are illustratively applied in the context of classification of pediatric heart sounds, and the embodiments of FIGS. 15 through 17 are illustratively applied in the context of classification of blood flow sounds, although it is to be appreciated that these and other arrangements disclosed herein are more broadly applicable to classification of a wide variety of other types of biomedical acoustics.

In some embodiments disclosed herein, generating an image representation comprises generating at least one Markov transition field (MTF) image representation of at least a portion of the acoustic signal in at least one of a time domain and a frequency domain.

Additionally or alternatively, in some embodiments, generating an image representation comprises generating at least one Gramian angular field (GAF) image representation utilizing at least one of (i) one or more trigonometric summations of at least a portion of the acoustic signal in a time domain, (ii) one or more trigonometric summations of at least a portion of the acoustic signal in a frequency domain, (iii) one or more trigonometric differences of at least a portion of the acoustic signal in the time domain, and (iv) one or more trigonometric differences of at least a portion of the acoustic signal in the frequency domain.

In some embodiments, generating the image representation comprises performing a channeling operation to concatenate at least one image representation along a channel dimension of the neural network where each channel of the channel dimension of the neural network processes a different one of a plurality of image representations. For example, input to a given neural network in an illustrative embodiment may comprise a three-dimensional (3D) volumetric cube of dimensions W×H×C, where W denotes width, H denotes height, and C denotes the number of channels of which each channel is a different image representation.

As indicated previously, illustrative embodiments disclosed herein can be configured to utilize a wide variety of different types of neural networks.

For example, some embodiments herein utilize a vision transformer ("ViT") configured to implement a self-attention mechanism, instead of or in addition to a CNN.

While image representations of sound (e.g., spectrograms, recurrence plots, MTFs, GAFs, etc.) and natural images are both images from a data structure point of view (i.e., a grid of pixel values), these two types of images represent fundamentally different natural phenomena. The inductive biases of translational invariance and locality structurally built into the CNN architecture are not as suitable for processing and interpreting image representations of sound. While translation invariance is a good assumption for natural images whose axes convey a measure of physical distance (i.e., a cat in the upper left corner is the same as a cat in the lower right corner), the same is not true for these images that depict frequency or frequency derived information along their axes. For example, in some embodiments a spectrogram illustratively conveys time on the x-axis and frequency on the y-axis. It may be a fair assumption that translational invariance applies to the time axis (e.g., a sound event happening at 5 seconds is the same as one happening at 10 seconds), but it does not make much sense to uphold translational invariance to the frequency axis because semantic meaning is encoded in the frequency domain. Furthermore, the spectral properties of sound are non-local. The pitch of a sound is determined by the fundamental frequency, while the quality or timbre of a sound is determined by its harmonics (the n-th harmonic has a frequency $F_n=nF_1$, where $F_1$ is the fundamental frequency). The fundamental frequency and its harmonics are not locally grouped despite originating from the same sound source. For example, if the fundamental frequency is 100 Hz, then its harmonics are 200 Hz, 300 Hz, etc. The locality bias, again while useful for natural images, may not be a sufficiently good inductive bias for image representations of sound in some embodiments because the frequencies associated with a given sound event are non-locally distributed.

The ViT, through its utilization of a self-attention mechanism, structurally lacks these two inductive biases of translational invariance and locality, which are usually quite useful biases for natural images. However, in some embodiments disclosed herein, it makes good sense to disregard these biases as they do not pertain to image representations of sound. Since the ViT is not structurally constrained to the inductive biases of translational invariance and locality like the CNN, the ViT can explore the parameter space more freely to find a better set of generalizable rules for classifying image representations of sound. Furthermore, the ViT has a global receptive field, and it can therefore more easily model non-locally distributed spectral properties.

Other embodiments disclosed herein are illustratively configured to utilize an involutional neural network (INN) instead of or in addition to a CNN or a ViT.

The convolution operator is a sliding window or kernel that performs local aggregations across neighboring pixels. The convolution operator is spatial agnostic because the kernels sliding across the image share the same weights. The convolution operator is channel specific because each kernel produces one channel in the next layer. A convolutional kernel is of size $K*K*C_{input}$ where K is the dimension size of the kernel and $C_{input}$ is the number of input channels. The INN inverts this paradigm. The INN's kernel shares weights across the channel dimension as opposed to sharing weights across the width and height of the image. Thus the involution kernel is channel agnostic. The size of the involution kernel is $K*K*1$ because the weights are broadcast across the channel dimension. Moreover, the weights of the involution kernel dynamically change as it slides across the image. Kernel weights are computed dynamically using a small neural network conditioned on the given pixel value, giving the weights a positional dependence, in contrast to a convolution kernel that shares weights as it slides across an image. Thus, the involution operator is spatial specific. The involution operator is similar in some respects to a self-attention mechanism in the sense that its weights are also generated dynamically based on location.

Combinations of multiple different types of neural networks, such as CNNs, ViTs and/or INNs, can be used in other embodiments. The term "neural network" as used herein is intended to be broadly construed, so as to encompass these and numerous other machine learning and/or artificial intelligence arrangements.

Referring now to FIG. 13, example biomedical acoustics classifiers are shown that utilize images comprising spectrograms, MTFs and GAFs for pediatric heart sound classification. The figure illustrates three distinct methods implemented in accordance with the techniques disclosed herein, including in part (a) of the figure a benchmark method that generates Mel-spectrogram image representations of pediatric heart sounds and classifies those image representations using a neural network 1300 implementing a ResNet-50 model, which is a 50-layer deep CNN, and two additional methods, denoted Method 1 and Method 2, as shown in respective parts (b) and (c) of the figure. Method 1 utilizes MTF image representations and a neural network 1310 implementing a ViT model, and Method 2 utilizes GAF image representations and the neural network 1310 implementing the ViT model.

Pediatric murmurs are extremely common, yet providers vary widely in their ability to auscultate pediatric heart sounds accurately. Illustrative embodiments herein provide novel deep learning algorithms that can achieve automated multiclass classification of pediatric heart sounds into multiple groups. For example, some of these embodiments classify pediatric heart sounds into three groups: normal heart sounds (no murmur), innocent murmurs, and pathologic murmurs. As will be described in more detail below, some embodiments utilize a ViT model trained on either MTF or GAF image representations of the pediatric heart sound's frequency spectrum.

An estimated 66% of all children, and up to 75% of all newborns will have heart murmurs at some point during their childhood, yet less than 1% of children are born with congenital heart disease every year. Evaluation for a murmur is one of the most common reasons for referral to a pediatric cardiologist. Up to 60% of the murmurs referred will be diagnosed as innocent murmurs. By definition, innocent murmurs are physiologic; the presence of an innocent murmur is not indicative of an underlying structural or physiological abnormality. A significant majority of innocent murmurs will be the Still's murmur, a characteristic low-pitched, musical murmur caused by the resonation of blood in the left ventricular outflow tract. Other common innocent murmurs include pulmonary and systolic flow murmurs, which are caused by normal blood flow through the heart, and venous hums, a distinct sound caused by the flow of blood returning through the veins above the heart. Pathologic murmurs, by contrast, vary widely in their identifying characteristics; they may be systolic or diastolic, harsh or quiet, have a crescendo-decrescendo quality, or be uniform in volume throughout the cardiac cycle.

Auscultation is usually the first step that a clinician will take to evaluate a pediatric heart murmur. Auscultation is a clinical skill that is highly dependent on the user. Auscultation in children is especially challenging, complicated by high heart rates which make it difficult to differentiate between systole and diastole, and by crying and agitation, particularly in infants. Primary care providers (PCPs) and general practitioners, especially less experienced clinicians, often have difficulty distinguishing pediatric heart murmurs reliably and accurately. Multiple studies have shown that primary care providers have lower accuracy and wider variability in diagnosing innocent murmurs compared to pediatric cardiologists. As a result, many PCPs will refer a child with an innocent murmur for evaluation by a pediatric cardiologist, even in the absence of symptoms. While timely diagnosis of a pediatric heart murmur is critical for the early diagnosis of congenital heart disease, prevention of anxiety and resource expenditure associated with unnecessary murmur referrals is also of high concern. Thirty to seventy-five percent of murmur referrals will eventually be diagnosed as innocent. In the United States, this amounts to up to 800,000 children referred to pediatric cardiologists for innocent heart murmurs each year. These referrals pose a significant burden of care, resulting in up to half a billion spent per year on unnecessary imaging.

Illustrative embodiments herein address these and other drawbacks of conventional practice by providing automated multiclass classification of pediatric heart sounds, for example, as normal (no murmur present), innocent murmur present, or pathologic murmur present, although it is to be appreciated that additional or alternative classes can be used. These embodiments implement example preprocessing methods for producing a two-dimensional image representation of sound from a one-dimensional (i.e., univariate) audio signal. An initial step in these example preprocessing methods is to apply a Fourier Transform (FT) to the univariate timeseries signal to obtain the frequency spectrum. The frequency spectrum represents the audio signal in terms of its component frequencies, for example, with amplitude conveyed on the y-axis and frequency conveyed on the x-axis. A two-dimensional image representation is then derived from the audio frequency spectrum via an MTF or a GAF. Illustrative embodiments herein extend the MTF and the GAF to univariate sequence data indexed in the frequency domain for audio classification. The MTF treats univariate sequence data as a first-order Markov chain and depicts the transition probabilities for all pairwise sets of discretized values. The GAF visualizes a Gram matrix derived from polar encoded univariate sequence data. As indicated previously, in some embodiments, a ViT model is utilized for classifying MTF and GAF image representations of the frequency spectrum for pediatric heart sound classification.

As shown in FIG. 13, illustrative embodiments include the benchmark method, Method 1 and Method 2, shown in respective parts (a), (b) and (c) of the figure. The benchmark method processes Mel-spectrogram images using the neural network 1300 implemented in accordance with a ResNet-50 model. Method 1 and Method 2 process respective MTF and GAF image representations using the neural network 1310 implemented in accordance with a ViT model.

The first step of both Method 1 and Method 2 is to apply the Fourier Transform (FT) to the auscultated timeseries data to produce the frequency spectrum. Then, an image representation of the frequency spectrum is generated. In Method 1, the frequency spectrum is quantized and binned into discrete states. Viewing the binned frequency spectrum as a first-order Markov chain, each bin represents a distinct state. The MTF visualizes the Markov transition probability matrix as an image. In Method 2, the frequency spectrum is mapped onto the polar coordinate system. The Gram matrix is calculated from the polar coordinate encoded frequency spectrum and the GAF visualizes the Gram matrix as an image. The image representations are then used to train the ViT model which illustratively comprises a sequence of 10 transformer encoders with multi-headed self-attention, followed by a fully connected layer. The final activation function is illustratively shown as a softmax activation function in the figure, suitable for multiclass classification, but alternative activation functions can be used, such as a sigmoid activation function for binary classification.

Anonymized and privacy-preserving pediatric sound data was collected with parental consent for use in training the neural networks. Auscultated heart sounds were recorded with a 3M Littmann Core digital stethoscope at a sampling rate of 4000 Hz. A label of "normal," "innocent," or "pathologic" was given by board-certified pediatric cardiologists. Sounds labeled as "pathologic" were validated with echocardiography. The collected sounds were supplemented with additional "normal" and "pathologic" sounds from the CirCor DigiScope dataset, a publicly available database of pediatric heart sounds collected in Brazil.

An experimental study was conducted on the illustrative embodiments shown in FIG. 13, utilizing pediatric heart sounds from a total of 138 patients, 65 of which were from the CirCor DigiScope dataset. Each heart sound recording varied between 15 to 60 seconds long, and was split into 5 second clips to maximize the number of samples. The resulting pediatric heart sounds included 402 collected samples, and 340 samples from the CirCor DigiScope dataset, for a total of 742 samples. To prevent data leakage, the training, validation, and testing splits were done on the patient level, meaning samples sourced from the same patient would appear in the same split. The final dataset included 742 pediatric heart sounds in total, including 366 normal heart sounds, 175 innocent murmurs, and 216 pathological murmurs. Innocent murmurs included Still's murmur, flow murmurs, and venous hums. Pathologic murmurs included ventricular septal defect (VSD), mitral regurgitation, mitral stenosis, pulmonary stenosis, pulmonary regurgitation, Tetralogy of Fallot (TOF), aortic stenosis, aortic regurgitation, and subaortic stenosis. Pathologic heart sounds from CirCor DigiScope were diastolic murmurs that were otherwise unspecified.

Three different classification problems were implemented: binary classification of pediatric heart sounds as murmur absent versus murmur present (innocent and pathologic), binary classification of pediatric heart murmurs as innocent versus pathologic given prior information that a murmur is present (i.e., the normal sounds were excluded in this study), and multiclass classification of pediatric heart sound as normal, innocent murmur, and pathologic murmur. For each classification problem, first 20% of the data is randomly held out to serve as an independent test set for final model evaluation. The remaining 80% of data was divided into train and validation sets for five-fold cross-validation.

The one-dimensional audio signal timeseries data was preprocessed into two-dimensional image representations to spatially encode the audio features. As indicated previously, the benchmark method, Method 1 and Method 2 utilized Mel-spectrogram, MTF and GAF image representations, respectively.

As described elsewhere herein, a spectrogram depicts the spectrum of frequencies of a signal as it varies with time. In the present embodiments, the x-axis represents time, the y-axis represents frequency, and amplitude of a particular frequency component at a given point in time is represented by the intensity of color. The spectrograms are generated from the pediatric heart sounds using short-time Fourier transforms as follows. First, the audio signals are windowed using a Hann window of size 512 and a hop length of 256. A 512-point fast Fourier transform is applied to each window to generate a spectrogram. The Mel-scaled, dB-scaled spectrograms are generated by logarithmic rescaling of the amplitude and frequency axis. The amplitude axis is converted to the dB scale. The frequency axis is transformed onto the Mel scale, in the manner described elsewhere herein. The resulting Mel-scaled, dB-scaled spectrograms are resized to be 100×100 (time resolution by frequency resolution) in size using bicubic interpolation. Here, brighter colors correspond to greater intensity or amount of a given frequency component, and darker colors correspond to lower intensity or amount.

The MTF treats one-dimensional sequence data as a first-order Markov chain and depicts the transition probabilities for all pairwise sets of discretized values. For pediatric heart sounds, MTF image representations of the audio signal in the frequency domain are generated. First, the Fourier transform is applied to the pediatric heart sound timeseries data to obtain the frequency spectrum. The frequency spectrum is discretized into Q=10 distinct bins along the different possible values that can be assumed, with the first and last bin corresponding to the highest and lowest possible frequency value ranges, respectively. A quantile binning strategy is used so that each bin contains the same number of points. Viewing the discretized frequency spectrum as a first-order Markov chain, each bin represents a distinct state. A Q×Q Markov transition matrix is computed by quantifying the number of state transitions between all pairwise sets of states, with the diagonal of the Markov transition matrix representing self-transition probabilities. Mathematically, this can be stated as follows. Let $F=\{f_0, f_1, f_2, \ldots f_i \ldots f_N\}$ represent the discretized points over which the frequency spectrum spans N timestamps such that the frequency at time $t_i$ with is given by the value $f_i$. Each value $f_i$ is mapped to a bin or state $q_j$, where $j \in [1, Q]$. The Q×Q Markov transition matrix W is defined as follows:

$$W = \begin{bmatrix} w_{1,1} = P(f_i \in q_1 | f_{i-1} \in q_1) & \cdots & w_{1,Q} = P(f_i \in q_1 | f_{i-1} \in q_Q) \\ w_{2,1} = P(f_i \in q_2 | f_{i-1} \in q_1) & \cdots & w_{2,Q} = P(f_i \in q_2 | f_{i-1} \in q_Q) \\ \vdots & \ddots & \vdots \\ w_{Q,1} = P(f_i \in q_Q | f_{i-1} \in q_1) & \cdots & w_{Q,Q} = P(f_i \in q_Q | f_{i-1} \in q_Q) \end{bmatrix}$$

where $w_{i,j}$ represents the frequency count with which a frequency value in bin $q_j$ is followed by a frequency value in the bin $q_i$. Transition probabilities are derived by normalizing the Markov transition matrix:

$$\sum_{i=1}^{Q} \sum_{j=1}^{Q} w_{i,j} = 1.$$

Finally, the MTF is a visual depiction of the Markov transition probabilities where brighter colors correspond to higher transition probabilities and darker colors correspond to lower transition probabilities. The resulting MTF images are resized to be 100×100 using bicubic interpolation.

The GAF visualizes a quasi-Gram matrix derived from one-dimensional sequence data. For the pediatric heart sounds, GAF image representations of the audio signal in the frequency domain are generated. A Gram matrix is a matrix of all possible pairwise sets of inner products. The term "quasi-Gram matrix" is used here because the resulting matrix that is visualized is a version of the Gram matrix that uses a modified definition of the inner product as explained below. First, the Fourier transform is applied to the pediatric heart sound timeseries data to obtain the frequency spectrum. The Gram matrix calculates inner products of vectors in a 2D space; therefore, the frequency spectrum is first mapped onto the polar coordinate system. Again, let $F=\{f_0, f_1, f_2, \ldots f_i \ldots f_N\}$ represent the discretized points over which the frequency spectrum spans N timestamps such that the frequency at time $t_i$ with is given by the value $f_i$. The frequency spectrum is mapped onto polar coordinate system as follows:

$$\begin{cases} \theta_i = \cos^{-1}(f_i) \\ r = \dfrac{t_i}{N}, \ i \in N \end{cases}$$

Now in 2D space, the Gram matrix can be derived. One of the limitations of the inner product in 2D polar space is that the norm of each vector is adjusted for the frequency dependency, meaning the inner product will be biased towards the higher frequency component. To address this issue, one can use either a trigonometric sum or difference between each vector pair. In this study, the final matrix that is derived uses the trigonometric difference of two vector pairs: $\sin(\theta_i - \theta_j)$ where $i, j \in N$ (hence the term "quasi-Gram matrix"). The N×N quasi-Gram matrix G is defined by:

$$G = \begin{bmatrix} <f_1, f_1> & \cdots & <f_1, f_N> \\ <f_2, f_1> & \cdots & <f_1, f_1> \\ \vdots & \ddots & \vdots \\ <f_n, f_1> & \cdots & <f_n, f_n> \end{bmatrix}$$

where the inner product <u, v> is redefined to be <u, v>= $\sqrt{1-u^2}\cdot v-u\cdot\sqrt{1-v^2}$. Finally, the GAF visualizes this quasi-Gram matrix with brighter colors corresponding to larger inner products and darker colors corresponding to smaller inner products. The resulting GAF images are resized to be 100×100 using bicubic interpolation. All image representations in the present embodiments (spectrograms, MTF and GAF) are normalized prior to input into the model into the range [−1, 1].

FIG. 14 shows example image representations comprising spectrograms, MTFs and GAFs for each of a plurality of different types of pediatric heart sounds. More particularly, this figure shows the Mel-spectrogram (left), MTF (middle), and GAF (right) image representations for (a) normal pediatric heart sound, (b) Still's murmur (innocent), (c) mitral regurgitation (pathologic), and (d) pulmonary stenosis and regurgitation due to Tetralogy of Fallot (pathologic). Other image representations can be generated in a similar manner for other types of pediatric heart sounds, including, for example, innocent murmurs such as venous hum and pulmonary flow murmur, and pathologic murmurs such as ventricular septal defect, mitral stenosis, mitral valve prolapse, aortic stenosis, sub-aortic stenosis, aortic regurgitation in hypoplastic left heart syndrome, pulmonary stenosis, and pulmonary stenosis with pulmonary regurgitation.

The example ResNet-50 model utilized in the benchmark method illustratively comprises five blocks, with each block comprising a convolutional layer, a batch normalization layer, a ReLU activation layer, a max pooling layer, and residual or skip connections that allow activations from earlier layers to be propagated down to deeper layers. The final output from the last layer is reshaped into a flattened feature vector using global max pooling, which is fed into a fully connected layer for classification. In the case of binary classification, the final fully connected layer comprises a single node with a sigmoid activation function. In the case of multiclass classification, the fully connected layer comprises three nodes with softmax activation function. The model is trained using an adaptive moment estimation (Adam) optimizer at a learning rate of $1\times10^3$ over the binary cross-entropy loss function in the case of binary classification and over the categorical cross-entropy loss function in the case of multiclass classification.

In the example ViT model utilized in Method 1 and Method 2, the input image is first tokenized into 10 by 10 patches. The patches are flattened and linearly projected (e.g., multiplied by a learnable weight matrix) into a feature vector. A positional encoding is added to each linear projected patch, where the positional encoding is a learnable embedding. The linearly projected patches with their corresponding positional encodings are fed into a sequence of 10 transformer encoder layers. Each transformer encoder layer comprises two subcomponents. The first subcomponent comprises a layer normalization followed by the multi-headed self-attention layers. For the ViT model in the present embodiments, six attention heads are used. The second subcomponent of each transformer encoder comprises another layer normalization followed by a 2-layer fully connected network using a ReLU activation function. Skip or residual connections are used to propagate feature vector representations between each subcomponent of each transformer encoder layer. The final output from the last transformer encoder layer is reshaped into a flattened feature vector, which is then fed into a fully connected layer for classification. In the case of binary classification, the final fully connected layer comprises a single node with sigmoid activation function. In the case of multiclass classification, the fully connected layer comprises three nodes with softmax activation function. The model is trained using Adam optimizer at a learning rate of $1\times10^{-3}$ over the binary cross-entropy loss function in the case of binary classification and over the categorical cross-entropy loss function in the case of multiclass classification.

Five-fold cross-validation receiver operating characteristic (ROC) curves were generated for binary classification of pediatric heart sounds as murmur absent versus murmur present, which includes both innocent and pathologic murmurs, for the ResNet-50 and the ViT models trained on the Mel-spectrogram, MTF, and GAF image representations, respectively, with the murmur present class being treated as the positive class.

Table 2 below summarizes the ROC AUC ("AuROC") values of the ROC curves for each of the models and image representations, for the binary classification of pediatric heart sounds as murmur absent versus murmur present.

TABLE 2

| Preprocessing | Model | |
| --- | --- | --- |
| | ResNet-50 CNN AuROC | ViT AuROC |
| Mel-spectrogram | 0.90 ± 0.04 | 0.92 ± 0.04 |
| Markov transition field | 0.74 ± 0.19 | 0.93 ± 0.01 |
| Gramian angular matrix | 0.86 ± 0.04 | 0.93 ± 0.03 |

Five-fold cross-validation ROC curves were also generated for binary classification of pediatric heart murmurs as innocent versus pathologic, given prior information that a murmur is indeed present (i.e., normal heart sounds have been excluded) for the ResNet-50 and the ViT models trained on the Mel-spectrogram, MTF, and GAF image representations, respectively, with the pathologic murmur class being treated as the positive class.

Table 3 below summarizes the AuROC values of the ROC curves for each of the models and image representations, for the binary classification of pediatric heart murmurs as innocent versus pathologic, given prior information that a murmur is indeed present.

TABLE 3

| Preprocessing | Model | |
| --- | --- | --- |
| | ResNet-50 CNN AuROC | ViT AuROC |
| Mel-spectrogram | 0.66 ± 0.15 | 0.71 ± 0.12 |
| Markov transition field | 0.54 ± 0.11 | 0.72 ± 0.03 |
| Gramian angular matrix | 0.65 ± 0.14 | 0.75 ± 0.08 |

Five-fold cross-validation extended one-versus-rest ROC curves were generated for multiclass classification of pediatric heart sounds as either normal (i.e., murmur absent), innocent murmur, or pathologic murmur, for the ResNet-50 and the ViT models trained on the Mel-spectrogram, MTF, and GAF image representations, respectively.

Table 4 below summarizes the AuROC values of the ROC curves for each of the models and image representations, for the multiclass classification of pediatric heart sounds as either normal, innocent or pathologic.

TABLE 4

| Model | Preprocessing | Normal AuROC | Innocent AuROC | Pathologic AuROC |
|---|---|---|---|---|
| ResNet-50 | Mel-Spectrogram | 0.92 ± 0.04 | 0.89 ± 0.04 | 0.75 ± 0.16 |
| | Markov Transition Field | 0.64 ± 0.24 | 0.69 ± 0.15 | 0.61 ± 0.13 |
| | Gramian Angular Field | 0.80 ± 0.09 | 0.75 ± 0.09 | 0.56 ± 0.18 |
| ViT | Mel-Spectrogram | 0.91 ± 0.06 | 0.84 ± 0.07 | 0.81 ± 0.13 |
| | Markov Transition Field | 0.92 ± 0.02 | 0.88 ± 0.02 | 0.82 ± 0.03 |
| | Gramian Angular Field | 0.94 ± 0.02 | 0.92 ± 0.01 | 0.88 ± 0.04 |

Finally, the best performing model based on the above-described cross-validated ROC curves, which in these embodiments was the ViT trained on GAF image representations, was independently tested for each of the three example classification problems. Confusion matrices were generated for each of normal versus murmur present, innocent versus pathologic murmur and multiclass classification of normal, innocent or pathologic. The threshold that corresponds to the largest geometric mean of sensitivity and specificity based on the averaged ROC curve from five-fold cross validation was selected as the final threshold value. Sensitivity and specificity values for the multiclass classification are computed by collapsing the 3×3 confusion matrix into a 2×2 matrix of pathologic versus innocent and no murmur.

Table 5 below shows the summary performance metrics for the ViT trained on GAF image representations.

TABLE 5

| Summary Performance Metrics | | | |
|---|---|---|---|
| | Sensitivity | Specificity | F1 Score |
| Murmur Present* vs. No Murmur | 0.883 | 0.823 | 0.855 |
| Pathologic* vs. Innocent Murmur | 0.818 | 0.884 | 0.720 |
| Pathologic* vs. Benign Heart Sound | 0.814 | 0.862 | 0.878 |

These summary performance metrics include sensitivity, specificity, and F1 score for each classification problem. The * marks in the table denote the positive class for the corresponding classification problem.

These results indicate that, in the corresponding illustrative embodiments, the MTF and GAF image representations either perform comparably or outperform the spectrogram image representation when used to train the ViT model. The spectrogram representation, which illustratively depicts frequency on the y-axis as it varies with time on the x-axis, inherently has a time-frequency resolution tradeoff. Higher frequency resolution results in less time resolution and vice versa. In contrast, the MTF and GAF image representation are generated from the audio signal in the frequency domain. Thus, the MTF and GAF image representation offer full frequency resolution at the expense of zero-time resolution. For the case of pediatric heart sound classification, this is beneficial: the frequency content is what strictly determines which class a heart sound belongs to (normal versus innocent murmur versus pathologic murmur), rather than when certain frequencies occur.

For cases such as deriving semantic information from speech, the order of the frequency components absolutely matters. For heart sound classification, however, temporal information is not important in determining the class to which the heart sound belongs, given the rhythmic nature of heart sounds, which has repeating frequency components (i.e., S1 and S2). Thus, the spectrogram representation has a lot of redundancy as a result of preserving temporal information due to the cyclic nature of heart sounds. The vast majority of pediatric heart sounds, regardless of class, will have an S1 and S2 component, which is not useful for differentiating between these heart sounds. In the spectrogram representation, repeating S1 and S2 frequency components visually occupies multiple regions of the image representation. Due to natural variances such as recording start times and variations in heart rate, the regions occupied by S1 and S2 frequency components are different from sample to sample, which likely hinders the performance of the computer vision models. The MTF and GAF give full frequency resolution with no temporal information. Higher frequency resolution in and of itself likely improves model performance. Additionally, the S1 and S2 frequency components will more consistently occupy similar regions in the image representation; thus, the computer vision model will have an easier time learning to ignore certain regions while focusing on other regions of higher importance (i.e., the ones that provide discriminatory information).

These results indicate that, in the corresponding illustrative embodiments, the GAF is a better image representation than the MTF for pediatric heart sound classification. This can be attributed at least in part to the fact that generating the MTF is a subjective process while generating the GAF is a bijective process. In other words, multiple different sounds can result in the same MTF image, but a GAF image representation will correspond to one and only one sound. The larger inverse image space of MTF likely hinders its performance to some extent relative to GAF in the corresponding embodiments.

Also, the results indicate that the ViT consistently outperforms the ResNet-50 across all three image representations. The convolution operator utilized in a CNN such as ResNet-50 aggregates information via spatial sliding windows or kernels which use the same learned weights as it slides across an image. This architecture structurally introduces two important inductive biases inherent to CNN: translational invariance and locality. Pooling layers, used in conjunction with convolutional layers in the CNN model in some embodiments, help the model achieve translational invariance. Translational invariance means that an object can be detected irrespective of its location in the image. The locality bias is the notion that closely spaced pixels are more correlated than pixels that are far away.

As described previously, since the ViT is not structurally constrained to the inductive biases of translational invariance and locality like the CNN, the former model can explore the parameter space more freely to find a better set of generalizable rules for classifying image representations of sound. Furthermore, the ViT has a global receptive field, so that it can more easily model non-locally distributed spectral properties. This helps to explain the superior performance of the ViT over the convolution-based ResNet-50 in classifying image representations of pediatric heart sounds in the corresponding embodiments.

The illustrative embodiments described in conjunction with FIGS. 13 and 14 advantageously provide multiclass classification of pediatric murmurs using deep learning, and can distinguish between normal heart sounds, innocent murmurs, and pathologic murmurs with high sensitivity and specificity. When auscultating a child, the two main questions to a provider are 1) whether there is a murmur and 2)

whether any existing murmur is innocent or pathological. The disclosed classification arrangements are able to answer both of these questions with high sensitivity and specificity.

The multiclass classification allows for versatility in how clinicians may utilize it as decision support. The ViT model trained using GAF image representations has high specificity in differentiating between pathologic and innocent murmurs, and high specificity in differentiating between pathologic heart sounds and overall benign heart sounds (normal and innocent murmurs), 0.88 and 0.86 respectively. While this example model exhibits a slightly lower AuROC for pathologic murmurs compared to normal heart sounds and innocent murmurs (0.88 versus 0.94 and 0.92 respectively), its overall accuracy remains high, with both sensitivity and specificity for detecting pathological murmurs versus benign heart sounds exceeding 0.80. This is particularly noteworthy considering the broad range of pathological murmurs that the example model was trained on.

A model configured for multiclass classification in the manner disclosed herein therefore both help reduce unnecessary referrals of innocent murmurs, as well as facilitate detection of pathological murmurs. This is especially important when considering differences in practice geography and availability of healthcare resources. For example, resource-rich areas may benefit more from preventing over-referrals of innocent murmurs and over-utilization of echocardiography for common benign murmurs. Resource-limited areas that may lack easy access to subspecialists or to echocardiography may benefit more from the use of this model to detect pathological murmurs.

It should be noted that the above-described study was limited in terms of volume of data collected. Outside of the CirCor DigiScope database, existing publicly available heart sound databases have an adult focus. Adult heart sounds are generally not applicable for pediatric heart sound classification. Children have much higher heart rates, and therefore shorter diastole relative to adult heart sounds, which impacts the timing and quality of murmurs. Furthermore, the physiology underlying murmurs in children differs greatly from that in adults. The study utilized a comprehensive dataset that reflects the range of innocent and pathological pediatric murmurs potentially encountered in clinical practice.

While the example dataset used in the study captures the vast majority of commonly seen innocent and pathologic pediatric murmurs, it is most notably missing atrial septal defects and peripheral pulmonic stenosis, and alternative datasets including such sounds could be used for further training. Atrial septal defects are the second most common congenital heart defect in children; they frequently go undiagnosed until adulthood, as they are often asymptomatic. The characteristic murmur is a soft systolic murmur, similar to common innocent murmurs, albeit with a distinct splitting of the second heart sound. While small defects may spontaneously resolve, large ones can cause complications such as dysrhythmias, pulmonary hypertension, or in severe cases right-sided heart failure. Therefore, illustrative embodiments disclosed herein, through appropriate training of a deep learning algorithm, can be configured to distinguish between this common defect versus innocent murmurs. Peripheral pulmonic stenosis is a subtype of pulmonary stenosis, the fifth most common congenital heart defect. Peripheral pulmonic stenosis is a common murmur in infants and is caused by a narrowing in a distal branch of the pulmonic artery. While other types of pulmonary stenosis (i.e., valvular and sub-valvular pulmonary stenosis) are pathologic and often require intervention, peripheral pulmonic stenosis is considered an innocent murmur with a benign clinical course. It is also important to note that the example dataset is intended to reflect what can be encountered in the general pediatric office, so murmurs that would be encountered in the perinatal period or in the neonatal intensive care unit (i.e., patent ductus arteriosus, coarctation of the aorta) are not included. The example dataset is also missing certain types of critical congenital heart defects, such as truncus arteriosus, transposition of the great arteries, total anomalous pulmonary vein return, and Ebstein's anomaly, but each of these pathologies make up 1 to 3% of congenital heart disease with incidences as low as <1 in 100,000. Again, a larger, more comprehensive dataset can be used and will likely result in better and more generalizable models.

As described above in conjunction with FIGS. 13 and 14, these embodiments include creating either an MTF or GAF image representation of the heart sound's frequency spectrum and using the image-based representation of sound to train a ViT. It was found in above-described study that this methodology outperforms a CNN trained on spectrogram images as well as a ViT trained on spectrogram images. The study also demonstrates the potential of deep learning to provide clinically relevant decision support to clinicians to classify heart sounds in children. The ability of these embodiments to achieve multiclass classification allows for versatility in how it may be used as clinical decision support as well as applicability across different types of practice environments.

Again, other embodiments can be configured to train neural network models using expanded datasets that include additional examples of innocent and pathologic pediatric heart sounds. Such expanded datasets can be used in illustrative embodiments to achieve more granular multiclass classification of pediatric heart sounds (i.e., distinguishing aortic stenosis from mitral regurgitation).

Additional details relating to illustrative embodiments in another use case will now be described with reference to FIGS. 15 through 17.

FIG. 15 illustrates the operation of example biomedical acoustics classifiers utilizing image representations comprising spectrograms and recurrence plots for blood flow sound classification in illustrative embodiments.

As indicated previously herein, for hemodialysis patients, arteriovenous fistula (AVF) patency determines whether adequate hemofiltration can be achieved, and directly influences clinical outcomes. Illustrative embodiments herein provide deep learning models for automated AVF stenosis screening based on the sound of AVF blood flow using supervised learning with data validated by ultrasound. Such embodiments demonstrate the importance of contextualizing the sound with location metadata as the characteristics of the blood flow sound varies significantly along the AVF. In some embodiments, a model using a ViT trained on spectrogram images provided excellent performance. This model can screen for stenosis at a performance level comparable to that of a nephrologist performing a physical exam, but with the advantage of being automated and scalable. In a high-volume, resource-limited clinical setting, automated AVF stenosis screening can help ensure patient safety via early detection of at-risk vascular access, streamline the dialysis workflow, and serve as a patient-facing tool to allow for at-home, self-screening.

Auscultation (i.e., listening for internal body sounds) is a noninvasive method, compared to digital subtraction angiography or venous cannulation, and more convenient compared to ultrasound for detecting abnormal blood flow. Additionally, a change in access bruit or thrill may be one of the earliest clinical indicators that a stenosis is developing and can be measured using a low-cost and widely available digital stethoscope. However, the reality is that auscultation is a highly subjective physical exam technique and largely depends on the skill of the listener. Since the timely diagnosis of stenosis is crucial for maintaining dialysis access, applying deep learning to AVF blood flow sounds can enhance the ability of healthcare providers to screen for AVF stenosis both reliably and efficiently.

In some embodiments, blood flow sounds are recorded using a digital stethoscope at multiple distinct locations (e.g., six locations) along each patient's AVF. The recorded one-dimensional blood flow audio signals are preprocessed into two-dimensional image representations to leverage computer vision models. The disclosed models are trained using supervised learning with labels validated from concurrent duplex ultrasound. It was found that these models could better predict patients with a stenosis compared to non-machine learning analyses of the same sound files. A deep learning model trained on normal and abnormal blood flow sounds that can identify AVF stenosis could establish a level of objectivity to the subjective interpretation of auscultated sounds via the extraction and quantification of relevant features from the blood flow audio signals. The disclosed biometric classification arrangements can serve, for example, as a patient-facing tool to allow for at-home, self-screening of AVF stenosis. This ability could be especially helpful in under-resourced areas where patients may not be receiving routine screening. The timely and accurate detection of AVF stenosis using deep learning analysis of AVF blood flow sounds can reduce downstream healthcare costs, and more importantly, improve the quality of life of patients.

Part (a) of FIG. 15 illustrates that the sound of blood flow is captured by a digital stethoscope 1501. The one-dimensional blow flow audio signal is preprocessed into two-dimensional image representations, which were used to train the deep learning models, each corresponding to a different instance of deep learning model 1502 in the figure. Ultrasound imaging and blood flow velocities measured by concurrent duplex ultrasound 1503 were used to inform the binary ground truth label of either "patent" or "stenotic." The deep learning models are trained following the supervised learning paradigm.

As shown in part (b) of FIG. 15, the six locations along the arteriovenous fistula from where blood flow sounds are collected numbered in increasing order from most distal to most proximal based on the anatomic definitions of the arm: artery, anastomosis (where the artery joins the vein), the distal vein, the middle vein, the proximal vein, and the arch of the vein. Although the figure shows the brachiocephalic fistula, the techniques are similarly applicable to the brachiobasilic, radiocephalic, and radiobasilic fistula.

Part (c) of FIG. 15 illustrates that laminar flow through a patent AVF generates a quiet "whooshing" sound. As an AVF develops stenosis, laminar flow will transition to turbulent flow, as shown in part (d) of FIG. 15. Increasing turbulent flow will result in an increased amount of higher frequency components in the generated sound. Clinically, the sound heard when auscultating a stenosed AVF is often described as a "high-pitched systolic bruit or thrill." The two image representations of sound utilized in these embodiments are the Mel-spectrogram and the recurrence plot. The Mel-spectrogram is generated from applying the short-time Fourier Transform (STFT) to the waveform. The recurrence plot is generated from a recurrence quantification analysis (RQA) of the frequency spectrum, which is obtained from applying the Fourier Transform (FT) on the waveform. The illustrative example patent and stenotic waveforms, frequency spectra, Mel-spectrograms, and recurrence plots seen here are taken from a patent and stenotic "proximal" vein, respectively.

The sound produced by blood flowing through an AVF can be an important indicator of the AVF's patency status. As noted above, blood flow through a patent AVF is laminar and will create a quiet "whooshing" sound. A stenosed AVF can be conceptualized as a converging-diverging nozzle. Flow through a converging-diverging nozzle is characterized by the jet Reynolds number, in accordance with the following equation:

$$Re = \frac{uD}{v}$$

where u is the velocity, D is the jet diameter, and v is the kinematic viscosity of the fluid. Experiments have shown that if Re exceeds about 2000, the jet flow will be turbulent. A stenosed AVF will have a reduced lumen diameter relative to a patent AVF. By conservation of mass and momentum, as the lumen diameter decreases, fluid velocity will increase. From the jet Reynolds equation above, it can be seen that this inherent inverse relationship between velocity and diameter means that velocity and diameter have opposing effects in determining the overall Reynolds number. However, as an AVF develops stenosis, the velocity of blood flow will increase by a larger factor relative to how much the diameter will decrease. This can be understood from a simplified volumetric flow rate equation $$Q = u_1 (\pi r_1^2) = u_2 (\pi r_2^2),$$

where Q is the constant volumetric flow rate, $u_1$ is the fluid velocity at radius $r_1$ and $u_2$ is the fluid velocity at radius $r_2$, assuming an incompressible, Newtonian fluid, which is an acceptable assumption for blood.

In this simplified model, a reduction in the lumen radius by a factor of two will result in an increase in velocity by a factor of four. In other words, as an AVF develops stenosis, the increased fluid velocity u caused by the reduced diameter D will overall result in a net increase of the jet Reynolds number. Once the jet Reynolds number crosses a certain threshold (e.g., 2000), the flow regime will transition from laminar to turbulent. Turbulent flow produces a different sound compared to laminar flow. This concept of turbulent fluid induced noise is characterized by Lighthill's wave equation. Turbulent fluid flow collaterally generates pressure and density variations in the fluid, which in turn generates the pressure and density variations that are illustratively perceived as noise in some embodiments herein. Increasing turbulence will result in an increased amount of higher frequency components in the generated sound. Clinically, the sound heard when auscultating a stenosed AVF is often described as a "high-pitched systolic bruit or thrill."

The frequency spectra at each location indicate that a stenosis is characterized by a "double-peak." The left (lower frequency peak) corresponds to diastole (when the heart's ventricles relax) and the right (higher frequency peak) corresponds to systole (when the heart's ventricles are contracting). During systole, there is a momentary increase in the velocity of blood flow all throughout the vasculature, including the AVF. According to the jet Reynolds equation above, the increased velocity through a stenosed AVF directly contributes to increasing the jet Reynolds number. The flow regime is more likely to transition to turbulent flow at the site of the stenotic lesion during systole because at baseline (during diastole) the stenotic lesions is already characterized by higher Reynolds number by virtue of the diminished lumen diameter and its direct effect on increasing velocity. This increased propensity to develop turbulent flow during systole at the stenotic site is responsible for the second higher frequency peak seen in the frequency spectra and clinically corresponds to the "high pitched systolic bruit of thrill" heard during auscultation. A patent AVF is better able to accommodate the increased throughput of blood during systole, and the second higher frequency peak is not as prominent or entirely absent.

To gain a better understanding of the data and to see how well these individual observations generalize, the average frequency spectrum was computed across all patients in a study of corresponding illustrative embodiments, stratified by location and patency status. More particularly, the averaged frequency spectrum of blood flow sounds for patent and stenotic fistulas was computed across all patients in the training and validation sets (311 patients total) at five sites, namely, the anastomosis site, the distal vein site, the middle vein site, the proximal vein site and the venous arch site.

Table 6 below shows the numerical summary of the averaged frequency spectra including the area under the curve (AUC), peak frequency, maximum frequency, and full width at half max (FWHM).

TABLE 6

| Averaged Frequency Spectrums | | AUC Mean ± SD | Peak Frequency Mean ± SD (Hz) | Maximum Frequency Mean ± SD (Hz) | Full Width at Half Max Mean ± SD (Hz) |
|---|---|---|---|---|---|
| Anastomosis | Patent | 2773 ± 1946 | 164 ± 95 | 1318 ± 177 | 414 ± 19 |
| | Stenotic | 4143 ± 2960 | 195 ± 132 | 1426 ± 147 | 401 ± 45 |
| Distal | Patent | 1779 ± 1418 | 124 ± 53 | 1190 ± 178 | 208 ± 14 |
| | Stenotic | 4032 ± 3189 | 184 ± 112 | 1392 ± 139 | 423 ± 16 |
| Middle | Patent | 1170 ± 940 | 115 ± 51 | 989 ± 216 | 158 ± 9 |
| | Stenotic | 2387 ± 1250 | 206 ± 131 | 1304 ± 142 | 400 ± 22 |
| Proximal | Patent | 844 ± 649 | 104 ± 43 | 942 ± 232 | 150 ± 15 |
| | Stenotic | 1551 ± 1015 | 166 ± 118 | 1153 ± 238 | 396 ± 97 |
| Arch | Patent | 616 ± 459 | 88 ± 31 | 861 ± 172 | 140 ± 13 |
| | Stenotic | 762 ± 410 | 100 ± 39 | 950 ± 166 | 126 ± 15 |

The "double-peaking" is not as distinct compared to the individual examples likely because the higher frequency peaks blend together when averaged. However, the distributions do appear to be bimodal, correlating with systole and diastole of the heart cycle. On average, the stenotic frequency spectra have higher AUC values compared to their location-controlled counterparts, at all five studied locations. The AUC for the frequency spectrum corresponds to energy, which is analogous to loudness. Additionally, on average, the stenotic frequency spectra reach higher maximum frequencies compared to the location-controlled counterparts, at all five studied locations. This is consistent with higher degrees of turbulent flow (caused by the stenosis) resulting in higher frequency components in the generated sound. Finally, on average, the stenotic frequency spectra all have peak frequencies that are right shifted compared to the patent frequency spectra, at all five studied locations, which correlate with the fact that even during diastole, blood is flowing faster at the stenotic site due to the reduced lumen size. In short, from the above data it is observed that, on average, blood flow through a stenotic lesion is louder and has higher pitch, which is consistent with the clinical physical exam.

Illustrative embodiments disclosed herein are configured to train a deep learning model to learn differences in blood flow sound between a patent AVF and a stenotic AVF. Experiments performed on these embodiments as described below also help assess how important is it to contextualize the sound with information about the location along the AVF from which the sound was sourced, and how important it is to contextualize the sound with information regarding the anatomical original of the artery and vein used to construct the AVF.

A first experiment, denoted Experiment 1, allows a direct comparison of the three different models architectures and two different preprocessing methods explored. In this experiment, independent classifiers are trained on patent and stenotic sounds at each location, testing every combination of the three model architectures with the two preprocessing methods. The three model architectures in these embodiments illustratively include a CNN model, a ResNet-50 model pretrained on ImageNet weights, and a ViT. The two preprocessing methods are spectrogram image generation and recurrence plot image generation.

FIG. 16 shows more detailed view of the example neural networks utilized in these illustrative embodiments. More particularly, these models include a CNN, a ResNet-50 CNN, and a ViT, denoted as Model 1, Model 2 and Model 3, respectively, each configured as shown in the figure. The ResNet-50 model of FIG. 16 is the same model utilized in the benchmark method of FIG. 13. The ViT model of FIG. 16 is similar to the ViT model utilized in Method 1 and Method 2 of FIG. 13.

FIG. 17 shows another example of a neural network comprising a modified ViT 1700 in an illustrative embodiment. In this embodiment, the modified ViT 1700 takes an encoded categorical input 1702 via concatenation to a flattened feature vector 1704 coming out of a last transformer encoder layer. The encoded categorical input 1702 in this embodiment illustratively comprises metadata (e.g., location metadata).

From Experiment 1, it is observed that spectrogram images outperform the recurrence plot image, achieving higher AuROC and AuPRC values for each model architecture, where AuPRC denotes Area under Precision-Recall Curve. It should be noted that AuPRC values are interpreted in the context of the true positive rate for each location as precision and recall do not consider the true negative rate. The spectrogram images represent frequency as it varies with time, and so the spectrograms contain information from both the time and frequency domain. The recurrence plots are constructed from the frequency spectrum, and so the recurrence plots contain information only from the frequency domain. At first thought, it may be intuitive to believe that the differences between patent and stenotic sounds are only encoded in the frequency domain, as suggested by the above analysis on the frequency spectra of the sounds. However, the spectrograms outperforming the recurrence plots means there is also useful information encoded in the time domain that is helping the model learn the difference between patent and stenotic sounds. For the spectrogram images, three different time resolutions were tested at a constant frequency resolution (374×128, 128× 128, 32×128), and the best performing spectrogram resolution for these embodiments was the largest (374×128). Note that for the ViT, the time resolution of 374 to 368 was resized to be compatible with the 16×16 patch tokenization step. This further supports the position that there are distinguishing features in the time domain and is consistent with the general idea that the model performs better when given more information to learn from.

It is also observed from Experiment 1 that the ViT outperforms both convolutional neural network architectures on the spectrogram images. The convolution operator aggregates information via spatial sliding windows or kernels which use the same learned weights as it slides across an image. As indicated elsewhere herein, this architecture structurally introduces two important inductive biases inherent to CNN: translational invariance and locality. Pooling layers, used in conjunction with convolutional layers in the models in illustrative embodiments, helps the model achieve translational invariance. Translational invariance means that an object can be detected irrespective of its location in the image. The locality bias is the notion that closely space pixels are more correlated than pixels that are far away. The ViTs, by using the self-attention mechanism, structurally lack these two inductive biases of translational invariance and locality. Accordingly, the ViT can explore the parameter space more freely to find a better set of generalizable rules for classifying spectrograms. This helps to explain the superior performance of the ViT over the convolution-based neural networks in classifying the spectrogram images of blood flow sound. Moreover, the convolution operator is a local operator, meaning only information that falls within the predefined window size can be aggregated. The ViT maintains a global receptive field at every layer. Thus, the ViT can learn long range dependencies and aggregate global information in early layers, resulting in improved performance.

After establishing that the ViT trained with 368×128 spectrogram images performs the best among these illustrative embodiments in the example blood flow classification study, this combination is further tested to characterize the importance of the location metadata. From qualitative inspection of the averaged frequency spectra, each location's averaged frequency spectrum has a distinctive global shape, which suggests that the blood flow sounds differ from each other depending on the location. From Table 6, it can be seen that at the anastomosis site, the sounds have the largest average AUC value. The sounds have the smallest average AUC value at the venous arch location. In other words, the blood flow sound is loudest at the anastomosis and softest at the venous arch, again highlighting how the characteristics of blood flow sounds changes as a function of location. Thus, it appears to be important to contextualize the blood flow sounds with location metadata.

Tables 7-1, 7-2 and 7-3 below show a summary of results for Experiment 1, which as previously described uses independent binary classifiers based on the neural network models of FIG. 16 to distinguish patent versus stenotic at each location. The results for Model 1, Model 2 and Model 3 are shown in Tables 7-1, 7-2 and 7-3, respectively.

TABLE 7-1

| Location | Pre-Processing | Size | Model 1: CNN | |
| | | | AuROC | AuPRC |
| --- | --- | --- | --- | --- |
| Anas-tomosis | Spectrogram | 374* × 128 | 0.64 ± 0.18 | 0.13 ± 0.19 |
| | | 128 × 128 | 0.56 ± 0.19 | 0.13 ± 0.19 |
| | | 32 × 128 | 0.53 ± 0.13 | 0.12 ± 0.05 |
| | Recurrence Plot | 128 × 128 | 0.50 ± 0.15 | 0.10 ± 0.12 |
| Distal | Spectrogram | 374* × 128 | 0.66 ± 0.13 | 0.56 ± 0.16 |
| | | 128 × 128 | 0.66 ± 0.12 | 0.60 ± 0.10 |
| | | 32 × 128 | 0.61 ± 0.10 | 0.53 ± 0.09 |
| | Recurrence Plot | 128 × 128 | 0.66 ± 0.08 | 0.63 ± 0.11 |
| Middle | Spectrogram | 374* × 128 | 0.74 ± 0.14 | 0.35 ± 0.17 |
| | | 128 × 128 | 0.79 ± 0.17 | 0.36 ± 0.31 |
| | | 32 × 128 | 0.76 ± 0.10 | 0.33 ± 0.19 |
| | Recurrence Plot | 128 × 128 | 0.70 ± 0.16 | 0.31 ± 0.16 |
| Proximal | Spectrogram | 374* × 128 | 0.74 ± 0.13 | 0.34 ± 0.18 |
| | | 128 × 128 | 0.70 ± 0.11 | 0.30 ± 0.15 |
| | | 32 × 128 | 0.74 ± 0.10 | 0.32 ± 0.15 |
| | Recurrence Plot | 128 × 128 | 0.65 ± 0.09 | 0.27 ± 0.13 |
| Arch | Spectrogram | 374* × 128 | 0.68 ± 0.18 | 0.26 ± 0.20 |
| | | 128 × 128 | 0.61 ± 0.17 | 0.24 ± 0.19 |
| | | 32 × 128 | 0.48 ± 0.13 | 0.18 ± 0.15 |
| | Recurrence Plot | 128 × 128 | 0.61 ± 0.16 | 0.26 ± 0.17 |

TABLE 7-2

| Location | Pre-Processing | Size | Model 2: ResNet-50 | |
| | | | AuROC | AuPRC |
| --- | --- | --- | --- | --- |
| Anas-tomosis | Spectrogram | 374* × 128 | 0.61 ± 0.21 | 0.16 ± 0.26 |
| | | 128 × 128 | 0.53 ± 0.14 | 0.13 ± 0.09 |
| | | 32 × 128 | 0.57 ± 0.16 | 0.12 ± 0.04 |
| | Recurrence Plot | 128 × 128 | 0.51 ± 0.23 | 0.17 ± 0.23 |
| Distal | Spectrogram | 374* × 128 | 0.70 ± 0.13 | 0.65 ± 0.12 |
| | | 128 × 128 | 0.73 ± 0.13 | 0.68 ± 0.14 |
| | | 32 × 128 | 0.68 ± 0.11 | 0.67 ± 0.10 |
| | Recurrence Plot | 128 × 128 | 0.67 ± 0.10 | 0.64 ± 0.11 |
| Middle | Spectrogram | 374* × 128 | 0.73 ± 0.17 | 0.27 ± 0.23 |
| | | 128 × 128 | 0.80 ± 0.14 | 0.40 ± 0.28 |
| | | 32 × 128 | 0.80 ± 0.10 | 0.38 ± 0.22 |
| | Recurrence Plot | 128 × 128 | 0.78 ± 0.14 | 0.39 ± 0.26 |
| Proximal | Spectrogram | 374* × 128 | 0.77 ± 0.10 | 0.41 ± 0.17 |
| | | 128 × 128 | 0.77 ± 0.07 | 0.34 ± 0.14 |
| | | 32 × 128 | 0.78 ± 0.14 | 0.41 ± 0.22 |
| | Recurrence Plot | 128 × 128 | 0.68 ± 0.17 | 0.30 ± 0.20 |
| Arch | Spectrogram | 374* × 128 | 0.71 ± 0.11 | 0.30 ± 0.17 |
| | | 128 × 128 | 0.76 ± 0.16 | 0.47 ± 0.28 |
| | | 32 × 128 | 0.62 ± 0.18 | 0.27 ± 0.22 |
| | Recurrence Plot | 128 × 128 | 0.67 ± 0.12 | 0.28 ± 0.19 |

TABLE 7-3

| Location | Pre-Processing | Size | Model 3: ViT | |
| | | | AuROC | AuPRC |
| --- | --- | --- | --- | --- |
| Anas-tomosis | Spectrogram | 374* × 128 | 0.64 ± 0.13 | 0.14 ± 0.07 |
| | | 128 × 128 | 0.61 ± 0.15 | 0.19 ± 0.23 |
| | | 32 × 128 | 0.64 ± 0.16 | 0.13 ± 0.23 |
| | Recurrence Plot | 128 × 128 | 0.51 ± 0.19 | 0.14 ± 0.22 |
| Distal | Spectrogram | 374* × 128 | 0.76 ± 0.10 | 0.72 ± 0.09 |
| | | 128 × 128 | 0.72 ± 0.11 | 0.70 ± 0.12 |
| | | 32 × 128 | 0.69 ± 0.08 | 0.63 ± 0.10 |
| | Recurrence Plot | 128 × 128 | 0.67 ± 0.11 | 0.62 ± 0.13 |
| Middle | Spectrogram | 374* × 128 | 0.85 ± 0.10 | 0.47 ± 0.23 |
| | | 128 × 128 | 0.85 ± 0.10 | 0.44 ± 0.24 |
| | | 32 × 128 | 0.83 ± 0.11 | 0.38 ± 0.29 |
| | Recurrence Plot | 128 × 128 | 0.74 ± 0.11 | 0.29 ± 0.19 |

TABLE 7-3-continued

| Location | Pre-Processing | Size | Model 3: ViT | |
| | | | AuROC | AuPRC |
| --- | --- | --- | --- | --- |
| Proximal | Spectrogram | 374* × 128 | 0.82 ± 0.12 | 0.44 ± 0.17 |
| | | 128 × 128 | 0.79 ± 0.14 | 0.39 ± 0.19 |
| | | 32 × 128 | 0.81 ± 0.14 | 0.37 ± 0.21 |
| | Recurrence Plot | 128 × 128 | 0.75 ± 0.10 | 0.32 ± 0.14 |
| Arch | Spectrogram | 374* × 128 | 0.76 ± 0.11 | 0.42 ± 0.21 |
| | | 128 × 128 | 0.72 ± 0.11 | 0.29 ± 0.10 |
| | | 32 × 128 | 0.71 ± 0.10 | 0.27 ± 0.09 |
| | Recurrence Plot | 128 × 128 | 0.68 ± 0.16 | 0.27 ± 0.20 |

As noted above, Experiment 1 compared the three model architectures and the two preprocessing methods, spectrogram generation and recurrence plot image generation, at each location. For the spectrogram images, three different sizes of varying time resolution were tested at the constant, maximum frequency resolution of 128: 374×128, 128×128, and 32×128. For the ViT, the 374×128 spectrogram image is resized to be 368×128 to be compatible with the 16×16 patch tokenization step. The ViT is therefore trained on 368×128 spectrogram images. For the recurrence plot images, a resolution of 128×128 was used. Model performance is quantified in Tables 7-1, 7-2 and 7-3 by the AuROC and AuPRC from 10-fold cross validation.

Additional experiments were performed on the above-described illustrative embodiments of FIGS. 15 and 16. Experiment 1 as described above used independent classifiers, one for each location. In Experiment 2, all the sounds from each location are aggregated to train one ViT, but without any location metadata given to the model. In Experiment 3, all the sounds from each location are aggregated and location metadata is supplied to the ViT. Comparing the results between Experiment 2 and Experiment 3, it was found that the AuROC and AuPRC improves from 0.68±0.05 and 0.28±0.09 (for the model lacking location information) to 0.82±0.04 and 0.54±0.08 (for the model considering location information), respectively. This jump in performance confirms the importance of accounting for the location along the AVF from which the sound was sourced. Using learned embeddings to encode the categorical location information provided the best performance results in these embodiments. The results for integer encoding and one-hot encoding indicate that using increasing scalar multiples of the integer encoding scheme (e.g., encoding "venous arch" as 1, 10, 100) results in progressively improved performance metrics. These results are counterintuitive because in theory it should not matter what the integer values are since the same loss function is being optimized in each case, the model can learn to increase or decrease the weights associated with location metadata and converge on the same solution. However, it seems that artificially increasing the importance of the location metadata at initialization (via larger integer values) leads to better performance. It is possible that increasing the importance at initialization either leads to faster convergence or helps the model escape a local minimum. The fact that progressively better results are achieved with increasing scalar integer encoding values further emphasizes the importance of contextualizing the sounds with location metadata.

On evaluation on the held-out test set, it can be seen that that the individual, location-based ViTs outperform the universal ViT with location metadata. The individual, location-based models implicitly contextualize the sounds with location information since they are only trained on sounds coming from the given location. The individual, location-based ViTs can focus exclusively on learning the features that distinguish patent from stenotic at that given location. The universal ViT must learn a feature extractor that generalizes across all six locations, which likely hinders performance because the relevant features that define patent versus stenotic varies with location due to inherent differences in sound at each location. What it means to be "stenotic" at the "arch" location is different than "stenotic" at the "anastomosis" location, despite both receiving the same "stenotic" label. For example, on average, the blood flow sound is louder at a patent anastomosis site compared to a stenotic venous arch site.

Additional testing was performed to determine if it is important in these embodiments to contextualize the blood flow sound with metadata regarding the anatomical original of the artery and vein used in the creation of the AVF. In this study, the AVFs were made from the brachial and radial artery, and the cephalic and basilic vein. In Experiment 4, a ViT is tested to determine if it can distinguish the brachial from the radial artery based on blood flow collected at the "artery" location. An AuROC value of 0.78±0.11 suggests that there is a difference in blood flow sound between the radial from brachial artery. The difference in sound likely stems from the fact that the brachial artery is almost two times larger than the radial artery and has thicker vessel walls. In Experiment 5, a ViT is tested to determine if it can distinguish the cephalic from the basilic vein based on blood flow collected at the "arch" location. An AuROC value of 0.52±0.13 suggests that there is not much difference in blood flow sound between a cephalic and basilic vein. The difference between the basilic and cephalic vein is only about 1-2 mm in most people, which likely explains the model's lack of ability to differentiate the sound of blood flow between the veins. In Experiment 6, tests determine how well the individual, location-based ViTs perform when also given metadata regarding the anatomical origin of either the artery or the vein. No significant improvement between the models given venous origin metadata in Experiment 6 compared with the models in Experiment 1, consistent with the lack of ability to discern cephalic from basilic vein in Experiment 5. Interestingly, despite an example model being able to distinguish the radial from the brachial artery, there is no improvement between the models given artery origin information in Experiment 6 compared with the models in Experiment 1. Thus, the anatomical original of the artery or vein seems to be unimportant in the context of building classifiers to identify AVF stenoses based on blood flow sound.

In evaluating the example test set, a simple non-deep learning approach was also tested based on the view that, on average, the blood flow through stenotic lesions is louder than through patent vessels. For each location, the half-way point between the averaged patent frequency spectrum AUC value and the averaged stenotic frequency spectrum AUC value is used as a threshold for evaluating the test set. For the test set, sounds with frequency spectra AUC values that fall above the threshold are classified as stenotic, and those with AUC values below the threshold are classified as patent. This approach gives inferior results compared to the two deep learning approaches. While general spectral properties that correlate clinically seem to emerge from the averaged frequency spectra, judging from both the large standard deviations in Table 6 and from visual inspection of individual frequency spectra, there seems to be large degree of heterogeneity among the sounds on an individual level. This underscores the need for highly parameterized deep learning models over simpler rule-based algorithms for screening for AVF stenosis based on blood flow sound. Finally, a patient-level analysis is performed on the held-out test set using the best performing model in the corresponding embodiments, and this example model was found to achieve a sensitivity, specificity, and F1 score of 0.924, 0.791, 0.907, respectively. As a reference for performance, a clinical trial that studied how well a single expert nephrologist could identify stenosis in hemodialysis arteriovenous fistulas based on a physical exam, also using ultrasound as the ground truth, reported a sensitivity of 0.96 and a specificity of 0.76. Thus, the example model is able to screen for stenosis at a level comparable to that of an expert nephrologist performing a physical exam.

The example model therefore provides an accurate and efficient approach for screening for AVF stenosis in hemodialysis patients using deep learning to analyze the sound of AVF blood flow. In routine practice, the onus of screening typically falls on the dialysis technician. The model evaluation described herein shows that this technology can screen for stenosis at a level comparable to that of a nephrologist performing the physical exam, but with the advantage of being automated and scalable. Thus, this technology could help dialysis technicians, who are often challenged with a high volume of patients each day, ensure patient safety while also streamlining workflows to reduce costs. There is potential for this technology to even be patient facing. It should be noted that the experiments dealt with brachial/radial and cephalic/basilic fistulas. Although these are the most common types of fistulas, other fistula types using other artery and veins exist, and it is possible that the anatomical origin of the artery and vein may be useful in classifying the other fistula types. Additionally, the example model cannot be used to identify stenosis on the arterial side of an AVF, although this is much rarer than stenosis on the venous side. This is due to the lack of training data for arterial stenosis in the experiments (only six examples). Also, the data was validated by identifying stenotic lesions using duplex ultrasound. Clinically, a stenotic lesion identified on ultrasound does not always necessitate a percutaneous angioplasty (the procedure for treating a stenotic AVF). An important clinical question is when to intervene on a stenotic AVF once found. While some embodiments disclosed herein provide deep learning based classification of blood flow sound as a quick and economical screening tool for identifying the presence of stenotic lesions, additional embodiments can be configured in a straightforward manner to correlate blood flow sounds to AVFs that ultimately require percutaneous angioplasties.

The various experiments performed on the illustrative embodiments of FIGS. 15, 16 and 17 are summarized as follows.

Experiment 1 tests independent, location-based binary classifiers, one for each of the following locations: anastomosis, distal, middle, proximal, and arch. In other words, each location-based model is trained only on sounds originating at the given location. This experiment does not build a model for the arterial location given that there are only six examples of stenosis. For each location, the three different model architectures of FIG. 16 (a 6-layer CNN, a ResNet-50 pretrained on ImageNet weights, and a ViT) are tested with the two preprocessing methods (spectrograms and recurrence plot images). For the spectrogram images, three different sizes of varying time resolution are tested at the constant, maximum frequency resolution of 128: 374×128, 128×128, and 32×128. Note that for the ViT, the 374×128 spectrogram image is resized to be 368×128 to be compatible with the 16×16 patch tokenization step.

Experiment 2 tests a ViT trained on 368×128 spectrogram images to determine its performance in classifying the blood flow audio signal as patent or stenotic using audio signals from all six locations, but without supplying the model with any metadata regarding the location from which the sound is sourced. The ViT in this experiment thus operates as a universal binary classifier to distinguish patent versus stenotic, with no location metadata. The 368×128 spectrogram images from every location are aggregated together and used to train the ViT without supplying the model with any metadata about the particular location from which the spectrogram is sourced.

Experiment 3 tests a ViT trained on 368×128 spectrogram images to determine its performance in classifying the blood flow audio signal as patent or stenotic using audio signals from all six locations, this time with location metadata regarding the location from which the sound is sourced being explicitly fed into the model. This is accomplished by first encoding the categorical location information into a numerical representation, and then concatenating that numerical representation to the feature vector coming from the last transformer encoder layer, as illustrated in the modified ViT architecture of FIG. 17. The 368×128 spectrogram images from every location are aggregated together to train the modified ViT, this time with location metadata supplied to the model. Three different methods of encoding the categorical location metadata are also tested in these illustrative embodiments: an ordinal encoding where each location is encoded as an integer, a one-hot encoding, and a learned embedding. For the ordinal encoding, the effects of using scalar multiples of the integer encodings are also tested. For the learned embedding, a 6×4 embedding matrix E is learned as part of the training. As an example, the categorical location information is first one-hot encoded, then fed into an embedding layer that converts the one-hot encoded vectors into a dense numerical vector representation that is then concatenated to the flattened feature vector. As indicated above, the embedding layer is illustratively trained along with the ViT.

Experiment 4 tests whether a binary classifier can distinguish if the blood flow audio signal is coming from either the radial or brachial artery. For this task, the ViT is trained on spectrogram images using only patent radial and patent brachial sounds taken at the "artery" location.

Experiment 5 tests whether a binary classifier can distinguish if the blood flow audio signal is coming from either the basilic or cephalic vein. For this task, the ViT is trained on spectrogram images using only patent cephalic and patent basilic sounds taken at the "arch" location.

Experiment 6 tests how well a ViT trained on 368×128 spectrogram images performs in classifying the blood flow audio signals as patent or stenotic when also given information about the anatomical original of either the artery or vein used in the creation of the fistula, for each location. This is accomplished in a parallel manner to Experiment 3, where first the categorical information about the anatomical origin of the artery or vein is encoded as different integers (1 for brachial artery, 0 for radial artery; 1 for cephalic vein, 0 for basilic vein), and then concatenated to the feature vector coming from the last transformer encoder layer. As indicated previously, an illustration of this modified ViT architecture is shown FIG. 17.

Blood flow sound data from a total of 433 patients with AVFs was used in this study of illustrative embodiments. Patients that were both actively receiving dialysis through their AVF and those with pre-emptively placed AVF in light of deteriorating kidney function were included in this study.

Patients with arteriovenous fistulas, created with either the radial or brachial artery and either the cephalic or basilic vein, were recruited for this study. On the arterial side, 80% of patients had fistulas created from the brachial artery; 20% of patients had fistulas created from the radial artery. On the venous side, 65% of patients had fistulas created from the cephalic vein, 35% of patients had fistulas created from the basilic vein. In summary, four fistula variations are analyzed in this study: brachiocephalic fistulas (52%), brachiobasilic fistulas (28%), radiocephalic fistulas (13%), radiobasilic fistulas (7%).

For each patient, blood flow sounds were collected at six different locations along the patient's AVF, as illustrated in part (b) of FIG. 15. Of the six sounds, one was collected from the artery, one was collected at the anastomosis site (i.e., where the artery has been surgically joined to the vein), and four sounds were collected along the vein. The locations were designated, from most distal to most proximal, as "arterial" for the artery, "anastomosis" for the anastomosis site, "distal" for the distal vein, "middle" for the middle vein, "proximal" for the proximal vein, and "arch" for the arch of the vein (i.e., the point along the fistula closest to the shoulder). The terminology "proximal" and "distal" is used based on the anatomic definitions of the arm. A total of 2529 AVF blood flow sounds were included in this study. Sounds were collected using a digital stethoscope at a sampling rate of 4000 Hz. Each sound was recorded for 15 seconds.

The sounds from the blood flow were labeled as "patent" (normal) or "stenotic" (abnormal). The labels are validated from concurrent duplex ultrasound (blood flow sound recorded by stethoscope and ultrasound imaging were done at the same time). The final label of "patent" versus "stenotic" at each location was determined after interpretation of the corresponding ultrasound imaging and velocity reports by a board-certified vascular surgeon. The example dataset included 2088 patent sounds (83%) and 441 stenotic sounds (17%).

The data was divided into train, validate, and test sets. First, 20% of the data was randomly reserved to serve as the held-out test set for final model evaluation. Then the remaining 80% of the data was split into train and validate sets following a 10-fold cross-validation procedure. This procedure is used throughout the experiments (explained in more detail below) for model training, model hyperparameter tuning and optimization, and comparison among models.

Three different example deep learning models were tested in these illustrative embodiments, as shown in FIG. 16: a CNN trained with no preset weights, a ResNet-50 pretrained on ImageNet, and a ViT with no preset weights.

The example CNN comprises six convolutional layers, as shown in Model 1 of FIG. 16. The number of filters used was 8, 16, 32, 64, 128, 256 for the $1^{st}$, $2^{nd}$, $3^{rd}$, 4th, $5^{th}$, $6^{th}$ layer, respectively. Each layer uses a ReLU activation function. Following each convolutional layer was a max pooling and batch normalization layer. After the six convolutional layers, the feature vector is flattened via global average pooling. The feature vector is then fed into three fully connected layers comprising 32 nodes, 16 nodes, and 1 node, respectively. The first two fully connected layers use a ReLU activation function, while the last node uses a sigmoid activation function to perform the final binary classification of "patent" versus "stenotic." This model was trained using an adaptive moment estimation (Adam) optimizer at a learning rate of $1\times10^{-3}$. To address the issue of class imbalance, a weighted binary cross-entropy loss function which gives more importance to the minority class (i.e., the stenotic sounds) is used to calculate the loss. The class weights ratio used mirror the inverse of the class distribution in the training set. The same weighted binary cross-entropy loss function is used with the other models as well.

The second example model was a ResNet-50, shown as Model 2 in FIG. 16. In brief, a ResNet-50 is a CNN that is 50 layers deep with residual or skip connections that allows activations from earlier layers to be propagated down to deeper layers. For this model, transfer learning is leveraged as the ResNet-50 is pretrained on ImageNet21k, a large dataset that includes over 14 million natural images that belong to over 20,000 classes. One fully connected layer comprising one node with a sigmoid activation function was added on top of the ResNet-50 to perform the final binary classification of "patent" versus "stenotic." This model was trained using an Adam optimizer over the weighted binary cross-entropy loss function. First, the ResNet-50 weights were kept frozen and only the final fully connected layer was trained at a learning rate of $1\times10^{-3}$. Then the entire model (ResNet-50 plus the fully connected layer) was fine-tuned, with trained at a learning rate of $1\times10^{-5}$.

The final example model was a ViT, shown as Model 3 of FIG. 16. For this example ViT, first the model input is tokenized into 16×16 patches. The patches are flattened and fed into a linear transformation layer to create a lower dimensional embedding and combined with positional encodings, which are learnable embeddings. The embedded patches are then input into a sequence of 10 transformer encoders. Each transformer encoder comprises two subcomponents. For each encoder, the first subcomponent is a 6-headed multi-attention layer, which implements the multi-headed self-attention mechanism. The second subcomponent for each encoder is a fully connected feed-forward network using ReLU activation functions. After the 10 transformer encoders, the feature vector is flattened and passed to three fully connected layers comprising 2048 nodes, 1024 nodes, and 1 node, respectively. The first two fully connected layers use a ReLU activation function, while the last node uses a sigmoid activation function to perform the final binary classification of patent versus stenotic. This model was trained using an adaptive moment estimation (Adam) optimizer at a learning rate of $1\times10^{-3}$ over the weighted binary cross-entropy loss function.

All models are trained for 200 epochs, and the weights that correspond to the lowest validation loss are take to be the final model weights.

The three example models work with two-dimensional image data, while the raw audio data is one-dimensional timeseries data. To make the data compatible with the models, the audio data is first preprocessed into two-dimensional image representations. Two different image representations of sound are utilized in these embodiments: Mel-scaled, decibel (dB)-scaled spectrograms and recurrence plots.

As indicated elsewhere herein, a spectrogram depicts the spectrum of frequencies of a signal as it varies with time. In some embodiments, the x-axis represents time, the y-axis represents frequency, and amplitude of a particular frequency component at a given point in time is represented by the intensity of color. The spectrograms are generated from the AVF blood flow sounds using short-time Fourier transforms as follows. First, the audio signals are windowed using a Hann window of size 512 and a hop length of 256. A 512-point fast Fourier transform is applied to each window to generate a spectrogram. The Mel-scaled, dB-scaled spectrograms are generated by logarithmic rescaling of the amplitude and frequency axis. The amplitude axis is converted to the dB scale. The frequency axis is transformed onto the Mel scale, in the manner described elsewhere herein. The resulting Mel-scaled, dB-scaled spectrograms are 374×128 (time resolution×frequency resolution) in size. To determine the effects of varying time resolution on the spectrogram image, spectrograms with dimensions 128×128 and 32×128 are also created using bicubic interpolation.

Also as described previously, a recurrence plot is an image that visualizes the set of all pairs in time $(t_n, t_m)$ in which $\vec{x}(t_n) = \vec{x}(t_m)$, where $\bar{x}$ is the systems trajectory vector through the phase space. The phase space is a multidimensional space that represents every possible state of a system, with each degree of freedom of a system represented as an axis. In these illustrative embodiments, recurrence plots of the frequency spectrum are generated. First, a Fourier transform is applied over the entire audio signal to generate the frequency spectrum. Then the frequency spectrum is discretized. For example, let $T = \{t_0, t_1, t_2, \ldots t_n \ldots t_N\}$ represent the discretized points over which the frequency spectrum spans, separated by the interval $\delta$. Then the trajectory of the frequency spectrum through the phase space is given by $\vec{X} = \{\vec{x}(t_0), \vec{x}(t_1), \vec{x}(t_2), \ldots \vec{x}(t_n) \ldots \vec{x}(t_N)\}$. The recurrence states of $\vec{x}(t_n)$ are states $\vec{x}(t_m)$ that fall within a given radius $\epsilon$ around $\vec{x}(t_n)$. The recurrence plot is constructed as an N×N lattice of squares with side length $\delta$ and with each coordinate axis reporting T. The value at coordinates $(t_n, t_m)$ is given by the recurrence value function $R(t_n, t_m) = \Theta(\epsilon - \|\vec{x}(t_n) - (t_m)\|)$, where $\Theta$ is the Heaviside step function. The final recurrence plots are size 128×128.

An averaged frequency spectrum is computed across all patients in the train and validate sets, stratified by label and location. Four spectral parameters are extracted from each frequency spectrum: total AUC, peak frequency, max frequency, and FWHM, as compiled in Table 6. The frequency spectrum is used to extract four spectral parameters from each AVF recording. Total AUC is approximated using the composite trapezoidal rule for definite integrals, defined as $$\int_a^b f(x)dx = \frac{1}{2}\sum_{j=1}^n (x_j - x_{j-1})[f(x_j) + f(x_{j-1})],$$

with partition length of 0.1 (i.e., $x_j - x_{j-1} = 0.1$) and frequency range (a-b) of 0-2000 Hz. Peak frequency ($x_{peak}$) is defined as the frequency value that corresponds to the peak of the highest amplitude. Maximum frequency is estimated as the highest frequency with amplitude greater than 0.1. FWHM is calculated using the horizontal frequency span at half of the maximum amplitude, where FWHM=$x_n - x_m$, and $$f(x_n) = f(x_m) = \frac{1}{2}f(x_{peak}).$$

A simple, non-deep learning approach is also tested using the AUC values from the averaged frequency spectra. For each location, the half-way point between the averaged patent frequency spectrum AUC value and the averaged stenotic frequency spectrum AUC value is used as a threshold for evaluating the test set. For the test set, frequency spectra AUC values that fall above the threshold are classified as stenotic, and those with AUC values below the threshold are classified as patent.

The held-out test set was evaluated in the following manner. Confusion matrices were determined for the individual, location-based ViT trained on 368×128 spectrogram images. Additional confusion matrices were determined for the universal ViT trained 368×128 spectrogram images with location metadata. The results were stratified by location to allow for side-by-side comparison. Further confusion matrices were determined for a simple, non-deep learning approach for detecting stenosis at each location. Here the averaged AUC value of the averaged patent and stenotic frequency spectra is used as a threshold for deciding how to classify each sound in the test set. For example, at the anastomosis site the AUC of the averaged patent frequency spectrum is 2772 and the AUC of the averaged stenotic frequency spectrum is 4142. The average of the two AUC values is 3457. In the test set, if a sound has a frequency spectrum AUC greater than 3457, it is classified as stenotic, and vice versa.

Table 8 below summarizes the sensitivity, specificity, and F1 score for these three approaches.

TABLE 8

| | Location | Sensitivity | Specificity | F1 Score |
|---|---|---|---|---|
| Individual Location-Based Models | Anastomosis | 0.941 | 0.942 | 0.821 |
| | Distal | 0.961 | 0.846 | 0.891 |
| | Middle | 1.000 | 0.841 | 0.400 |
| | Proximal | 0.846 | 0.864 | 0.579 |
| | Arch | 0.938 | 0.816 | 0.667 |
| Universal Model with Location Metadata | Anastomosis | 0.706 | 0.385 | 0.258 |
| | Distal | 0.765 | 0.646 | 0.690 |
| | Middle | 0.833 | 0.805 | 0.303 |
| | Proximal | 0.846 | 0.806 | 0.500 |
| | Arch | 0.750 | 0.632 | 0.429 |
| Non-Deep Learning Approach | Anastomosis | 0.118 | 0.894 | 0.133 |
| | Distal | 0.176 | 0.954 | 0.286 |
| | Middle | 0.333 | 0.929 | 0.250 |
| | Proximal | 0.077 | 0.961 | 0.111 |
| | Arch | 0.125 | 0.934 | 0.174 |

Patient level analysis was performed as follows. A confusion matrix was determined for the individual, location-based ViT trained on 368×128 spectrogram images evaluated on the test set at the patient level. At the patient level, the patient is considered a "stenotic patient" if the patient has a stenotic lesion anywhere along their arteriovenous fistula. If the patient has no stenotic lesions anywhere, then the patient is counted as a "patent patient." For the predicted label for each patient, each individual, location-based model must predict patent at every location for the overall prediction to be a patent prediction. If any of the individual, location-based models predicts stenosis, then the overall prediction is counted as stenotic. For this patient level analysis, the sensitivity, specificity, and F1 score for the patient-level analysis were 0.924, 0.791 and 0.907, respectively.

The particular embodiments of FIGS. 13 through 17, like other embodiments disclosed herein, are presented by way of non-limiting example only, and should not be construed as limiting in any way.

As indicated previously, these and other embodiments disclosed herein provide significant advantages over conventional approaches.

For example, some embodiments apply a 2-D CNN or other type of neural network on image representations of acoustic signals, thereby providing enhanced accuracy and efficiency in classification of biomedical acoustics.

These and other embodiments can be fully automated and do not require any costly and time-consuming manual adjustments such as feature-based classification or predetermined logic rules.

For example, illustrative embodiments do not require feature extraction from acoustic signal waveforms, but instead takes as input the undifferentiated frequency and time domain information for classification. This input in some embodiments is more particularly in the form of a raw encoded image comprising RGB components, again without any need for feature extraction. Classification in illustrative embodiments therefore does not require the comparison of an input feature vector to a set of stored feature vectors.

In addition, illustrative embodiments herein are not restricted to binary classification (e.g., only being able to classify normal vs. abnormal). Instead, some embodiments are configured to achieve a higher level of granularity and thus can come to actual diagnoses (e.g., normal heart sound vs. aortic stenosis vs. mitral regurgitation, etc.)

Moreover, illustrative embodiments do not require pre-processing steps specific to phonocardiogram (PCG) signal analysis (e.g., segmentation into S1, S2, systole, and diastole) and do not require use of features that are specific to PCG signals (e.g., PCG interval parameters). Accordingly, some embodiments do not rely on any preprocessing step or feature extraction that is inherently based on any one type of biomedical sound, and thus these embodiments can be readily generalized to multiple biomedical sounds of different types.

In some embodiments, by classifying the image representation of the acoustic signal, problematic issues with conventional segmentation approaches are avoided. Such embodiments therefore have the advantage of being useful in a broader range of scenarios, including many real-world, clinical setting such as classifying heart sounds in pediatric patients who have increased heart rates and a high incidence of innocent murmurs.

Furthermore, by using images instead of audio signals, illustrative embodiments enable a full suite of data augmentation techniques to generate more labeled training data than would otherwise be available. This includes, for example, image cropping, rotation, flipping, and scaling. By enabling the use of these and other data augmentation techniques, illustrative embodiments can further improve classification performance by forcing the model to learn the relevant features that characterize each acoustic signal.

For example, in some embodiments, multiple different forms of data augmentation at both the sound and image level may be used. Additionally, both the original and the augmented signals are illustratively used to train the neural network(s) in some embodiments in order to minimize overfitting and improve dataset diversity.

These and other advantages referred to herein are illustratively present in some embodiments, but need not be present in all embodiments. Other embodiments can provide different arrangements of advantages, depending upon their particular implementations.

The particular configurations as shown in the figures are non-limiting and should be considered illustrative examples only. Numerous other types of system architectures can be used in other embodiments. Also, other types of machine learning and/or artificial intelligence architectures, illustratively implementing other types of neural networks, can be used in other embodiments. Accordingly, illustrative embodiments herein are not limited to use with CNNs or other particular types of neural networks.

The system 100 can be configured to support a wide variety of distinct applications, in numerous diverse contexts.

For example, illustrative embodiments of the system 100 are configured to detect various physiological conditions, based on acoustic signals collected from sensors or other signal sources utilized by, on or otherwise in association with a patient, possibly including passive sensing data collected with little to no user interaction, from one or more mobile sensors (e.g., one or more internal devices of the patient, one or more wearable devices of the patient, a smartphone of the patient, etc.)

In an example use case, illustrative embodiments disclosed herein are configured to distinguish innocent pediatric heart murmurs from pathological pediatric heart murmurs. It takes 10,000 hours of listening to heart sounds for training physicians to be able to decisively distinguish between the different heart sounds. In practice, these 10,000 hours are only undertaken by the most specialized physicians, leaving a significant gap in cardiac auscultation skills in the primary care setting. This has significant implications in pediatric care, where 75% of newborns and 66% of all children present with a heart murmur, but only 1% of children have a congenital heart disease. In fact, 800,000 innocent murmur referrals are made each year in the US, costing the healthcare system upwards of one billion dollars from unnecessary imaging and appointments with specialists. A biomedical acoustics classifier configured using the techniques disclosed herein can provide substantially more accurate and efficient diagnoses, in this and other contexts, than is possible under conventional practice.

Other example use cases involve the classification of blood flow sounds, lung sounds (e.g., crackles, wheezes, etc.), bowel sounds, sounds from neurons during deep brain stimulation surgery as the micro-electrode passes through the brain cells, sounds from muscle cells contracting during an electromyography study, as well as numerous other types of biomedical acoustics, such as classification of emotions from a baby's cry.

In still further use cases, a wide variety of different machine learning or other artificial intelligence training and validation implementations can benefit greatly from the use of synthetic spectrograms or other synthetic image representations generated using the synthetic data generation techniques disclosed herein.

Illustrative embodiments can therefore generate more labeled acoustic signal training data from existing acoustic signal data to greatly expand the training set for any machine learning model attempting to classify acoustic signals.

It is to be appreciated that the particular use cases described herein are examples only, intended to demonstrate utility of illustrative embodiments, and should not be viewed as limiting in any way.

Automated remedial actions taken based on outputs generated by a classification algorithm of the type disclosed herein can include particular actions involving interaction between a processing platform implementing the classification algorithm and other related equipment utilized in one or more of the use cases described above. For example, outputs generated by a classification algorithm can control one or more components of a related system. In some embodiments, the classification algorithm and the related equipment are implemented on the same processing platform, which may comprise a computer, a smartphone, a wearable device, an internal device, an intelligent stethoscope, a handheld sensor device or other type of processing device.

It should also be understood that the particular arrangements shown and described in conjunction with FIGS. 1 through 17 are presented by way of illustrative example only, and numerous alternative embodiments are possible. The various embodiments disclosed herein should therefore not be construed as limiting in any way. Numerous alternative arrangements of classification algorithms can be utilized in other embodiments. Those skilled in the art will also recognize that alternative processing operations and associated system entity configurations can be used in other embodiments.

It is therefore possible that other embodiments may include additional or alternative system elements, relative to the entities of the illustrative embodiments. Accordingly, the particular system configurations and associated algorithm implementations can be varied in other embodiments.

A given processing device or other component of an information processing system as described herein is illustratively configured utilizing a corresponding processing device comprising a processor coupled to a memory. The processor executes software program code stored in the memory in order to control the performance of processing operations and other functionality. The processing device also comprises a network interface that supports communication over one or more networks.

The processor may comprise, for example, a microprocessor, an ASIC, an FPGA, a CPU, a TPU, a GPU, an ALU, a DSP, or other similar processing device component, as well as other types and arrangements of processing circuitry, in any combination. For example, at least a portion of the functionality of at least one biomedical acoustics classifier or an associated classification and/or remediation algorithm provided by one or more processing devices as disclosed herein can be implemented using such circuitry.

The memory stores software program code for execution by the processor in implementing portions of the functionality of the processing device. A given such memory that stores such program code for execution by a corresponding processor is an example of what is more generally referred to herein as a processor-readable storage medium having program code embodied therein, and may comprise, for example, electronic memory such as SRAM, DRAM or other types of random access memory, ROM, flash memory, magnetic memory, optical memory, or other types of storage devices in any combination.

As mentioned previously, articles of manufacture comprising such processor-readable storage media are considered embodiments of the invention. The term "article of manufacture" as used herein should be understood to exclude transitory, propagating signals. Other types of computer program products comprising processor-readable storage media can be implemented in other embodiments.

In addition, embodiments of the invention may be implemented in the form of integrated circuits comprising processing circuitry configured to implement processing operations associated with implementation of a classification algorithm.

An information processing system as disclosed herein may be implemented using one or more processing platforms, or portions thereof.

For example, one illustrative embodiment of a processing platform that may be used to implement at least a portion of an information processing system comprises cloud infrastructure including virtual machines implemented using a hypervisor that runs on physical infrastructure. Such virtual machines may comprise respective processing devices that communicate with one another over one or more networks.

The cloud infrastructure in such an embodiment may further comprise one or more sets of applications running on respective ones of the virtual machines under the control of the hypervisor. It is also possible to use multiple hypervisors each providing a set of virtual machines using at least one underlying physical machine. Different sets of virtual machines provided by one or more hypervisors may be utilized in configuring multiple instances of various components of the information processing system.

Another illustrative embodiment of a processing platform that may be used to implement at least a portion of an information processing system as disclosed herein comprises a plurality of processing devices which communicate with one another over at least one network. Each processing device of the processing platform is assumed to comprise a processor coupled to a memory. A given such network can illustratively include, for example, a global computer network such as the Internet, a WAN, a LAN, a satellite network, a telephone or cable network, a cellular network such as a 3G, 4G or 5G network, a wireless network implemented using a wireless protocol such as Bluetooth, WiFi or WiMAX, or various portions or combinations of these and other types of communication networks.

Again, these particular processing platforms are presented by way of example only, and an information processing system may include additional or alternative processing platforms, as well as numerous distinct processing platforms in any combination, with each such platform comprising one or more computers, servers, storage devices or other processing devices.

A given processing platform implementing a classification algorithm as disclosed herein can alternatively comprise a single processing device, such as a computer, a smartphone, a wearable device, an internal device, an intelligent stethoscope or handheld sensor device, that implements not only the classification algorithm but also at least one acoustic signal source and one or more controlled components. It is also possible in some embodiments that one or more such system elements can run on or be otherwise supported by cloud infrastructure or other types of virtualization infrastructure.

It should therefore be understood that in other embodiments different arrangements of additional or alternative elements may be used. At least a subset of these elements may be collectively implemented on a common processing platform, or each such element may be implemented on a separate processing platform.

Also, numerous other arrangements of computers, servers, storage devices or other components are possible in an information processing system. Such components can communicate with other elements of the information processing system over any type of network or other communication media.

As indicated previously, components of the system as disclosed herein can be implemented at least in part in the form of one or more software programs stored in memory and executed by a processor of a processing device. For example, certain functionality disclosed herein can be implemented at least in part in the form of software.

The particular configurations of information processing systems described herein are exemplary only, and a given such system in other embodiments may include other elements in addition to or in place of those specifically shown, including one or more elements of a type commonly found in a conventional implementation of such a system.

For example, in some embodiments, an information processing system may be configured to utilize the disclosed techniques to provide additional or alternative functionality in other contexts.

It should again be emphasized that the embodiments of the invention as described herein are intended to be illustrative only. Other embodiments of the invention can be implemented utilizing a wide variety of different types and arrangements of information processing systems, biomedical acoustics classifiers, neural networks and processing devices than those utilized in the particular illustrative embodiments described herein, and in numerous alternative processing contexts. In addition, the particular assumptions made herein in the context of describing certain embodiments need not apply in other embodiments. These and numerous other alternative embodiments will be readily apparent to those skilled in the art.

What is claimed is:

1. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein generating the image representation comprises generating at least one spectrogram;

wherein the method further comprises applying transformations to respective axes of the generated spectrogram prior to processing the spectrogram in the neural network, and wherein applying the transformations comprises:

applying a first transformation of a first type to a first axis of the spectrogram; and applying a second transformation of a second type different than the first type to a second axis of the spectrogram;

wherein the method is performed by at least one processing device comprising a processor coupled to a memory.

2. The method of claim 1 wherein the acoustic signal comprises at least one of a heart sound signal, a blood flow sound signal, a lung sound signal, a bowel sound signal, a cough sound signal, a nerve conduction sound signal, a neuronal cell firing sound signal, a muscle cell contraction sound signal, a subcutaneous emphysema sound signal, or other physiological sound signal of the given individual.

3. The method of claim 1 wherein the spectrogram represents frequency, time and amplitude in respective dimensions thereof.

4. The method of claim 1 wherein generating the spectrogram comprises:

segmenting the acoustic signal into a plurality of overlapping windows; and applying a Fourier transform to each of at least a subset of a plurality of resulting segments to generate the spectrogram.

5. The method of claim 1 wherein at least one of the first and second transformations applied to at least one axis of the spectrogram comprises a transformation from a linear scale to a logarithmic scale.

6. The method of claim 1 wherein applying transformations to respective axes of the spectrogram further comprises:

applying a third transformation of a third type different than the first type and the second type to a third axis of the spectrogram.

7. The method of claim 1 wherein applying a first transformation of a first type to a first axis of the spectrogram comprises applying a Mel-scale transformation to a frequency axis of the spectrogram.

8. The method of claim 1 wherein applying a second transformation of a second type to a second axis of the spectrogram comprises applying a decibel-scale transformation to an amplitude axis of the spectrogram.

9. The method of claim 1 wherein generating the image representation comprises generating at least one recurrence plot.

10. The method of claim 1 wherein the neural network comprises a two-dimensional convolutional neural network including a first convolutional layer, a first max pooling layer, a second convolutional layer, a second max pooling layer, a fully connected layer, and at least one of a built-in activation function and an activation layer.

11. The method of claim 1 wherein the image representation is processed in a first neural network, and the method further comprises:

generating a power spectrum representation of at least a portion of the acoustic signal;

processing the power spectrum representation in a second neural network different than the first neural network, at least in part in parallel with the processing of the image representation in the first neural network; and generating the classification for the acoustic signal utilizing outputs of the first and second neural networks.

12. The method of claim 1 wherein the image representation comprises an image representation of a first type processed in a first neural network, and the method further comprises:

generating a second type of image representation of at least a portion of the acoustic signal, the image representation of the second type being different than the image representation of the first type;

processing the image representation of the second type in a second neural network different than the first neural network, at least in part in parallel with the processing of the image representation of the first type in the first neural network; and generating the classification for the acoustic signal utilizing outputs of the first and second neural networks.

13. The method of claim 12 wherein the first type of image representation comprises a spectrogram and the second type of image representation comprises a recurrence plot.

14. The method of claim 1 wherein executing at least one automated action based at least in part on the generated classification comprises generating at least one output signal in a telemedicine application, wherein said at least one output signal in a telemedicine application comprises at least one of:

classification information for presentation on a user terminal or other display device;

classification information transmitted over a network to a medical professional; and classification information transmitted over a network to a prescription-filling entity.

15. The method of claim 1 wherein the neural network comprises a vision transformer configured to implement a self-attention mechanism.

16. The method of claim 1 wherein the neural network comprises an involutional neural network.

17. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein the method further comprises processing a first image representation generated from the acoustic signal to generate a second image representation, the second image representation being a synthetic image representation, wherein at least the second image representation is processed in the neural network; and wherein the method is performed by at least one processing device comprising a processor coupled to a memory.

18. The method of claim 17 wherein generating the second image representation from the first image representation comprises at least one of:

applying a masking operation of a first type to a first axis of the first image representation; and applying a masking operation of a second type to a second axis of the first image representation.

19. The method of claim 17 wherein generating the second image representation from the first image representation comprises:

utilizing the first image representation to train a Generative Adversarial Network (GAN); and utilizing the trained GAN to generate the second image representation.

20. The method of claim 17 wherein generating the second image representation from the first image representation comprises performing at least one instance of flipping the first image representation about a specified axis.

21. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein processing the image representation in at least one neural network of an acoustics classifier comprises:

processing a first image representation of a first acoustic signal having an unknown classification in a first neural network;

processing a second image representation of a second acoustic signal having a known classification in a second neural network arranged in parallel with the first neural network;

encoding outputs of the respective first and second neural networks;

computing a distance measure between the encoded outputs; and generating a classification for the first acoustic signal based at least in part on the computed distance measure; and wherein the method is performed by at least one processing device comprising a processor coupled to a memory.

22. The method of claim 21 wherein the acoustics classifier is trained using a contrastive loss function, and wherein generating the classification for the first acoustic signal based at least in part on the computed distance measure comprises processing the computed distance measure in the acoustics classifier trained using the contrastive loss function to generate the classification for the first acoustic signal.

23. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein processing the image representation in at least one neural network of an acoustics classifier comprises:

processing a first image representation of a first acoustic signal having an unknown classification in a first neural network;

processing a second image representation of a second acoustic signal having a known classification of one type in a second neural network arranged in parallel with the first neural network;

processing a third image representation of a third acoustic signal having a known classification of another type in a third neural network arranged in parallel with the first and second neural networks;

encoding outputs of the respective first, second and third neural networks;

computing distance measures between respective pairs of the encoded outputs; and generating a classification for the first acoustic signal based at least in part on the computed distance measures; and wherein the method is performed by at least one processing device comprising a processor coupled to a memory.

24. The method of claim 23 wherein the acoustics classifier is trained using a triplet loss function, and wherein generating the classification for the first acoustic signal based at least in part on the computed distance measures comprises processing the computed distance measures in the acoustics classifier trained using the triplet loss function to generate the classification for the first acoustic signal.

25. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein generating the image representation comprises generating at least one Markov transition field image representation of at least a portion of the acoustic signal in at least one of a time domain and a frequency domain; and wherein the method is performed by at least one processing device comprising a processor coupled to a memory.

26. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein generating the image representation comprises generating at least one Gramian angular field image representation utilizing at least one of (i) one or more trigonometric summations of at least a portion of the acoustic signal in a time domain, (ii) one or more trigonometric summations of at least a portion of the acoustic signal in a frequency domain, (iii) one or more trigonometric differences of at least a portion of the acoustic signal in the time domain, and (iv) one or more trigonometric differences of at least a portion of the acoustic signal in the frequency domain; and wherein the method is performed by at least one processing device comprising a processor coupled to a memory.

27. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein generating the image representation comprises performing a channeling operation to concatenate at least one image representation along a channel dimension of the neural network where each channel of the channel dimension of the neural network processes a different one of a plurality of image representations; and wherein the method is performed by at least one processing device comprising a processor coupled to a memory.

28. A method comprising:

obtaining an acoustic signal for a given individual;

generating an image representation of at least a portion of the acoustic signal;

processing the image representation in at least one neural network of an acoustics classifier to generate a classification for the acoustic signal; and executing at least one automated action based at least in part on the generated classification;

wherein the neural network comprises a vision transformer configured to implement a self-attention mechanism;

wherein the vision transformer comprises a sequence of transformer encoders, with a final transformer encoder of the sequence of transformer encoders generating a flattened feature vector, and further wherein the vision transformer is further configured to combine an encoded categorical input with the flattened feature vector; and wherein the method is performed by at least one processing device comprising a processor coupled to a memory.

29. A system comprising:

at least one processing device comprising a processor coupled to a memory;

the processing device being configured:

to obtain an acoustic signal for a given individual;

to generate an image representation of at least a portion of the acoustic signal;

to process the image representation in at least one neural network of an acoustics classifier to generate a classification for the acoustic signal; and to execute at least one automated action based at least in part on the generated classification;

wherein generating the image representation comprises generating at least one spectrogram; and wherein the processing device is further configured to apply transformations to respective axes of the generated spectrogram prior to processing the spectrogram in the neural network, and wherein applying the transformations comprises:

applying a first transformation of a first type to a first axis of the spectrogram; and applying a second transformation of a second type different than the first type to a second axis of the spectrogram.

30. The system of claim 29 wherein generating the image representation further comprises generating at least one of:

at least one recurrence plot;

at least one Markov transition field image representation; and at least one Gramian angular field image representation.

31. A computer program product comprising a non-transitory processor-readable storage medium having stored therein program code of one or more software programs, wherein the program code, when executed by at least one processing device comprising a processor coupled to a memory, causes the processing device:

to obtain an acoustic signal for a given individual;

to generate an image representation of at least a portion of the acoustic signal;

to process the image representation in at least one neural network of an acoustics classifier to generate a classification for the acoustic signal; and to execute at least one automated action based at least in part on the generated classification;

wherein generating the image representation comprises generating at least one spectrogram; and wherein the program code when executed further causes the processing device to apply transformations to respective axes of the generated spectrogram prior to processing the spectrogram in the neural network, and wherein applying the transformations comprises:

applying a first transformation of a first type to a first axis of the spectrogram; and applying a second transformation of a second type different than the first type to a second axis of the spectrogram.

32. The computer program product of claim 31 wherein generating the image representation further comprises generating at least one of:

at least one recurrence plot;

at least one Markov transition field image representation; and at least one Gramian angular field image representation.

33. The computer program product of claim 31 wherein applying transformations to respective axes of the spectrogram further comprises:

applying a third transformation of a third type different than the first type and the second type to a third axis of the spectrogram.

34. The computer program product of claim 31 wherein applying a first transformation of a first type to a first axis of the spectrogram comprises applying a Mel-scale transformation to a frequency axis of the spectrogram, and wherein applying a second transformation of a second type to a second axis of the spectrogram comprises applying a decibel-scale transformation to an amplitude axis of the spectrogram.

* * * * *